US009655679B2

(12) United States Patent
Desai et al.

(10) Patent No.: US 9,655,679 B2
(45) Date of Patent: May 23, 2017

(54) ACTUATED STEERABLE PROBE AND SYSTEMS AND METHODS OF USING SAME

(71) Applicant: UNIVERSITY OF MARYLAND, OFFICE OF TECHNOLOGY COMMERCIALIZATION, College Park, MD (US)

(72) Inventors: Jaydev P. Desai, Bethesda, MD (US); Elif Ayvali, College Park, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 13/875,204

(22) Filed: May 1, 2013

(65) Prior Publication Data

US 2013/0296885 A1    Nov. 7, 2013

Related U.S. Application Data

(60) Provisional application No. 61/641,158, filed on May 1, 2012.

(51) Int. Cl.
| | |
|---|---|
| *A61B 1/00* | (2006.01) |
| *A61B 19/00* | (2006.01) |
| *A61B 17/34* | (2006.01) |
| *A61B 90/11* | (2016.01) |
| *A61B 1/04* | (2006.01) |
| *A61B 17/00* | (2006.01) |
| *A61B 90/00* | (2016.01) |
| *A61B 34/20* | (2016.01) |

(52) U.S. Cl.
CPC ........ *A61B 19/201* (2013.01); *A61B 17/3417* (2013.01); *A61B 17/3421* (2013.01); *A61B 90/11* (2016.02); *A61B 90/39* (2016.02); *A61B 2017/003* (2013.01); *A61B 2017/00867* (2013.01); *A61B 2034/2055* (2016.02); *A61B 2090/3735* (2016.02)

(58) Field of Classification Search
CPC ... A61B 1/0053; A61B 1/0057; A61B 1/0058; A61B 19/201; A61B 17/3417; A61B 17/3421; A61B 90/11; A61B 2017/003
USPC ........ 600/139, 141, 143, 104, 114, 117, 171
See application file for complete search history.

(56) References Cited

U.S. PATENT DOCUMENTS

| | | | | |
|---|---|---|---|---|
| 4,697,577 | A * | 10/1987 | Forkner ........................ | 600/173 |
| 5,873,817 | A * | 2/1999 | Kokish et al. ................ | 600/143 |
| 6,135,946 | A * | 10/2000 | Konen et al. ................. | 600/117 |
| 7,658,709 | B2 * | 2/2010 | Anderson et al. ............ | 600/143 |
| 2004/0056751 | A1 * | 3/2004 | Park et al. .................... | 337/139 |
| 2005/0256429 | A1 * | 11/2005 | Long et al. ................... | 600/585 |
| 2006/0232669 | A1 * | 10/2006 | Abadie ................ A61B 1/0058 | 348/76 |
| 2007/0239138 | A1 * | 10/2007 | Lawrence et al. ............ | 604/531 |
| 2010/0010298 | A1 * | 1/2010 | Bakos et al. ................. | 600/106 |
| 2010/0160731 | A1 * | 6/2010 | Giovannini et al. .......... | 600/117 |
| 2013/0090528 | A1 * | 4/2013 | Ramamurthy et al. ....... | 600/117 |

* cited by examiner

*Primary Examiner* — Timothy J Neal
(74) *Attorney, Agent, or Firm* — Rosenberg, Klein & Lee

(57) ABSTRACT

A steerable probe having high-power-density actuators positioned at joints along the length of the probe. The actuators are moveable about and between a straight position and a curved position in response to selective actuation.

31 Claims, 46 Drawing Sheets

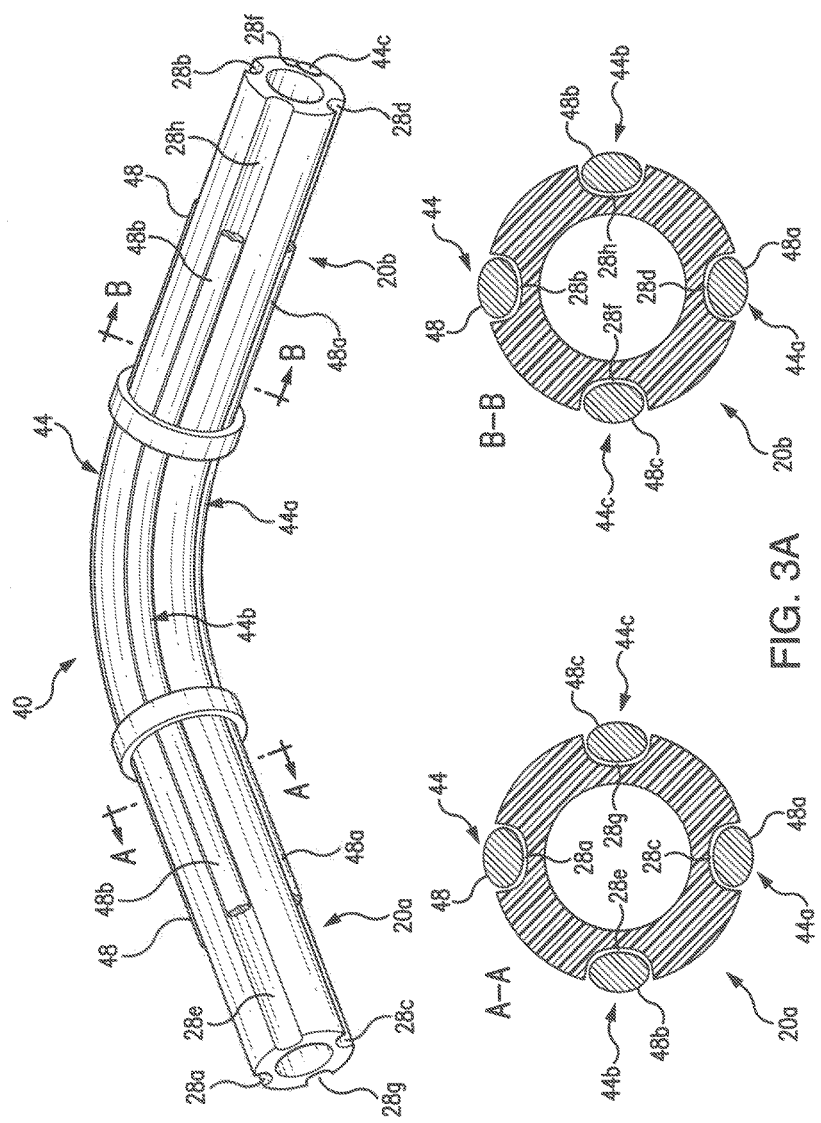

(a) Movement of the obstacles and the motion of the cannula (b) Change in joint variables with time (a) Movement of the obstacles and the motion of the cannula (b) Change in joint variables with time (a)

(b)

(a)

(b)

ACTUATED STEERABLE PROBE AND SYSTEMS AND METHODS OF USING SAME

CROSS-REFERENCE TO RELATED APPLICATIONS

This application claims the benefit of U.S. Provisional Application No. 61/641,158, filed May 1, 2012, which is incorporated by reference herein in its entirety.

STATEMENT OF GOVERNMENT SUPPORT

This invention was made with United States government support under Grant CCF0704138, awarded by the National Science Foundation, and Grant 1R01EB00871301A1, awarded by the National Institutes of Health. The government has certain rights in this invention.

FIELD

This invention relates to steerable probes. In exemplary applications, the steerable probes can be used in medical procedures.

BACKGROUND

Surgical tools such as needles and cannulas are widely used in medical procedures. Several percutaneous needle-based procedures employ needles with a bevel or a symmetric tip for a specific procedure. In almost all instances, these needles need to be 'steered' to the target location by a variety of maneuvers at the distal end of the needle. Often, these needles need to be re-introduced or withdrawn slightly to correct for errors in targeting resulting from needle and soft tissue interaction. The problem is further compounded when there is a change in the tissue consistency as the needle traverses through the tissue or the tissue includes calcified regions, which can deflect the needle from its pre-planned trajectory. Some of the common examples where percutaneous needle-based procedures are employed are in prostate biopsy and breast biopsy (prostate cancer and breast cancer being the most prevalent cancers detected in men and women, respectively, in the US).

Trajectory corrections must be made during needle steering in order for the needle to reach its target. When flexible needles with a bevel tip are inserted into soft-tissue, they bend due to tip asymmetry. Taking advantage of this fact, steering of flexible needles can be accomplished by rotating the needle base during insertion to steer around obstacles. However, there is no local actuation along the length of the flexible needle, and this method of steering relies entirely on tissue reaction forces. The minimum radius of curvature is also limited, further limiting the steering capability.

Thus, there is a need in the pertinent art for medical probes (such as needles or cannulas) that overcome tissue reaction forces, achieve precise positioning, and exert force on soft-tissue to make appropriate trajectory corrections during insertion.

SUMMARY

Described herein is a steerable probe. The probe can have a central axis, a first end, and an opposed second end. The probe has a length corresponding to the distance between the first end and the second end of the probe. The probe includes a plurality of spaced segments. Each segment of the plurality of spaced segments can define a respective central bore that surrounds the central axis of the probe. The central bores of the plurality of spaced segments cooperate to define an inner channel of the probe. The probe also includes at least one joint assembly. Each joint assembly includes at least one actuator, such as, for example and without limitation, a shape memory alloy (SMA) actuator. Each actuator can be secured to adjacent segments of the plurality of spaced segments such that each segment of the plurality of spaced segments is operatively coupled to an adjacent segment of the plurality of spaced segments. Each actuator can have a bending element. Optionally, when the actuator is an SMA actuator, the bending element can be a bending portion of the actuator that is integrally formed with the remaining portions of the actuator. The bending element of each actuator can be positioned in between the adjacent segments of the plurality of spaced segments, thereby defining a respective joint of the probe.

Each actuator can be configured for selective actuation. In response to actuation, the bending element of each actuator can be configured for movement about and between a straight position and a curved position, thereby adjusting the shape of the probe at each joint along the length of the probe.

The described probe can be provided as part of a probe system. In addition to the probe, the probe system can include means for selectively effecting movement of the bending element of each actuator about and between the straight position and the curved position. Optionally, the probe system can also include imaging means for producing at least one image depicting the location of the probe. Methods of using the probe and probe system are also disclosed.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

Figure 4:
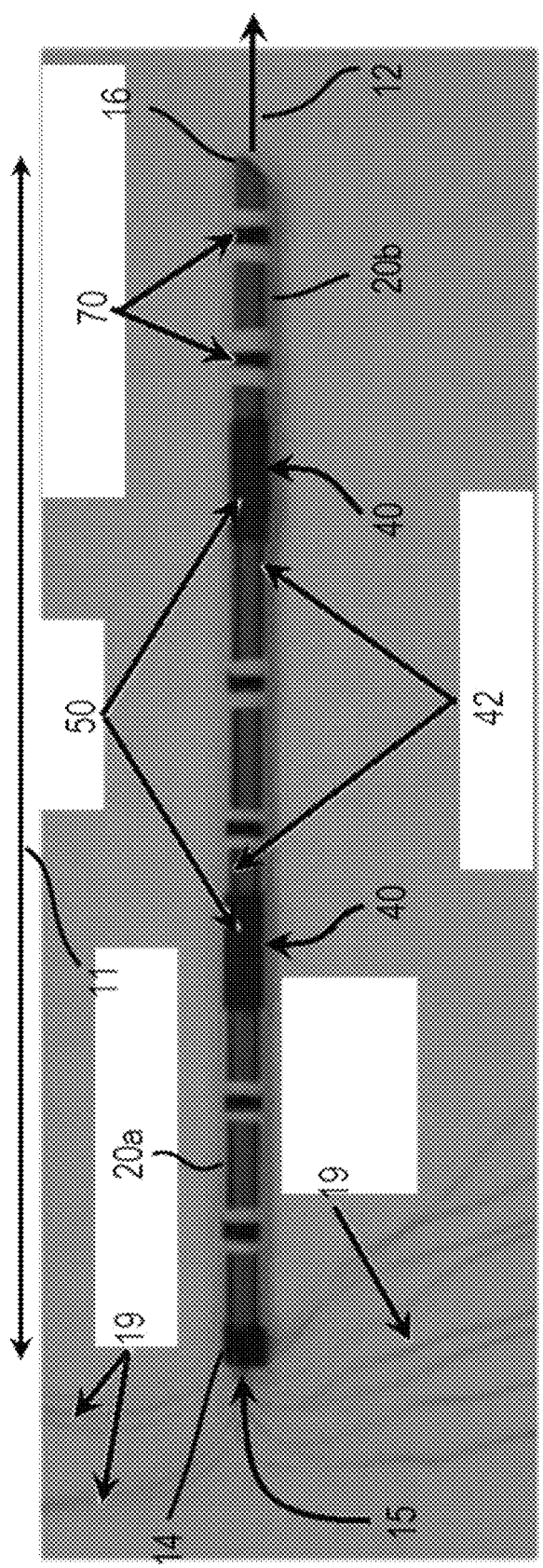

FIG. 4 depicts an exemplary probe having two degrees of freedom as disclosed herein. Each depicted joint assembly comprises two SMA actuators, with each SMA actuator having a bending portion and one degree of freedom. Markers are attached on the outer surface of the probe for tracking as disclosed herein.

FIG. 3A depicts a schematic view of the subject probe showing the specifics of the interaction of the SMA actuator members and the slots.

Figure 5:
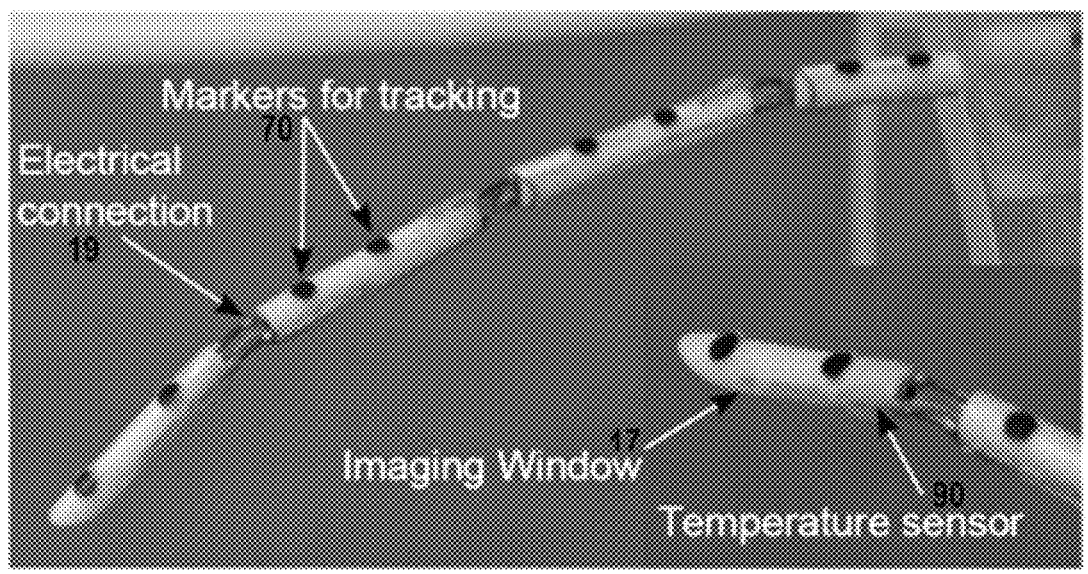

FIG. 5 depicts an exemplary probe as disclosed herein, with each depicted joint assembly having one degree of freedom and two antagonistic SMA actuators.

Figure 6A:
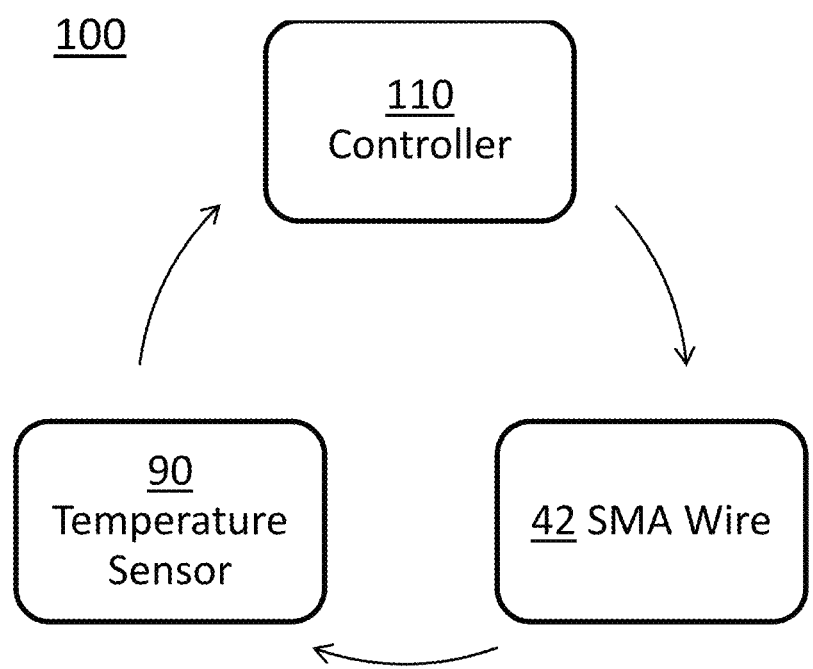
Figure 6B:
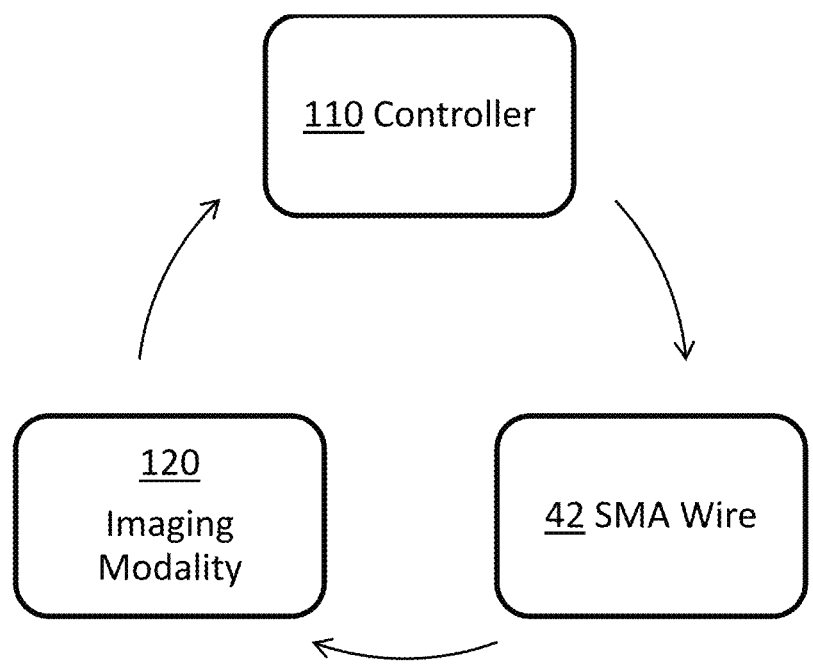

FIG. 6A depicts an exemplary probe system having a temperature feedback mechanism for controlling the actuation of SMA actuators of a probe as disclosed herein. FIG. 6B depicts an exemplary probe system having a position feedback mechanism for controlling the actuation of SMA actuators of a probe as disclosed herein.

FIGS. 7-15 are associated with Example One, as described herein.

Figure 7:
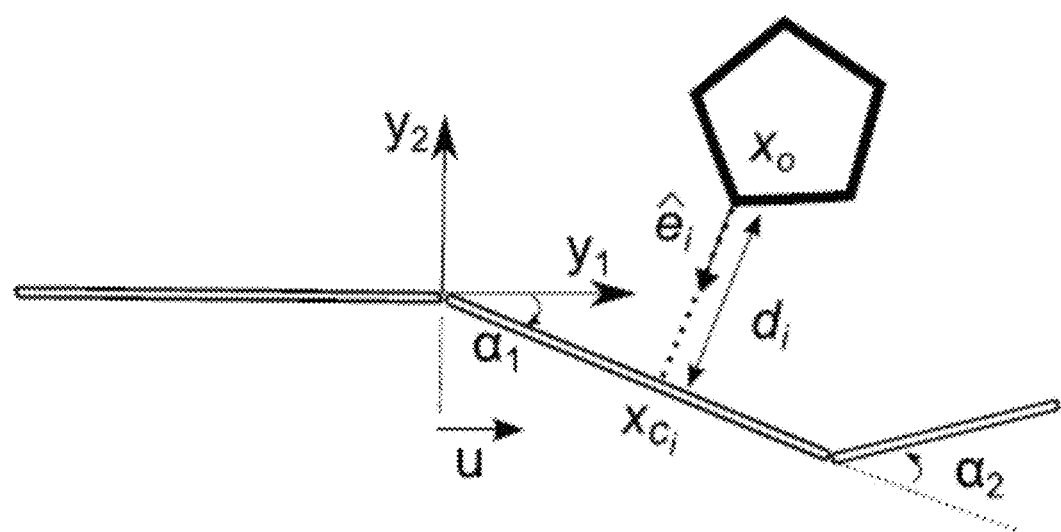

FIG. 7 depicts the variables used in geometric relations for calculating singularity and obstacle avoidance.

Figure 8:
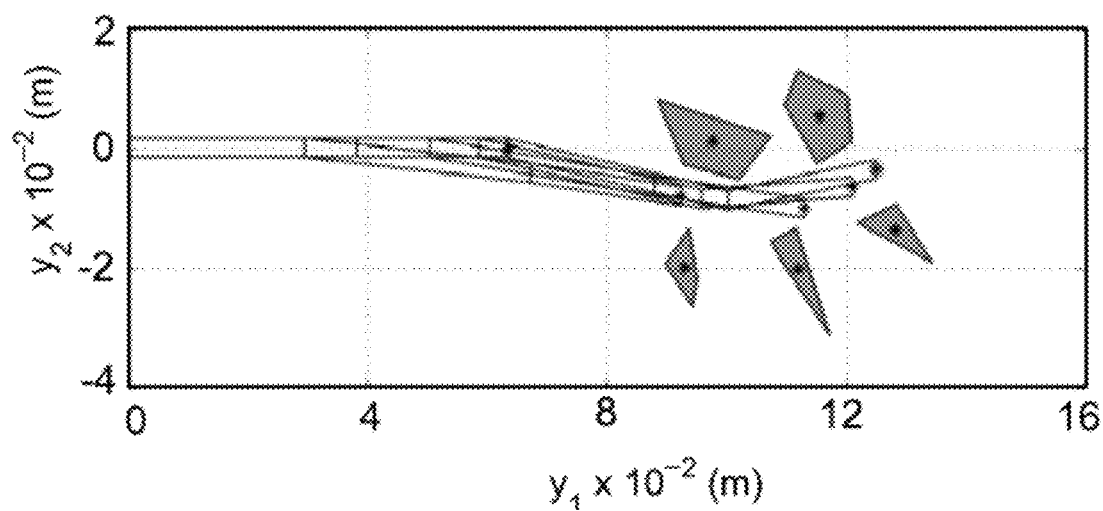

FIG. 8 depicts an example to illustrate the physical joint limit of the SMA actuator. The obstacles and the final position are inside the workspace of the cannula. However, the maximum joint angle required for trajectory can be 25.0726 degrees which can be 4.0726 degrees above the physical limit of the SMA actuator.

Figure 9:
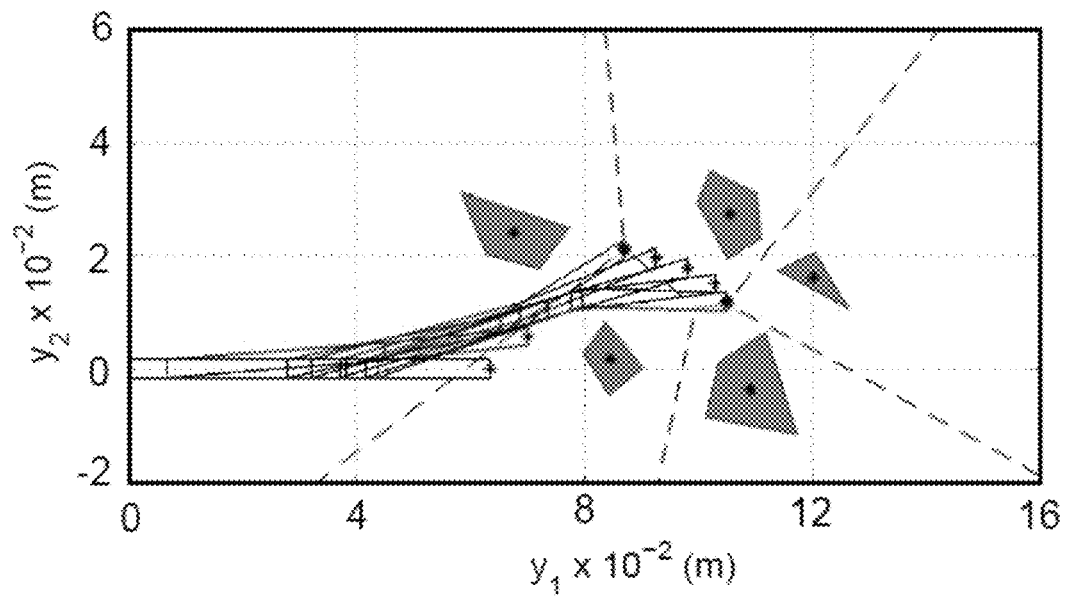

FIG. 9 depicts a motion planning problem used for analyzing the joint limit of the SMA actuator.

Figure 10:
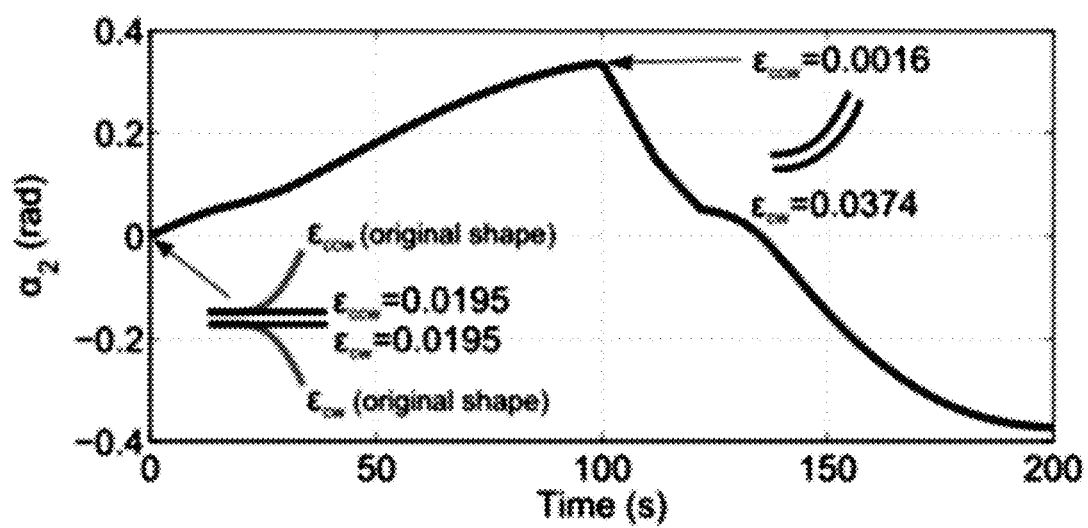

FIG. 10 depicts a change in joint angle $\alpha_2$ with time for the trajectory shown in FIG. 9.

Figure 11:
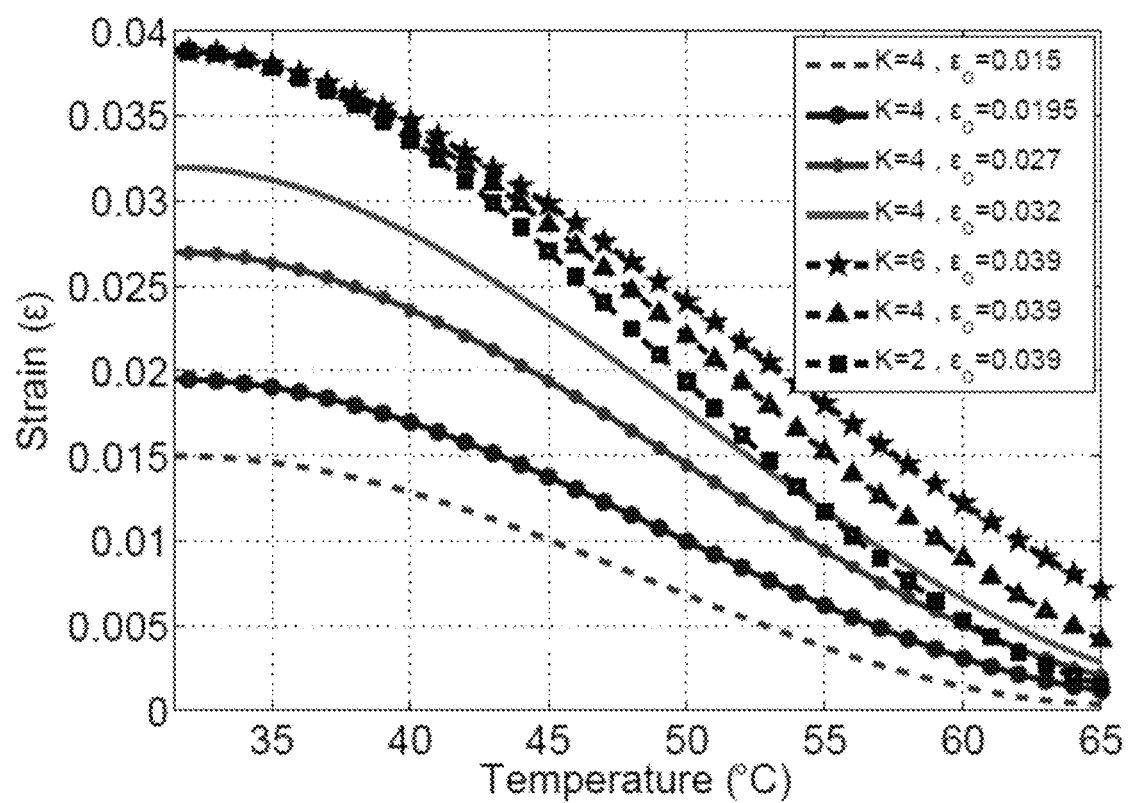

FIG. 11 depicts the relationship that the maximum recoverable strain of the SMA actuator depends on the initial strain $\epsilon_o$ and the tissue stiffness K.

Figure 12:
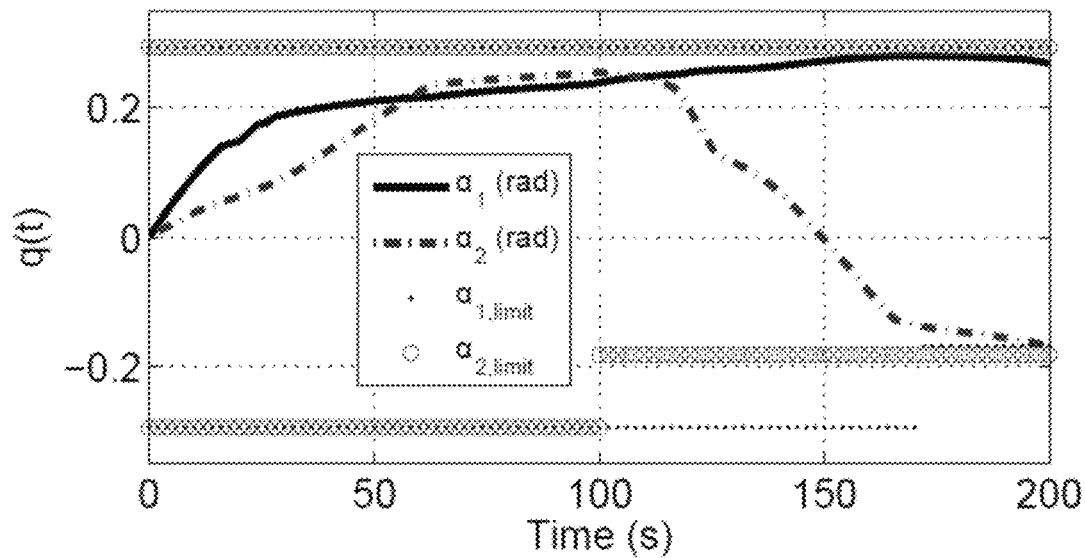

FIG. 12 depicts a change in actuator joint limits over time.

Figure 13:
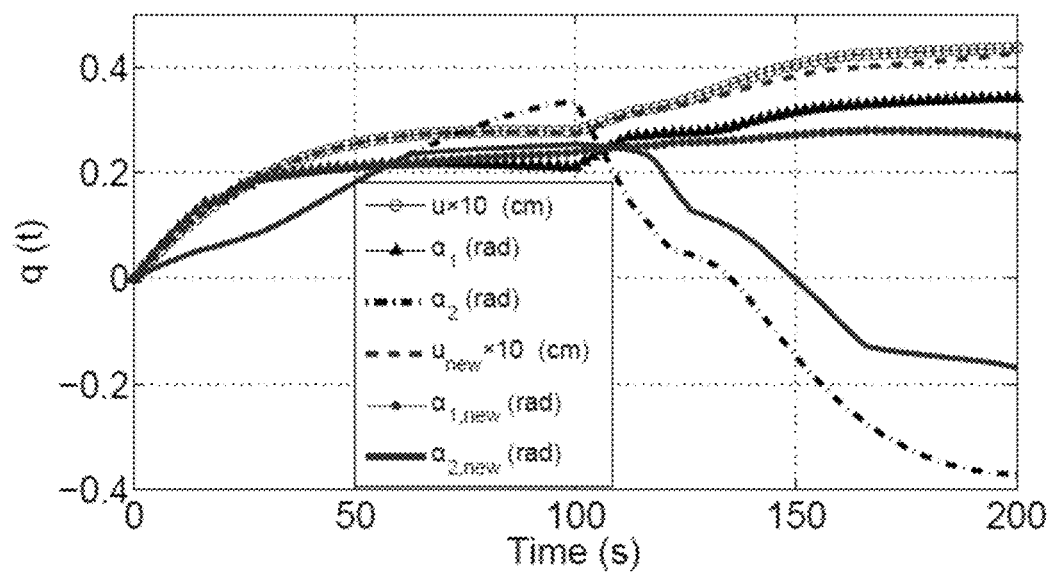

FIG. 13 depicts a change in joint variables with and without the additional task of joint limit avoidance. The case with joint limit avoidance has the joint variable with subscript new.

Figure 14:
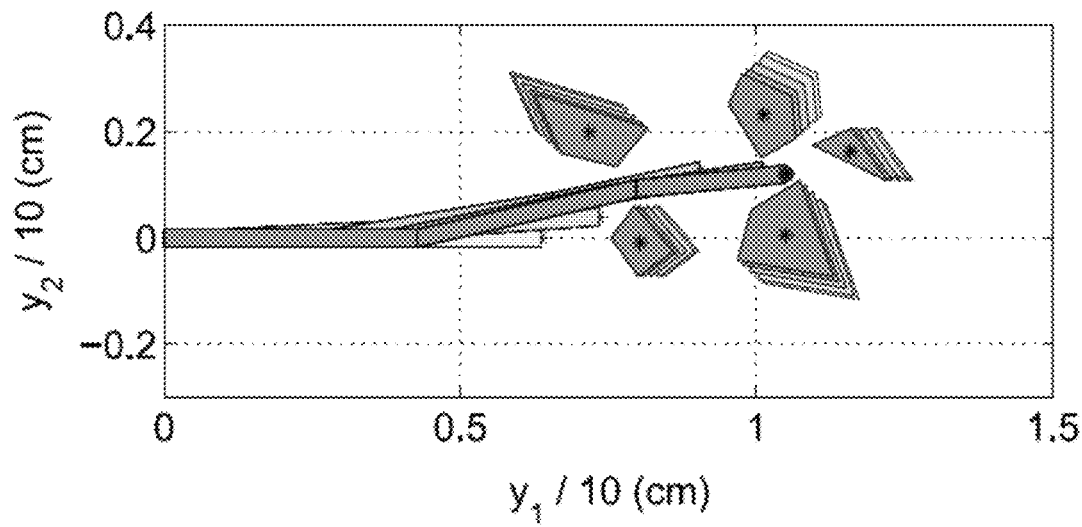
Figure 14:
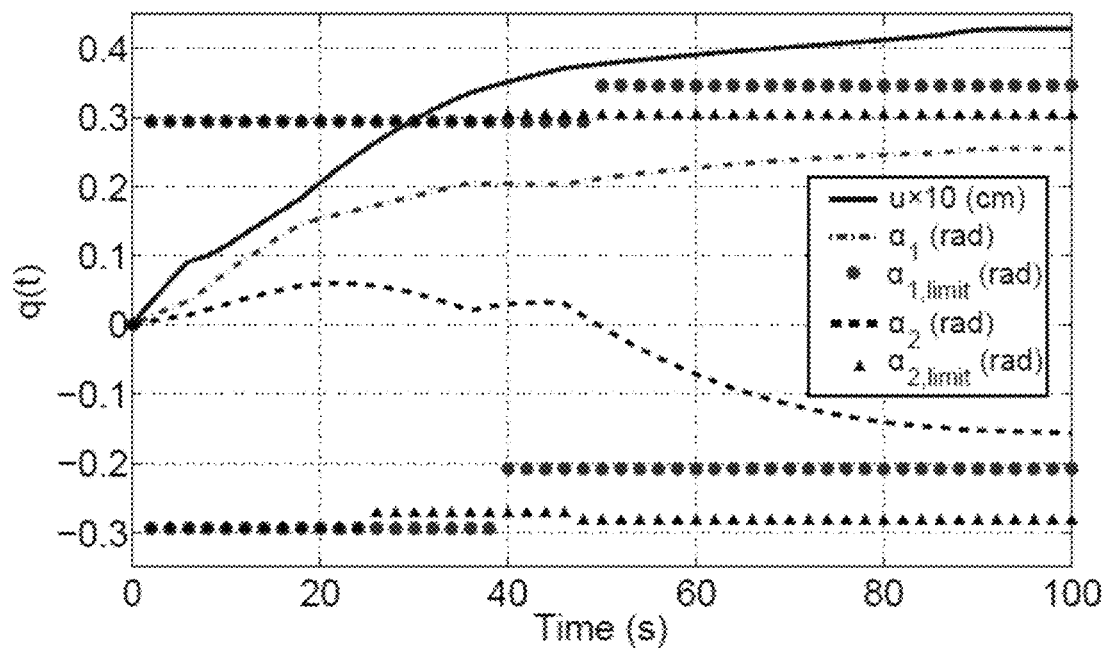

FIG. 14 depicts an example of cannula movement with the cannula and the obstacles shown in a darker color as the time progresses. FIG. 14(a) shows the movement of the obstacles and the motion of the cannula. FIG. 14(b) shows the change in joint variables with time.

Figure 15:
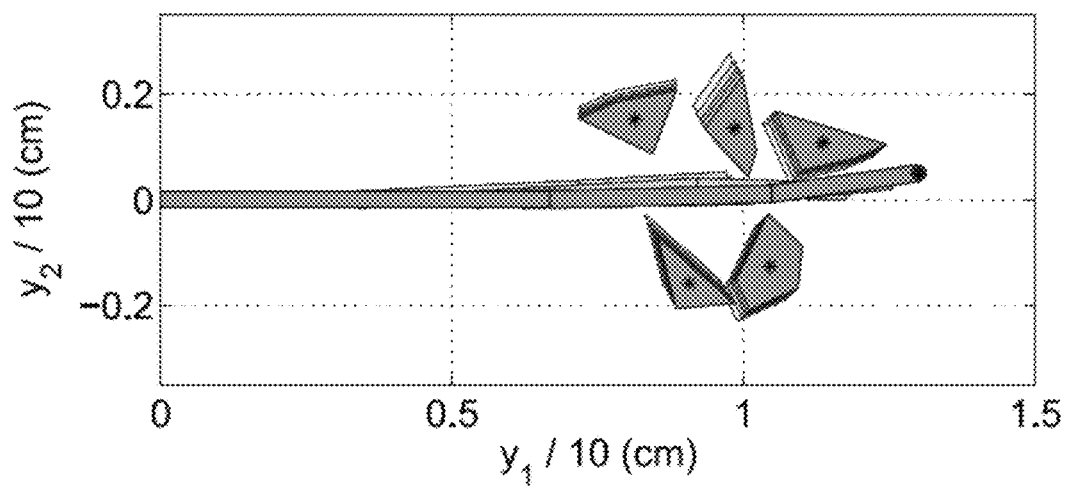
Figure 15:
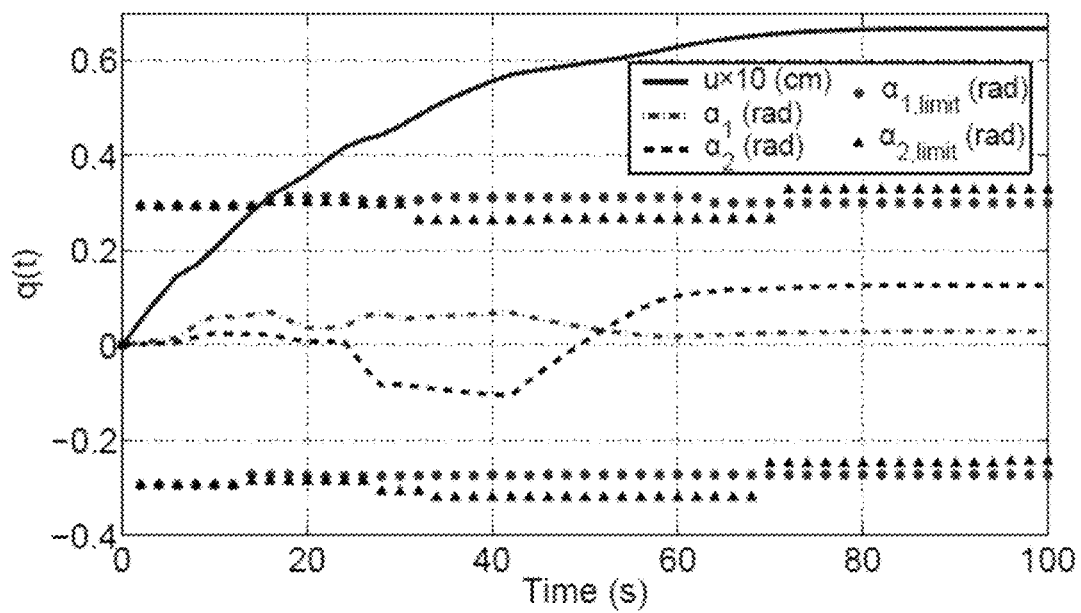

FIG. 15 depicts an example of cannula movement with the cannula and the obstacles shown in a darker color as the time progresses. FIG. 15(a) shows the movement of the obstacles and the motion of the cannula. FIG. 15(b) shows the change in joint variables with time.

FIGS. 16-24 are associated with Example Two, as described herein.

Figure 16:
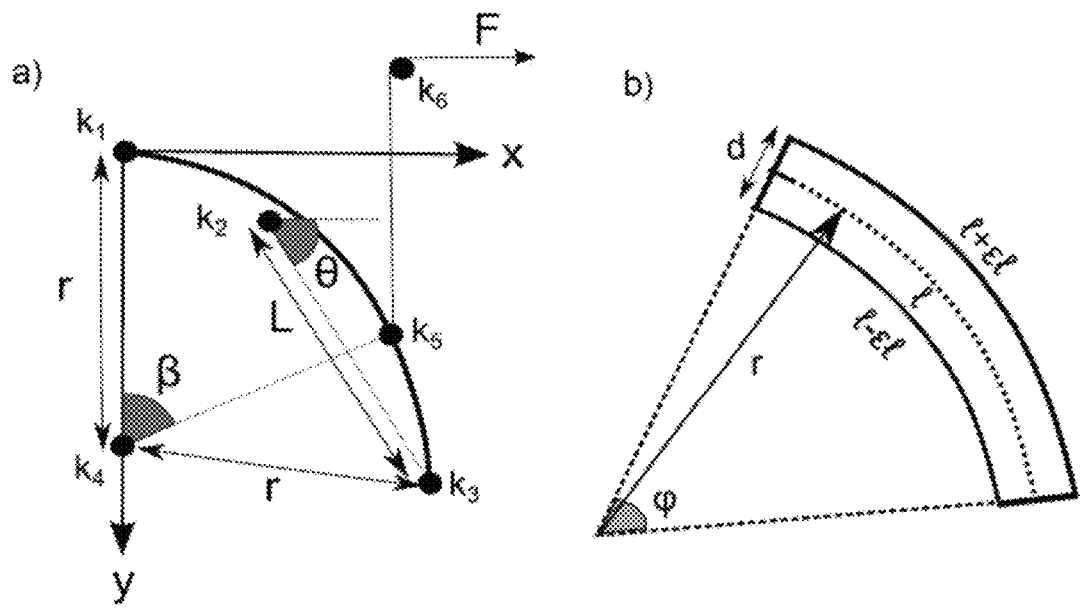

FIG. 16 depicts (a) geometric relations for the experimental setup described in Example 2, and (b) relation between strain and arc radius.

Figure 17:
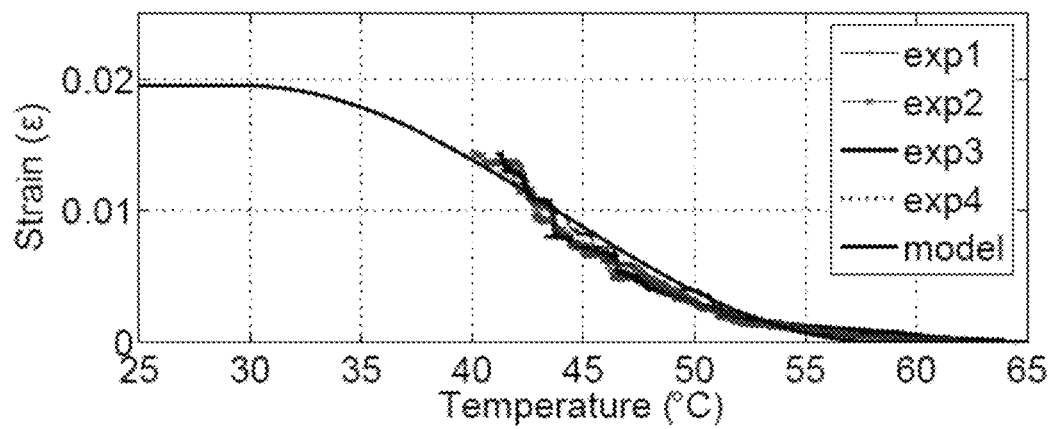

FIG. 17 depicts the relationship for strain vs. temperature for an exemplary SMA wire under no loading.

Figure 18:
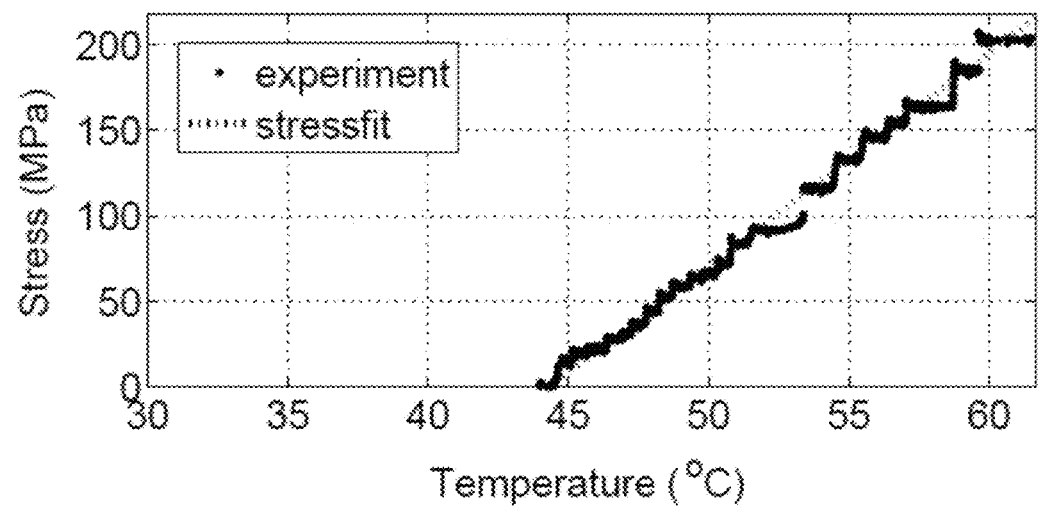

FIG. 18 depicts external stress acting on an exemplary SMA wire as a function of the temperature.

Figure 19:
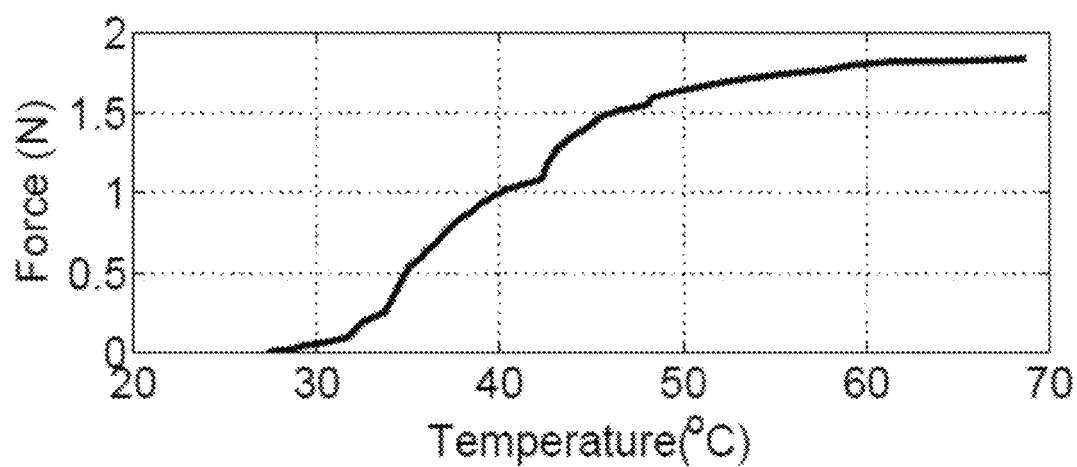

FIG. 19 depicts a force vs. temperature plot for an exemplary SMA wire.

Figure 20:
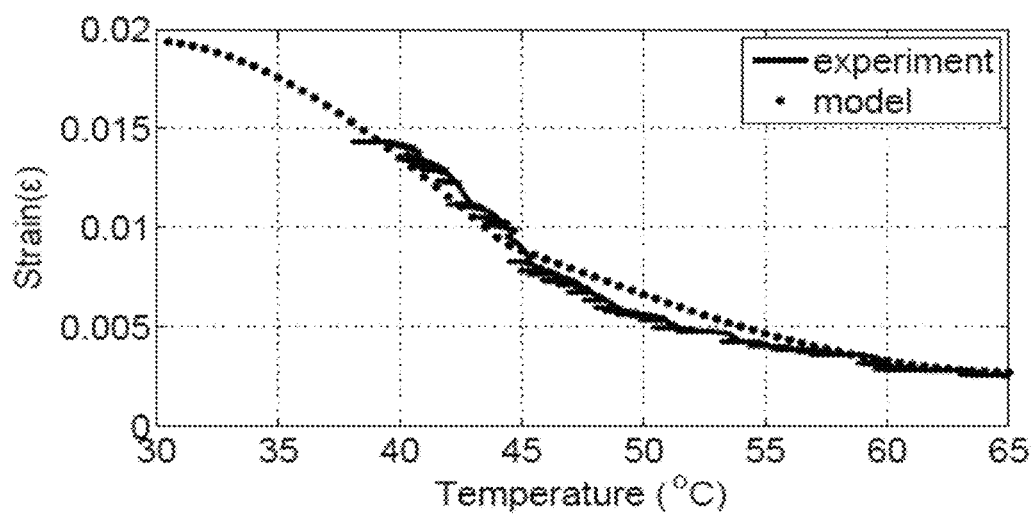

FIG. 20 depicts a strain vs. temperature relationship under variable loading.

Figure 21:
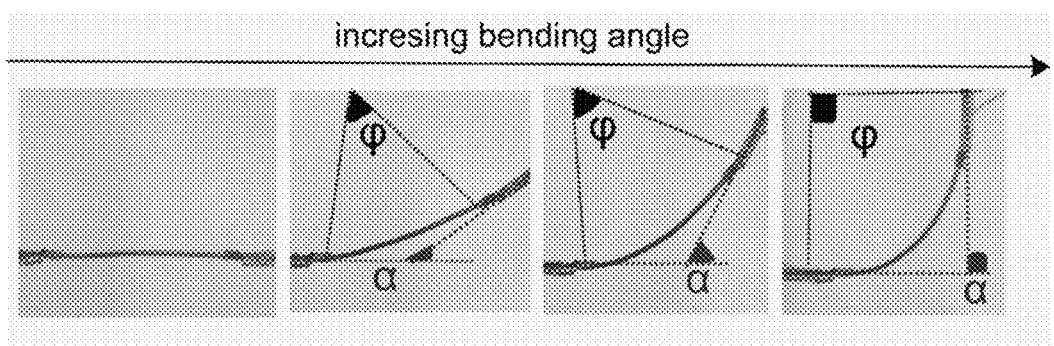

FIG. 21 depicts the change in the bending angle as an exemplary SMA wire is heated up.

Figure 22:
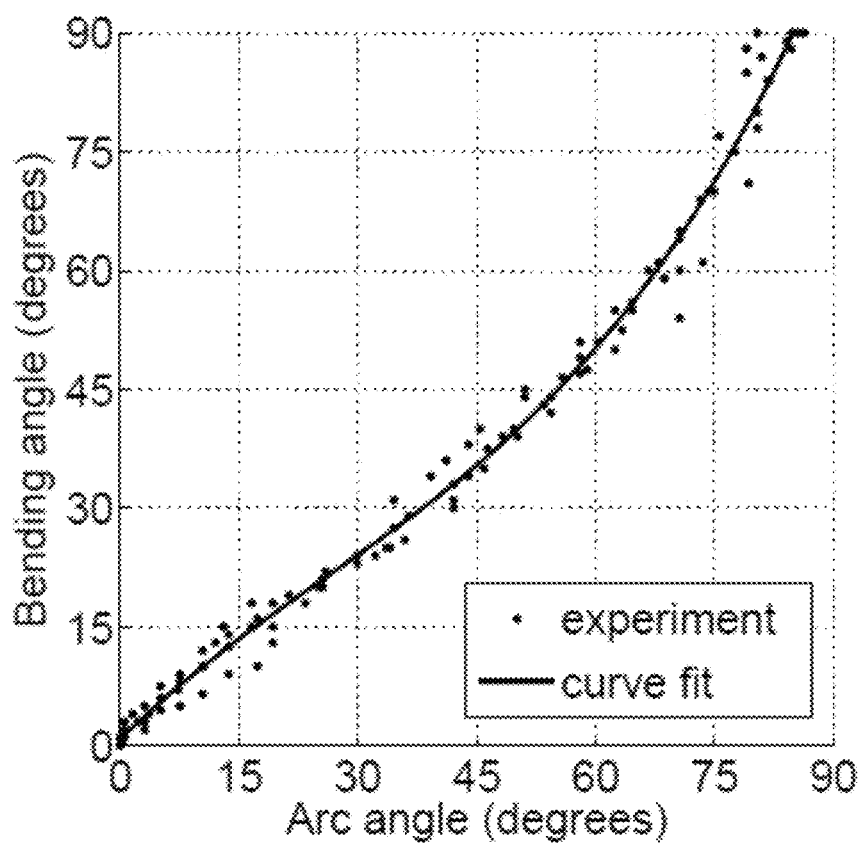

FIG. 22 depicts the relationship between the bending angle and the arc angle.

Figure 23:
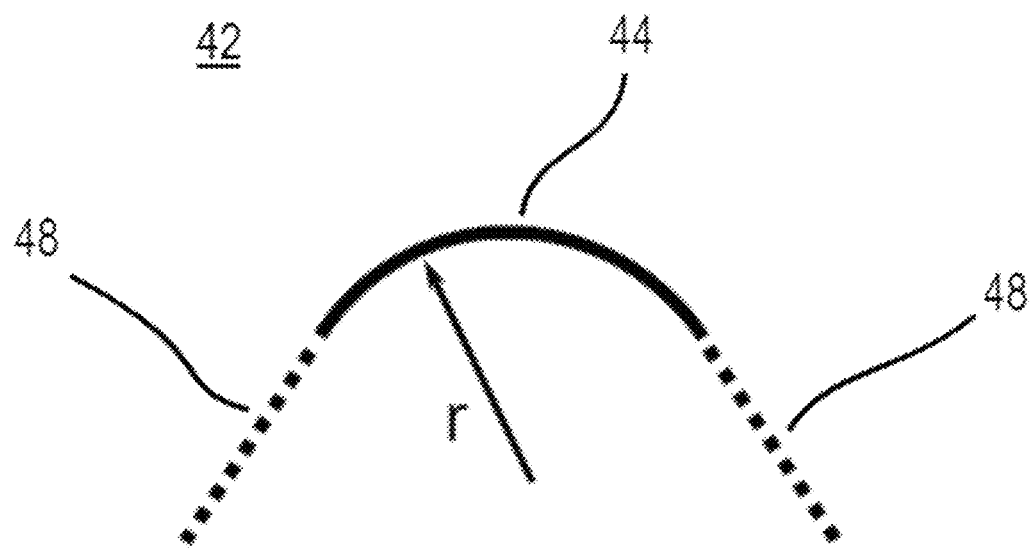

FIG. 23 depicts the SMA shape used in the exemplary prototype of Example 2.

Figure 24:
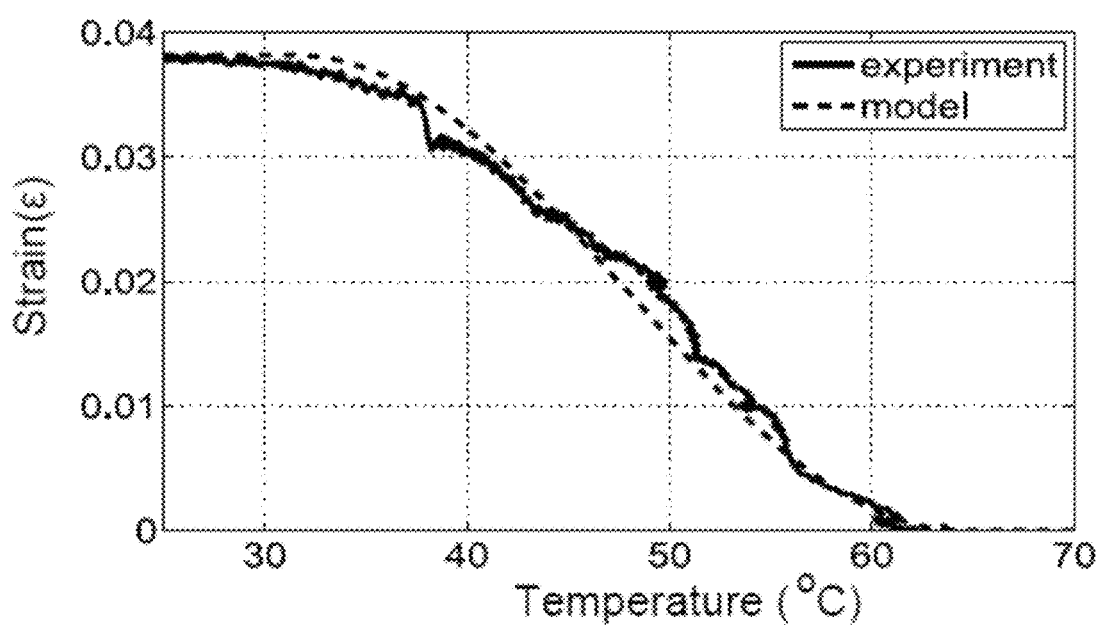

FIG. 24 depicts a strain vs. temperature relationship for a cannula.

FIGS. 25-38 are associated with Example 4, as described herein.

Figure 25:
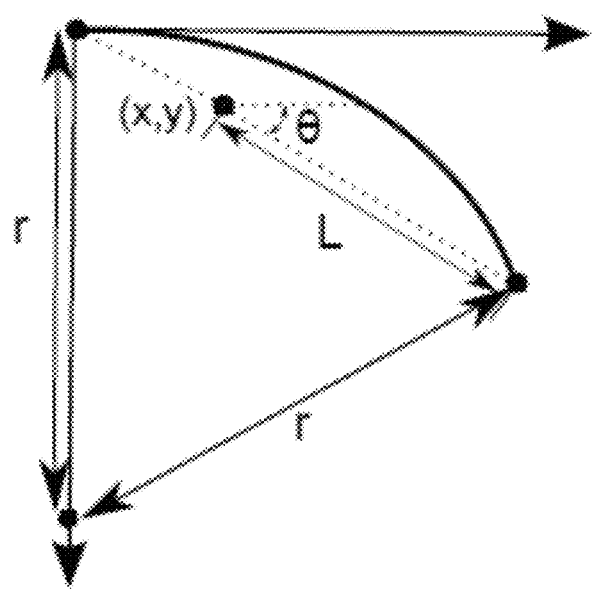

FIG. 25 depicts the geometry of the experimental setup described in Example 4.

Figure 26:
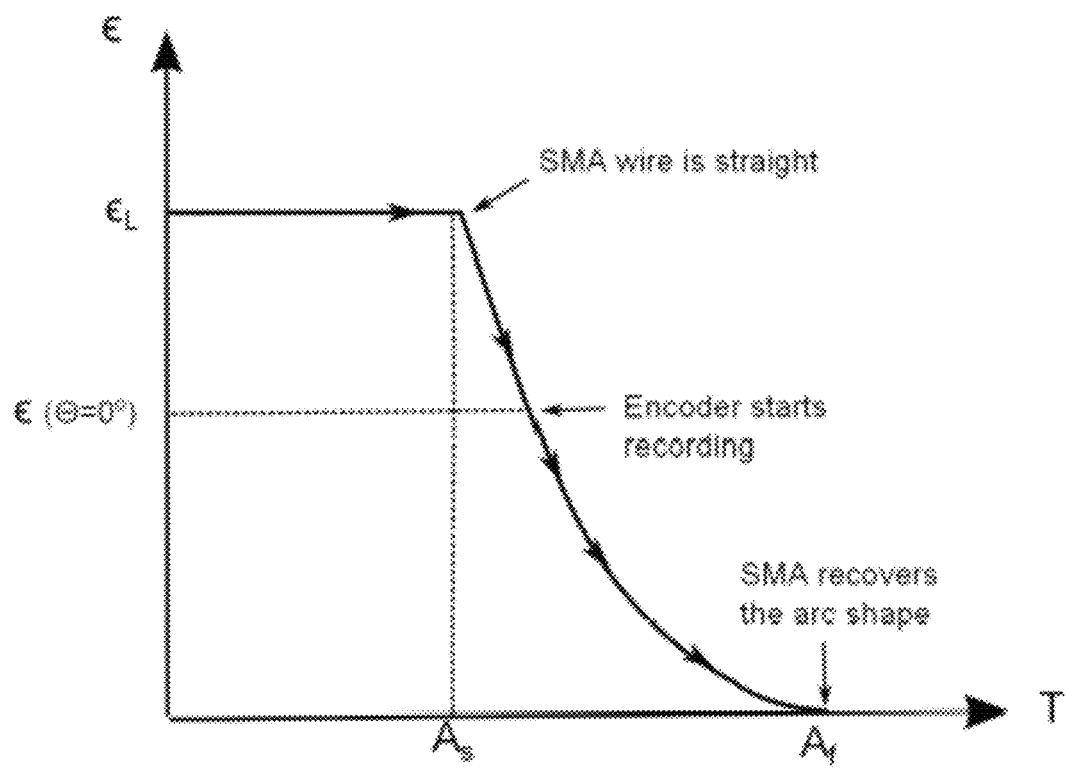

FIG. 26 depicts a diagram of strain vs. temperature for an exemplary SMA actuator.

Figure 27:
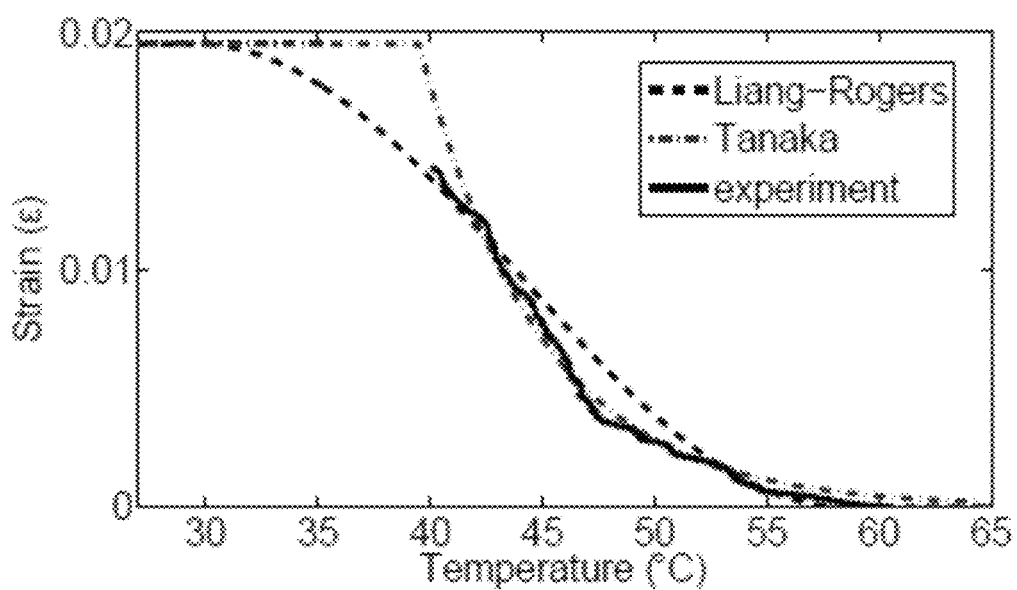

FIG. 27 depicts a change of strain with temperature observed in the experiment. Tanaka's model used an exponential expression for the martensite volume fraction, and the Liang-Rogers model used a cosine expression for the martensite volume fraction.

Figure 28:
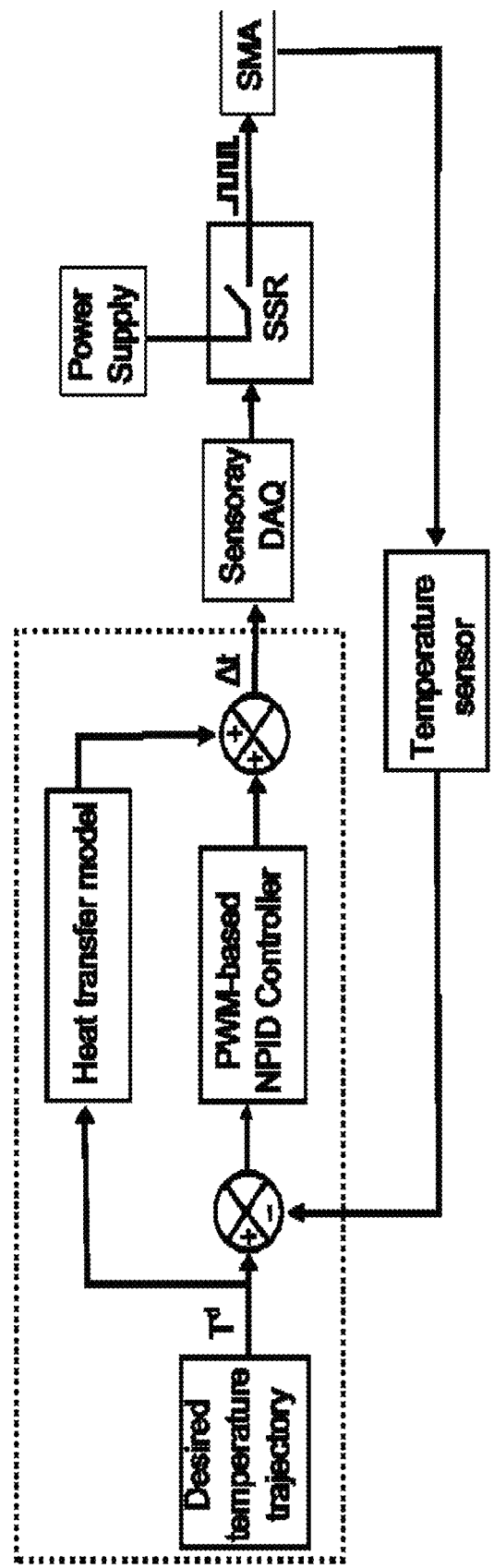

FIG. 28 depicts a block diagram of a proposed controller.

Figure 29:
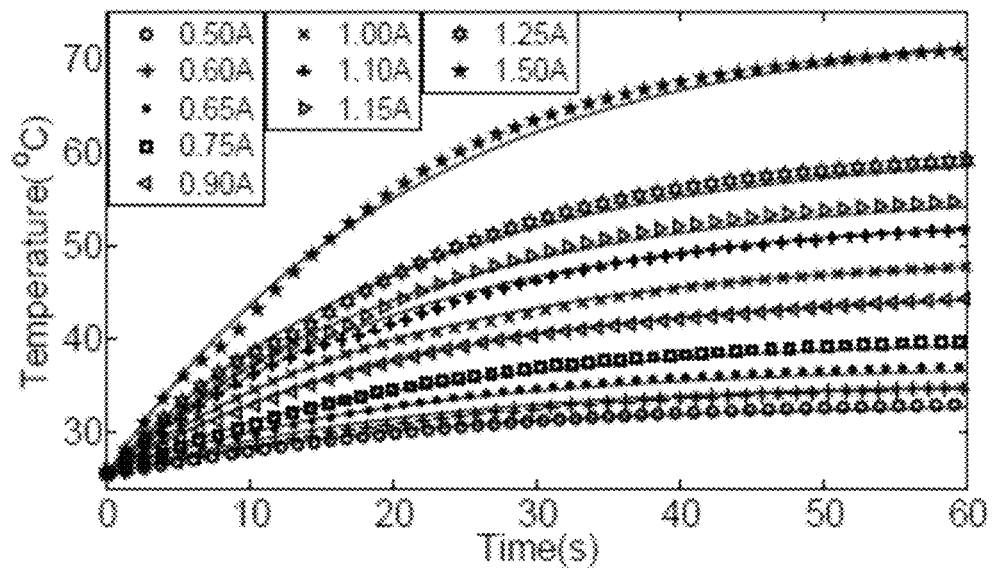

FIG. 29 depicts temperature profiles for different current inputs. Solid lines represent the temperature profiles obtained using the empirical model.

Figure 30:
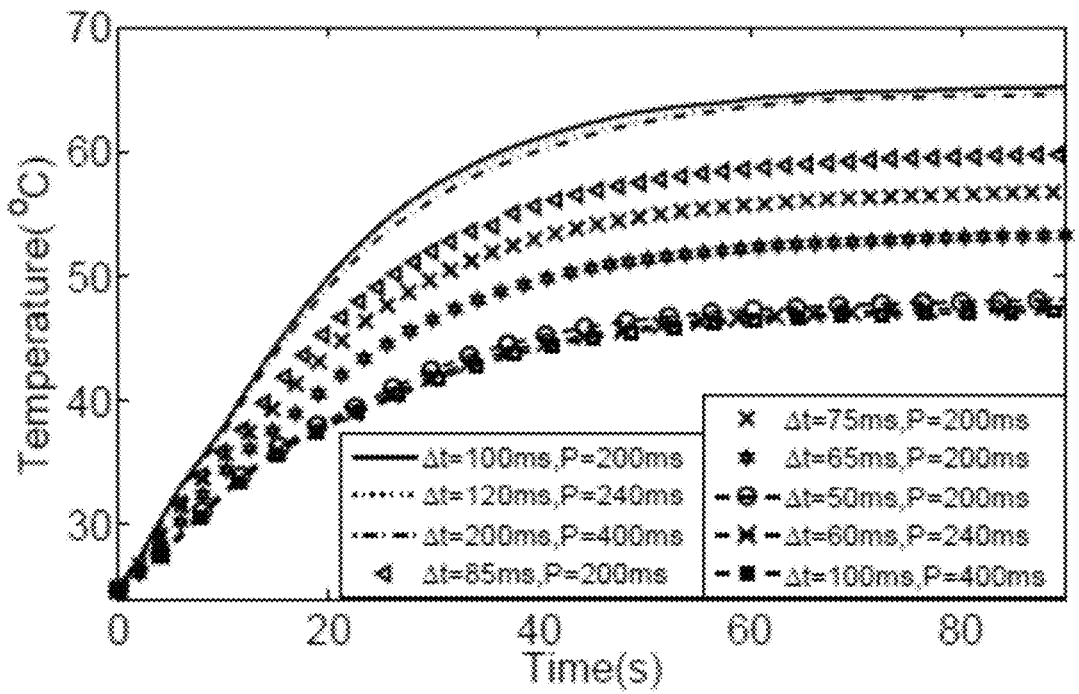

FIG. 30 depicts a comparison of different pulse widths and duty cycles.

Figure 31:
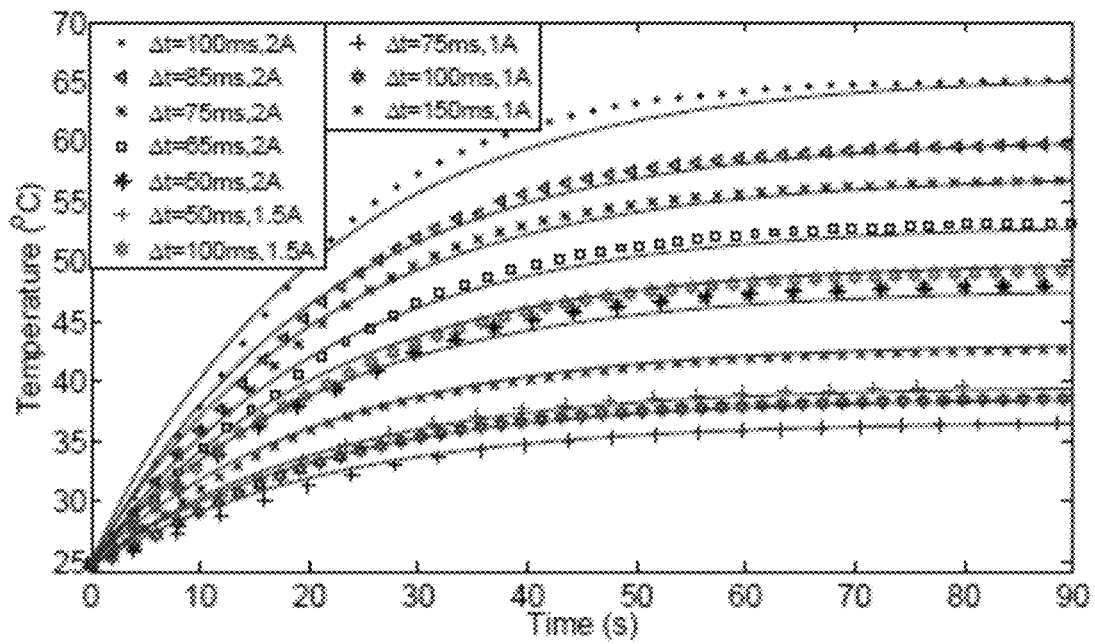

FIG. 31 depicts an experiment in which temperature profiles were obtained for different pulse width and current values for P=200 ms. Solid lines represent the temperature profiles obtained using the empirical model.

Figure 32:
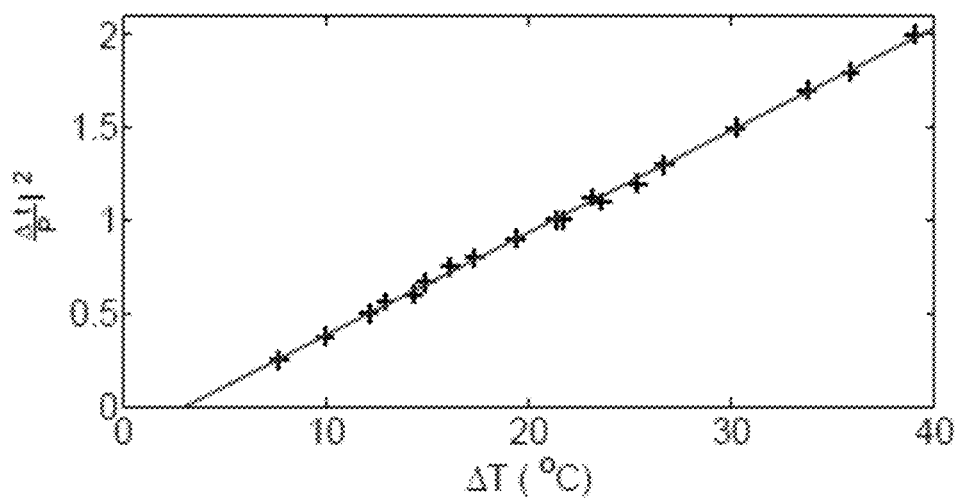

FIG. 32 depicts the change of the desired temperature increase with the PWM input parameter.

Figure 33:
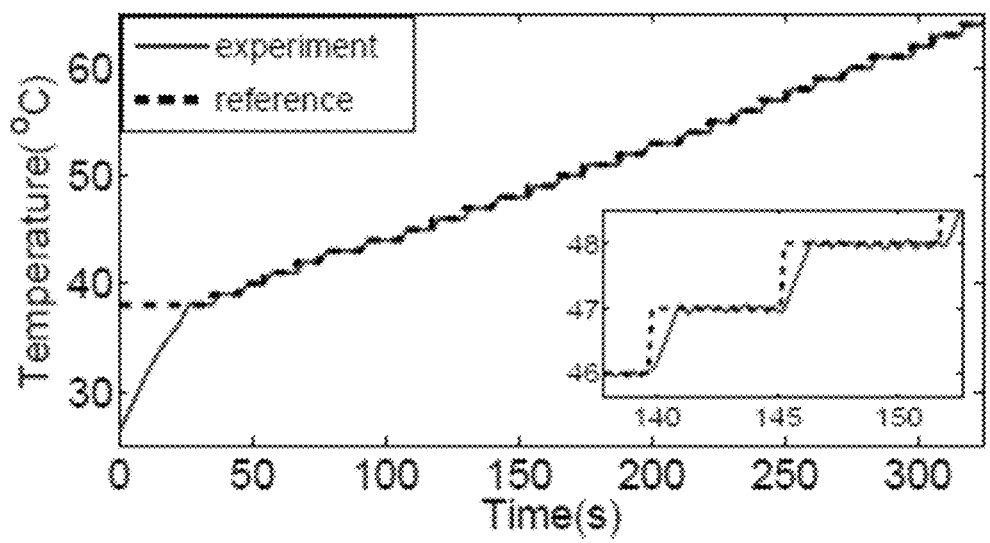

FIG. 33 depicts step-wise temperature references and the temperature change of the SMA.

Figure 34:
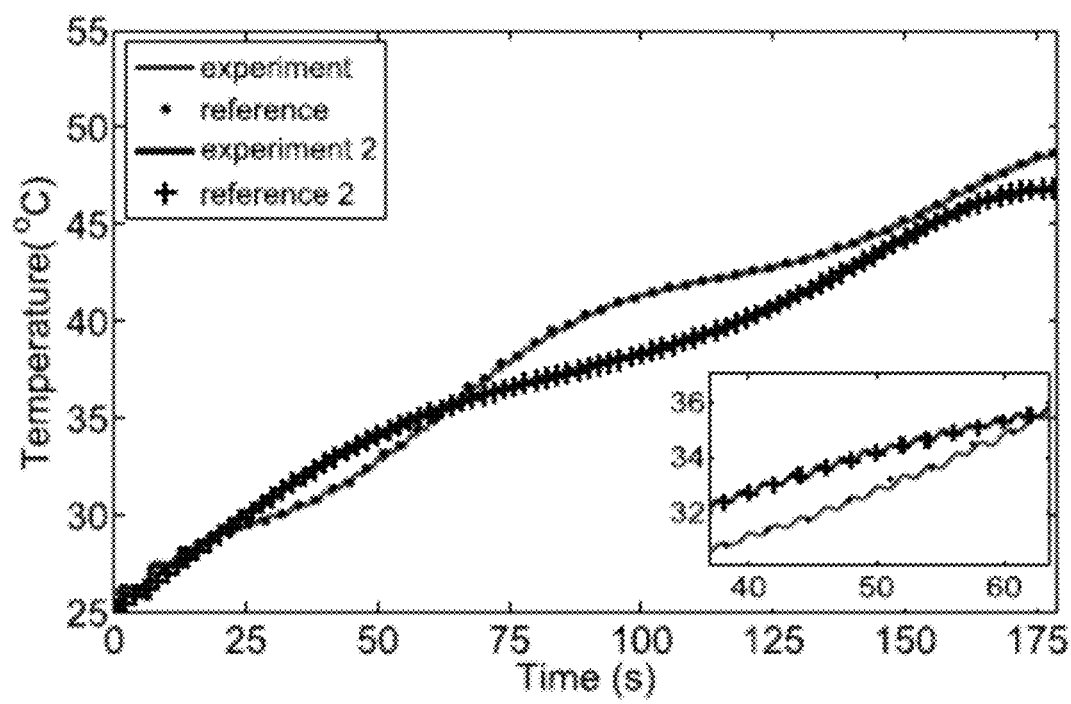

FIG. 34 depicts continuous polynomial references and the temperature change of the SMA.

Figure 35:
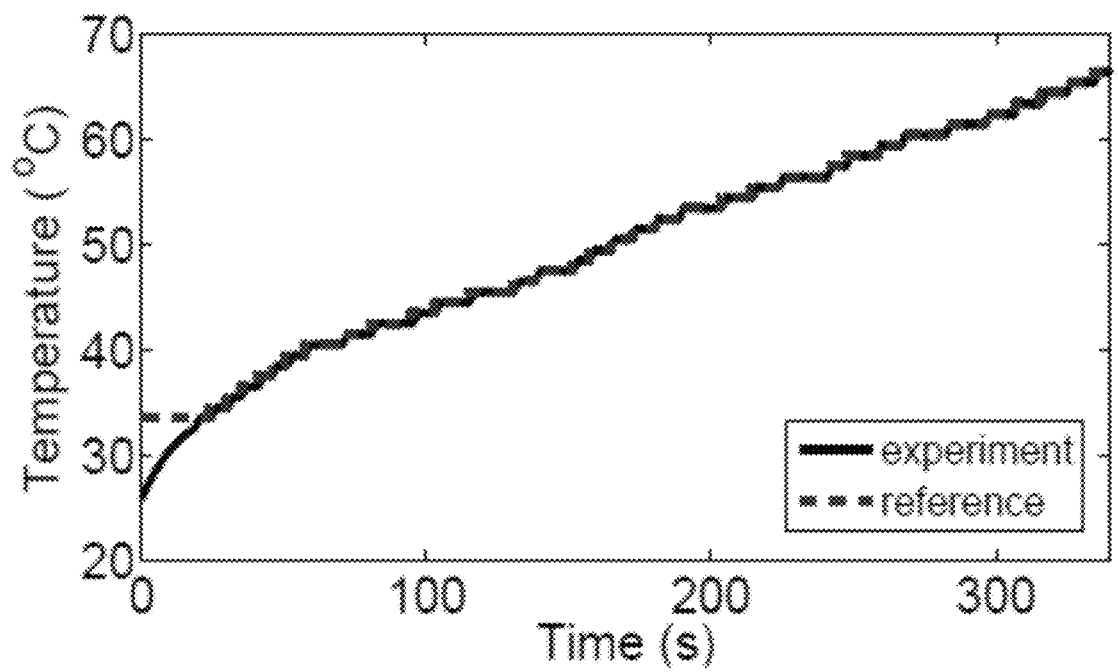

FIG. 35 depicts step-wise reference temperature and the change in temperature of the SMA.

Figure 36:
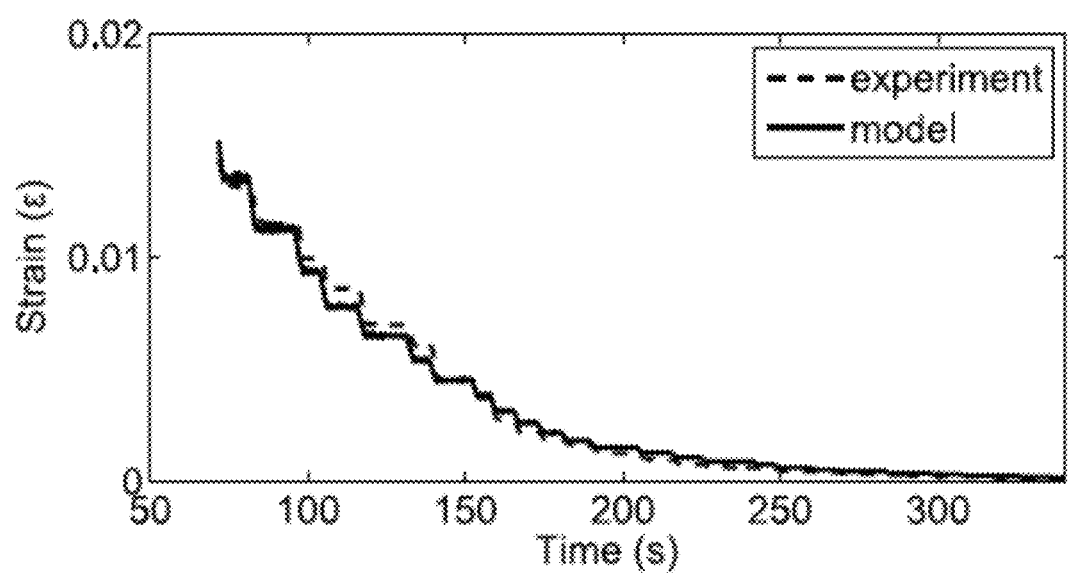

FIG. 36 depicts the change in strain in the SMA and the strain predicted by the model for a step-wise temperature reference.

Figure 37:
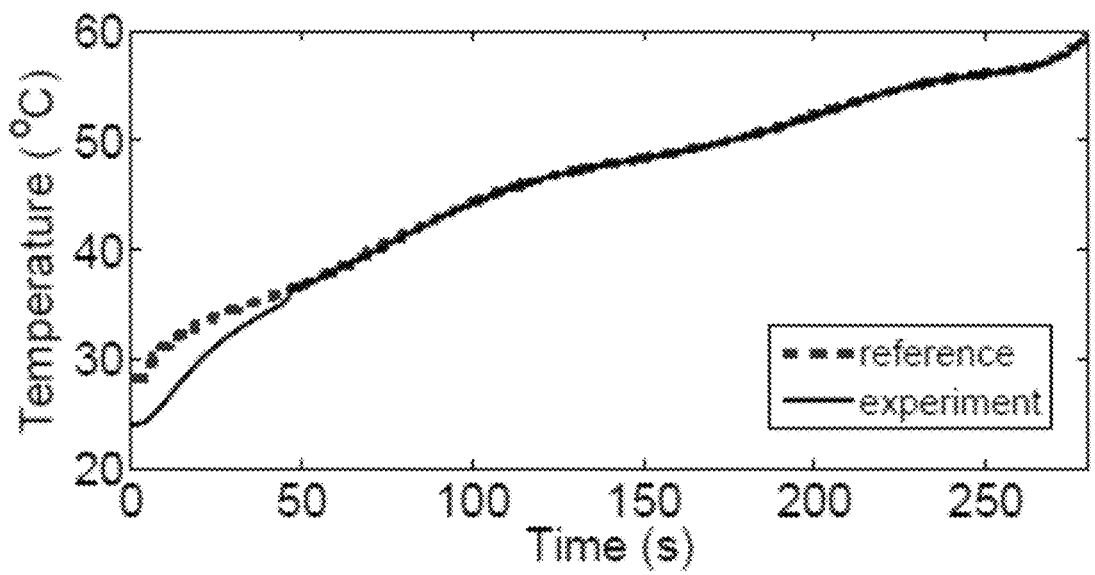

FIG. 37 depicts a continuous temperature reference and the change in temperature of the SMA.

Figure 38:
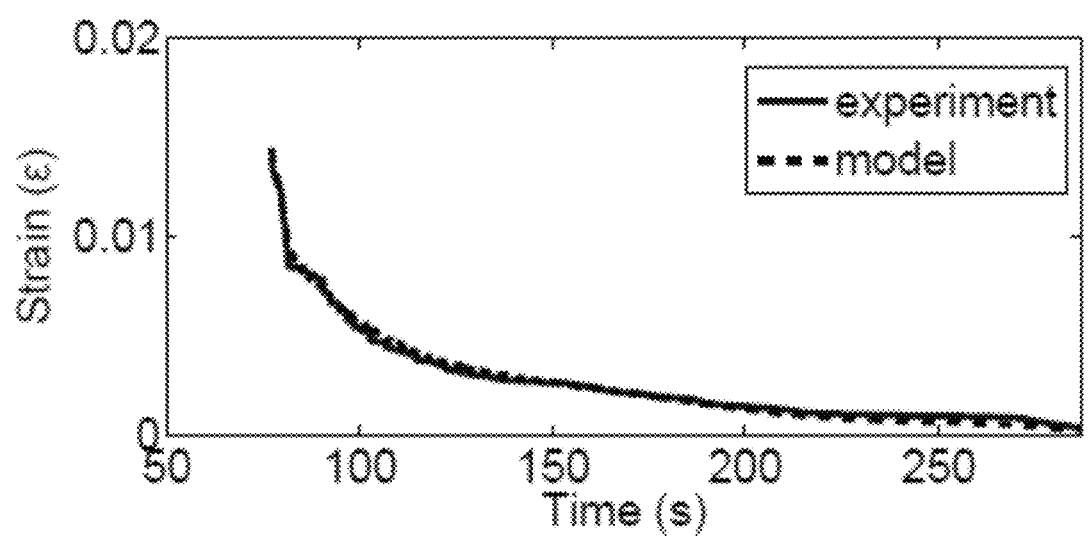

FIG. 38 depicts the change in strain of the SMA and the strain predicted by the model for a continuous temperature reference.

FIGS. 39-57 are associated with Example Five, as described herein.

Figure 39:
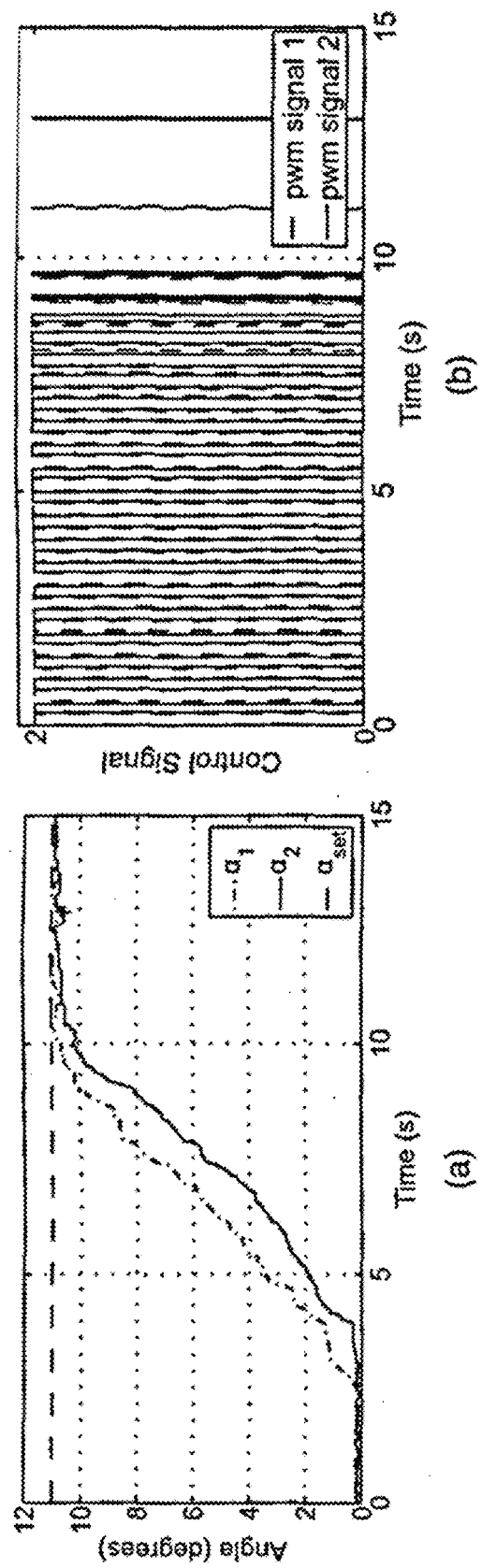

FIG. 39 depicts (a) bending angle vs. time for the cannula, and (b) PWM command signals for the two SMA wires.

Figure 40:
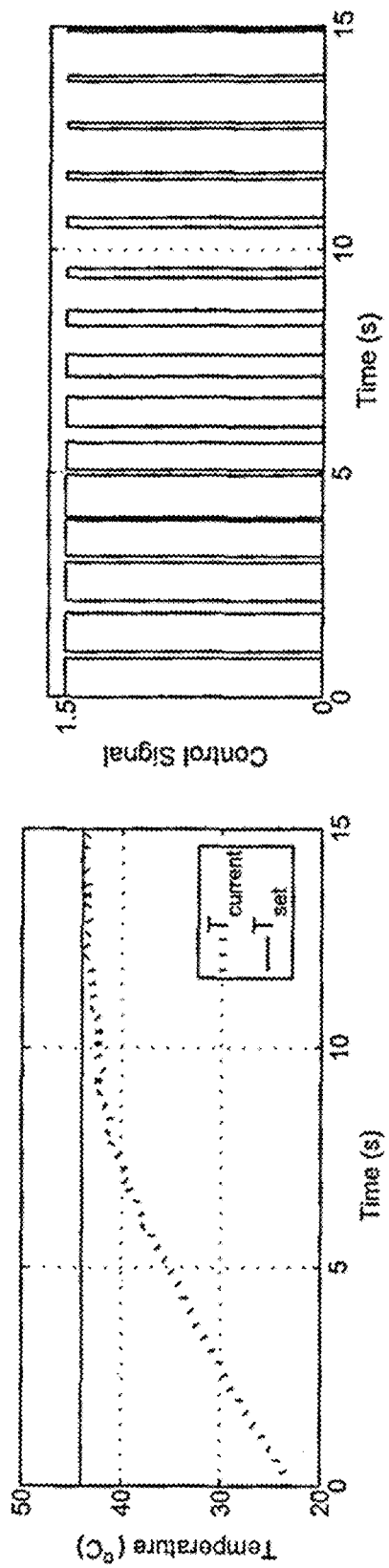

FIG. 40 depicts (a) temperature vs. time for the first joint, and (b) PWM command signal.

Figure 41:
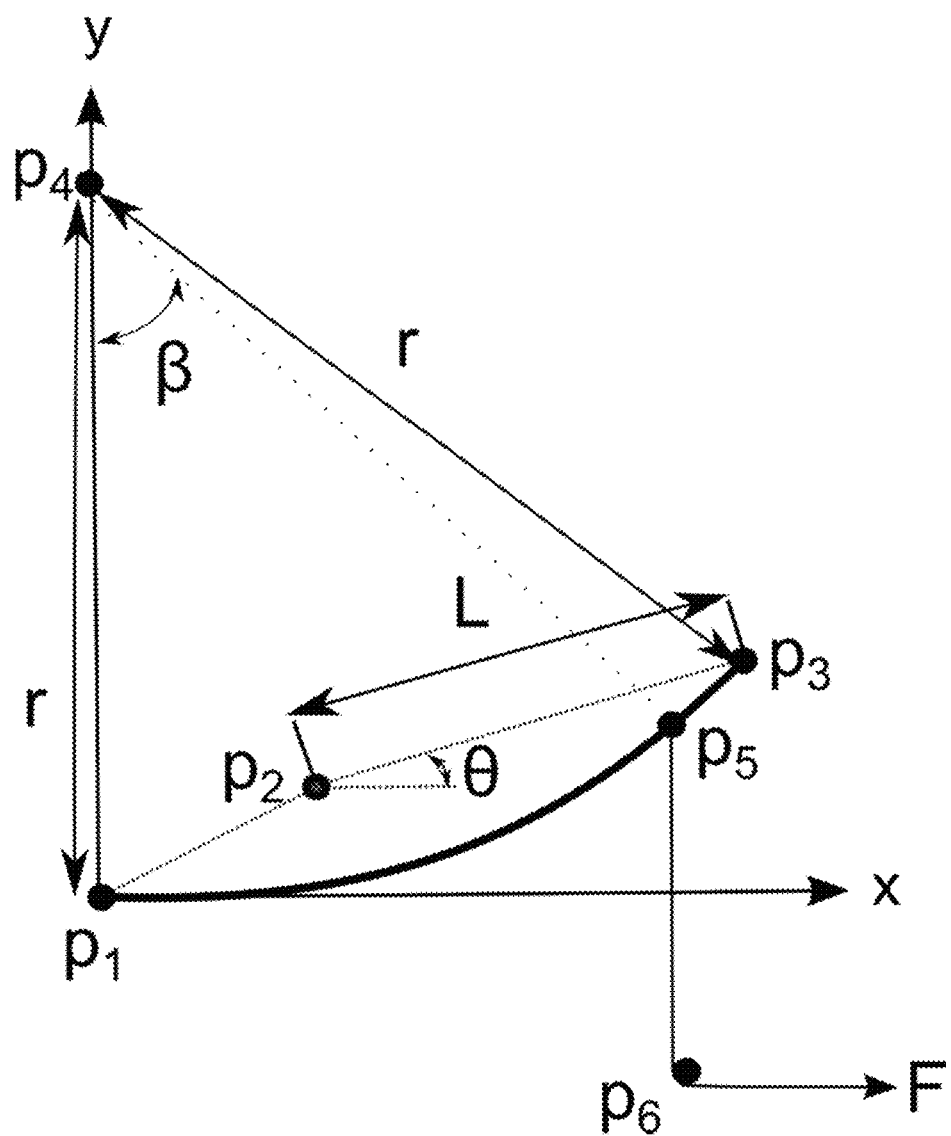

FIG. 41 depicts the geometric relations of the experimental setup described in Example 5.

Figure 42:
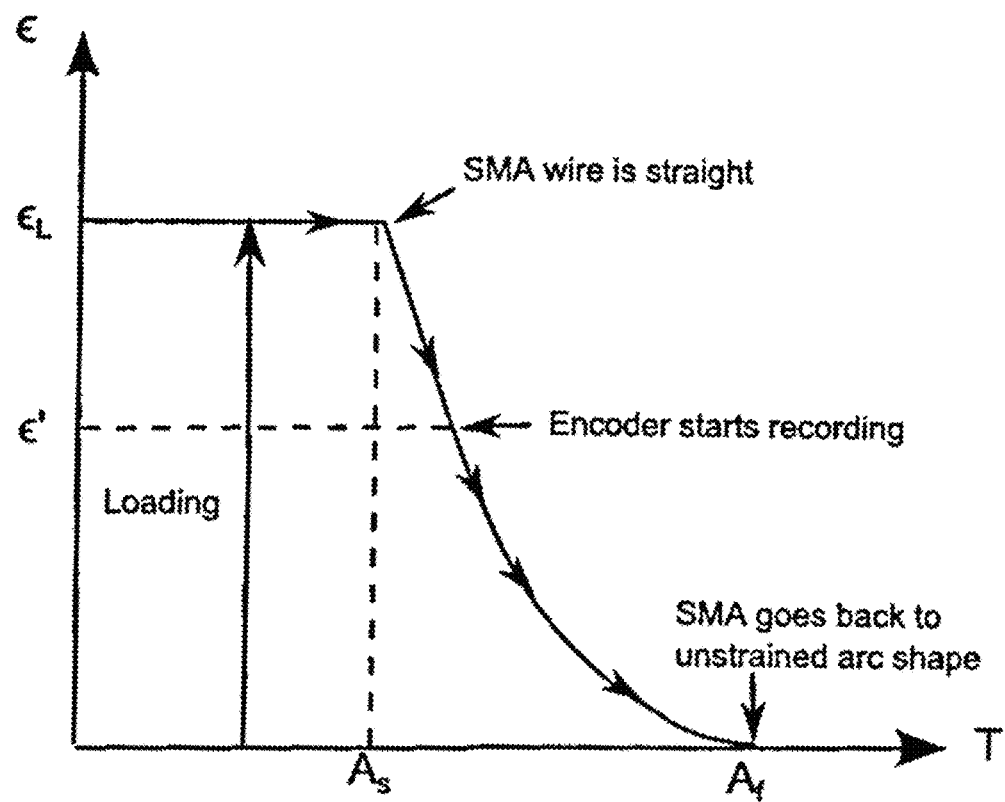

FIG. 42 depicts a diagram of strain vs. temperature for an SMA actuator.

Figure 43:
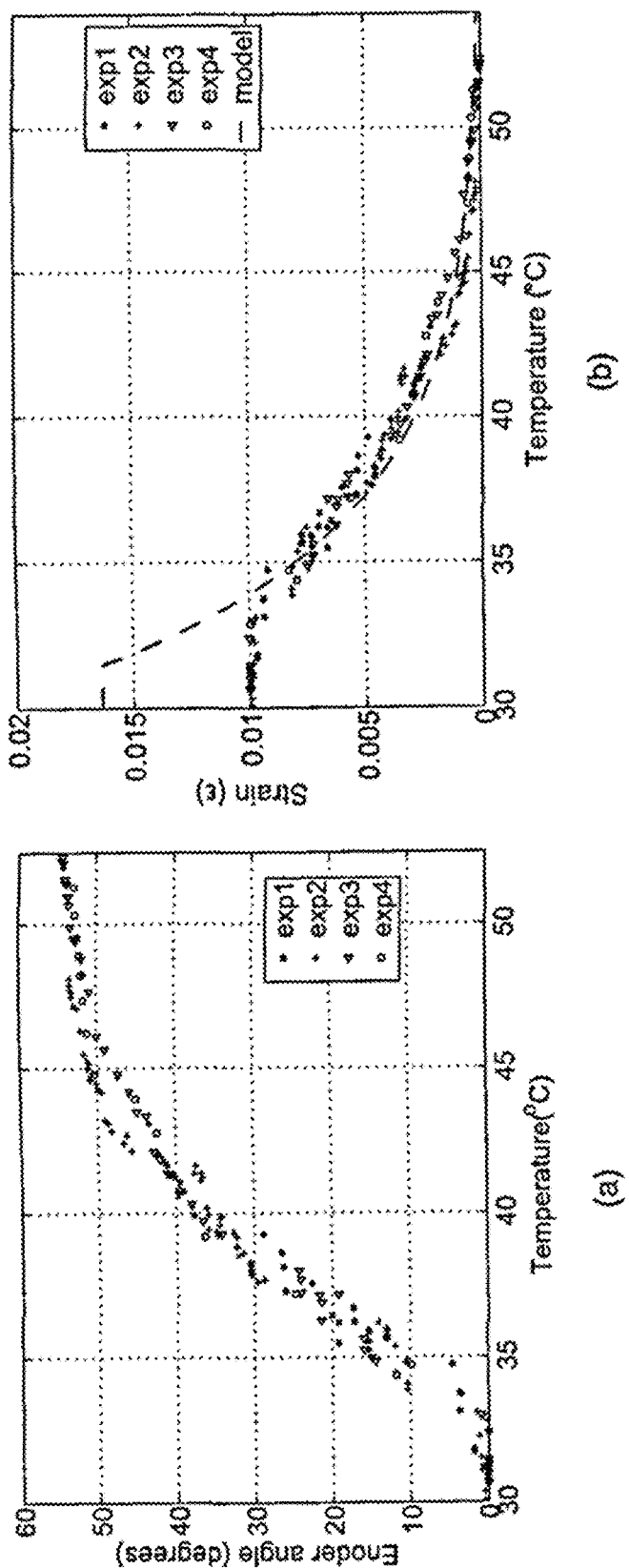

FIG. 43 depicts (a) encoder readings, and (b) strain vs. temperature under no loading.

Figure 44:
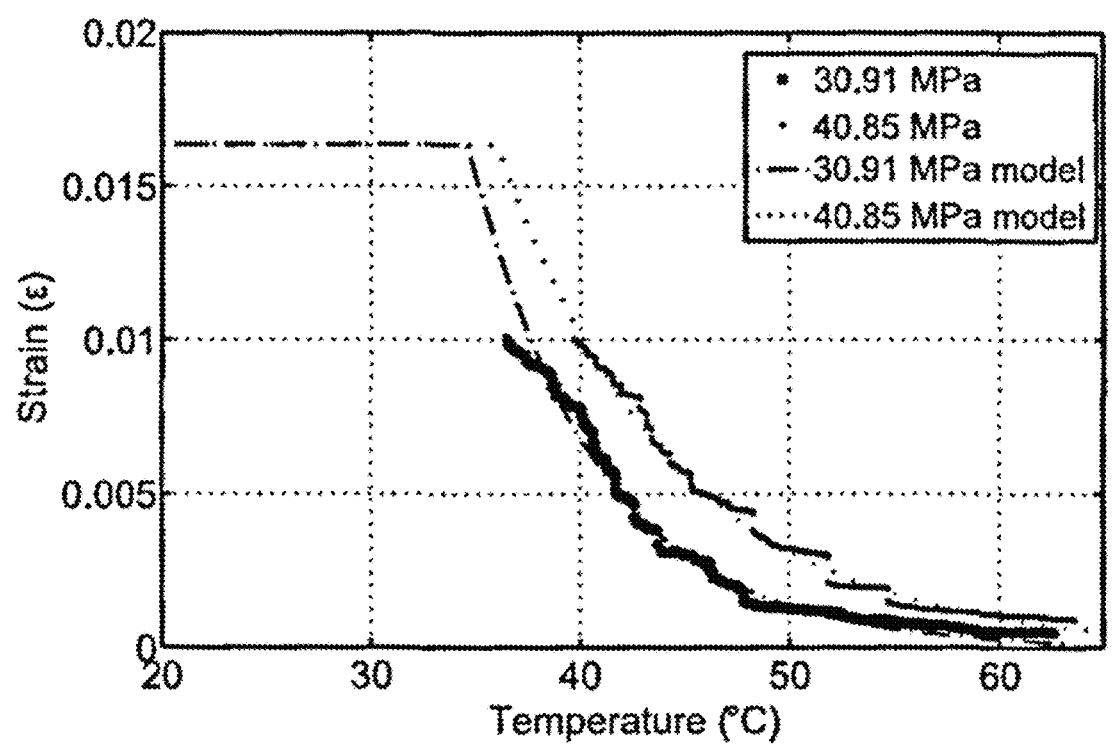

FIG. 44 depicts strain vs. temperature under external loading.

Figure 45:
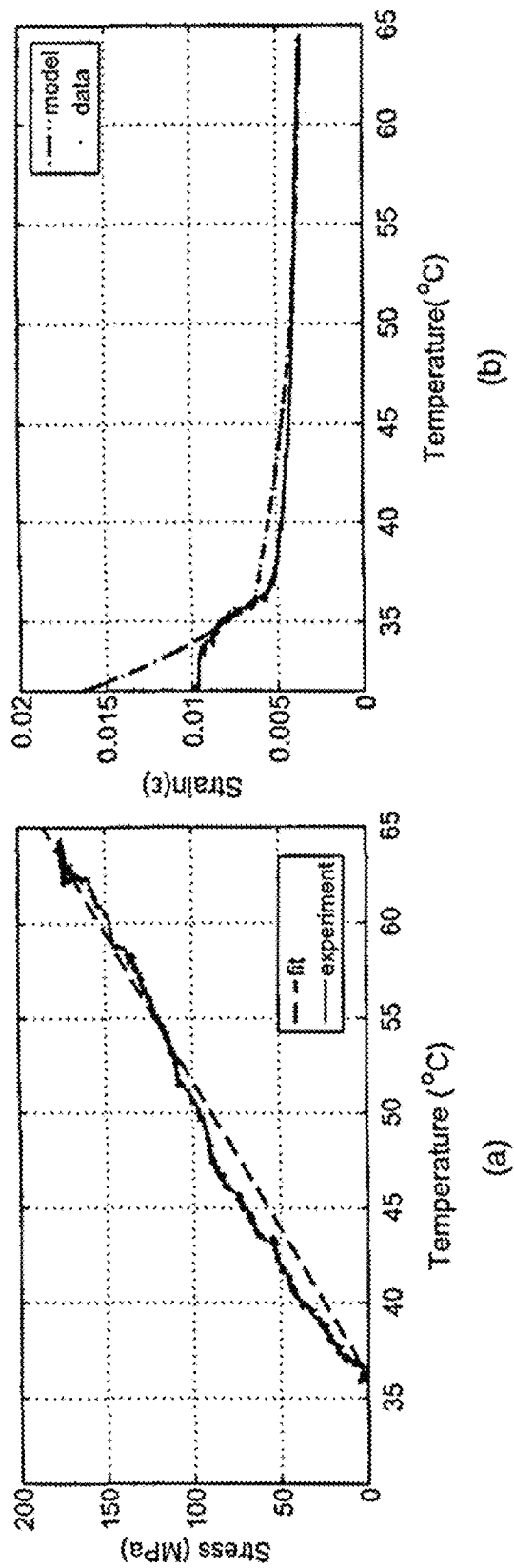

FIG. 45 depicts (a) external stress acting on the SMA wire, and (b) strain-temperature relation under variable loading.

Figure 46:
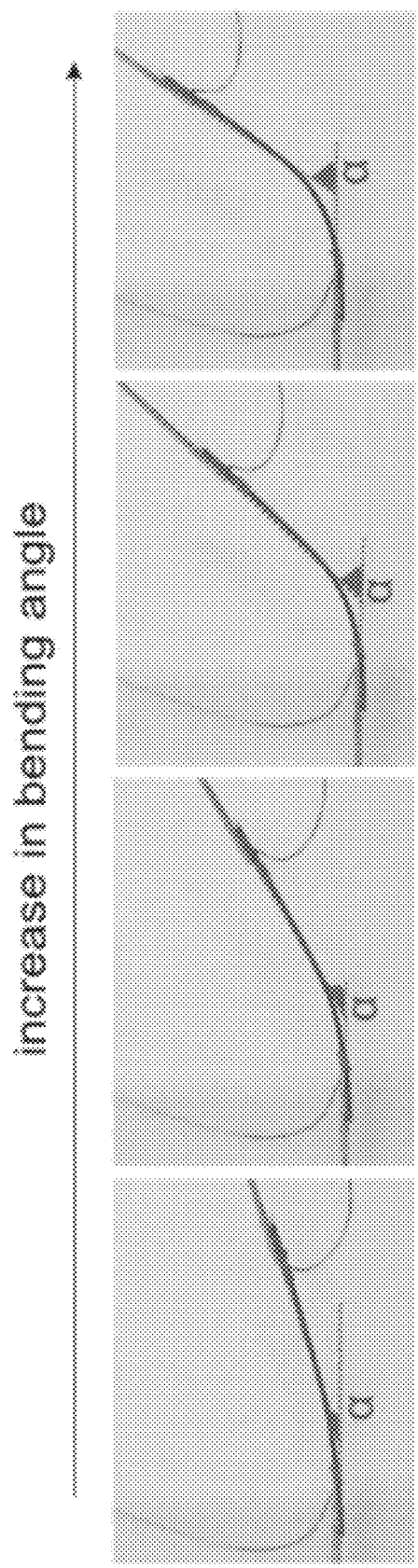

FIG. 46 depicts the change in bending angle as SMA wire is heated.

Figure 47:
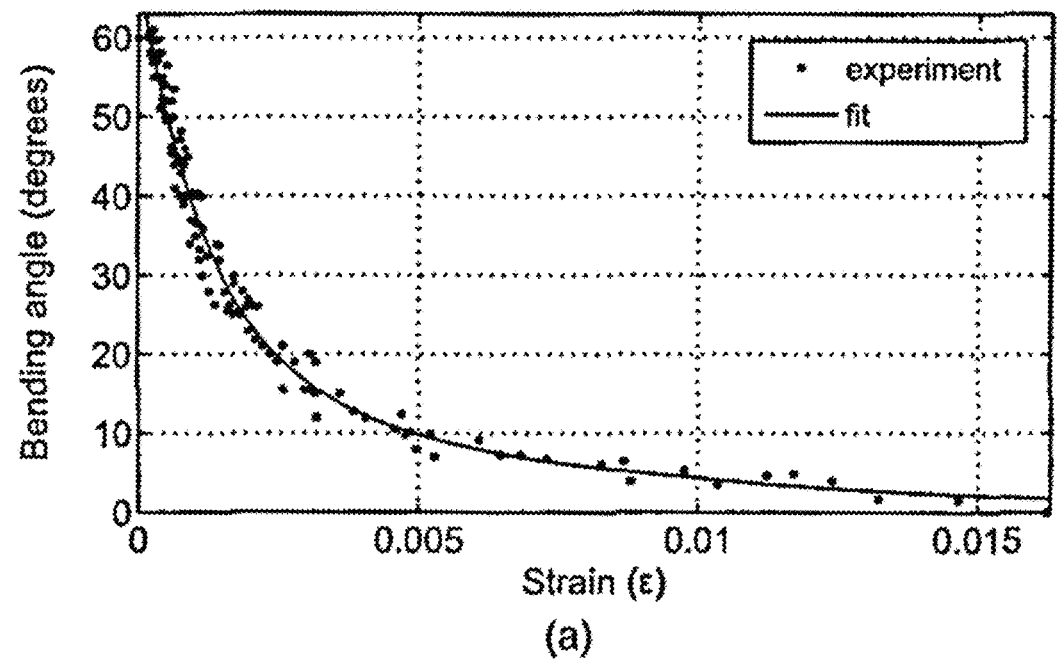
Figure 47:
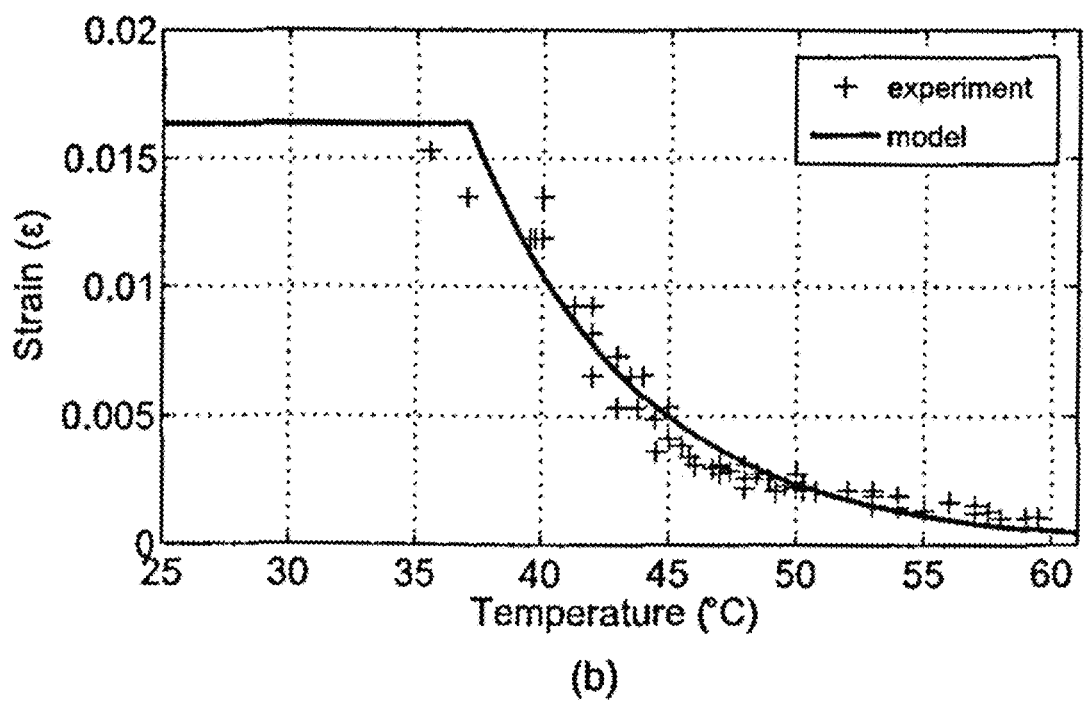

FIG. 47 depicts (a) relation between bending angle and strain, and (b) the relationship between strain and temperature for the cannula.

Figure 48:
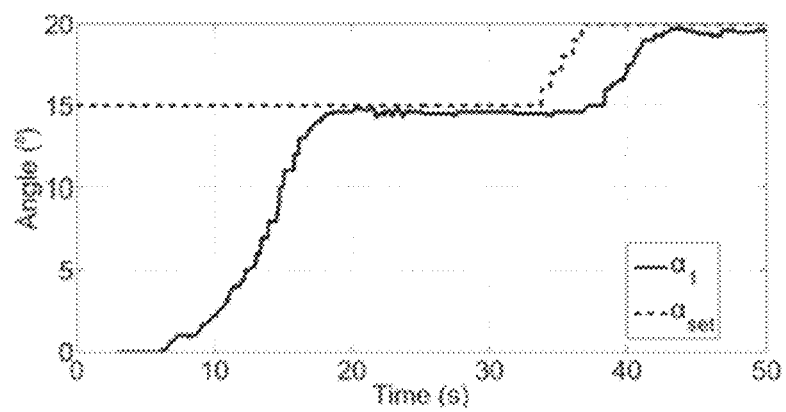
Figure 48:
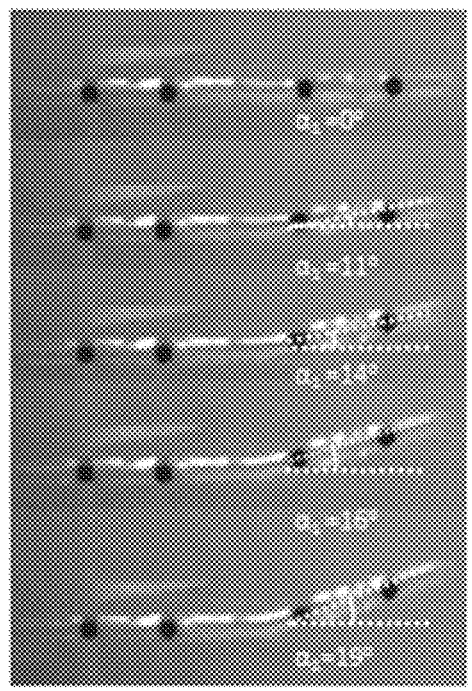

FIG. 48 depicts (a) change of bending angle with time inside translucent gelatin, and (b) the cannula moving inside the gelatin.

Figure 49:
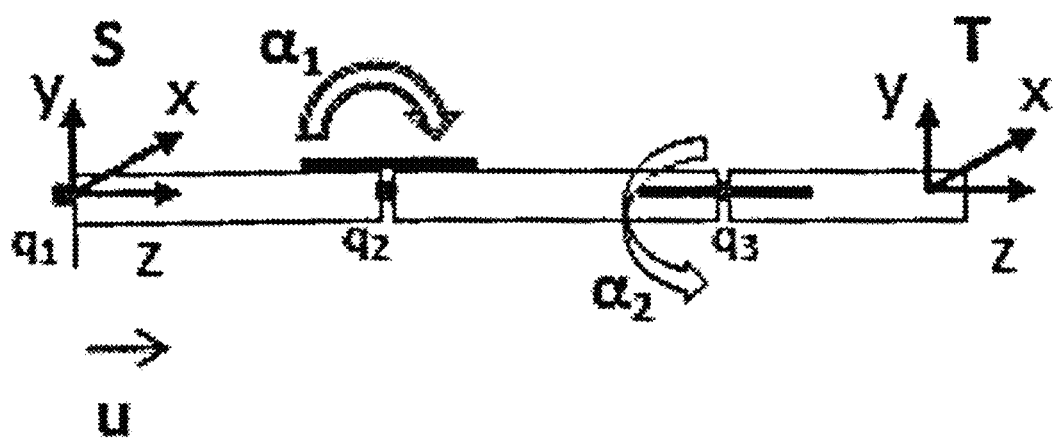

FIG. 49 depicts a schematic used for the forward kinematics map.

Figure 50:
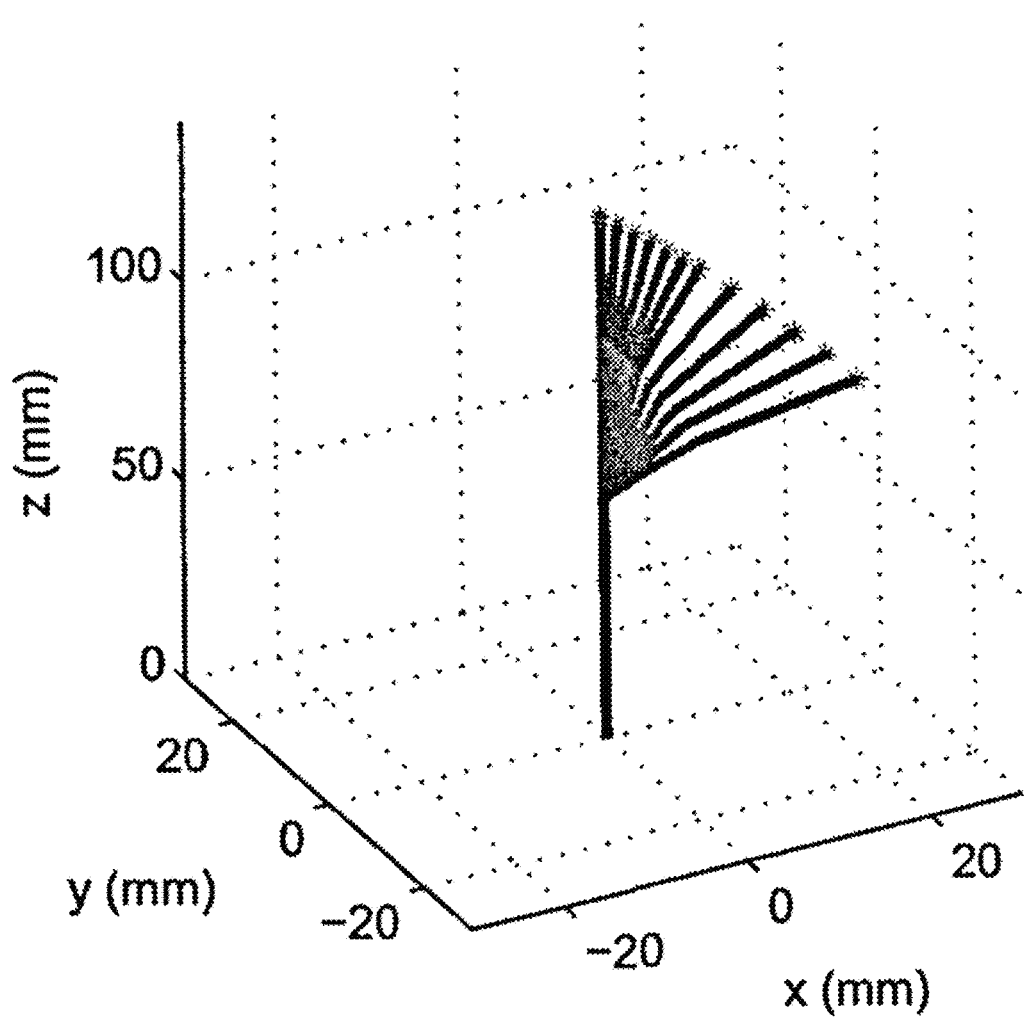

FIG. 50 depicts motion of an SMA wire in 3D.

Figure 51:
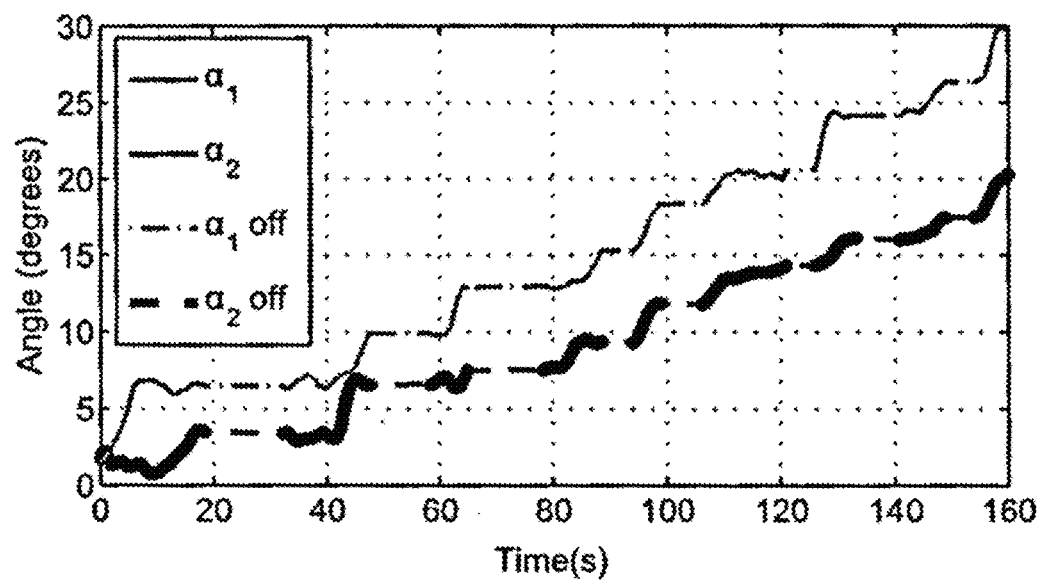

FIG. 51 depicts the change of joint angle with time.

Figure 52:
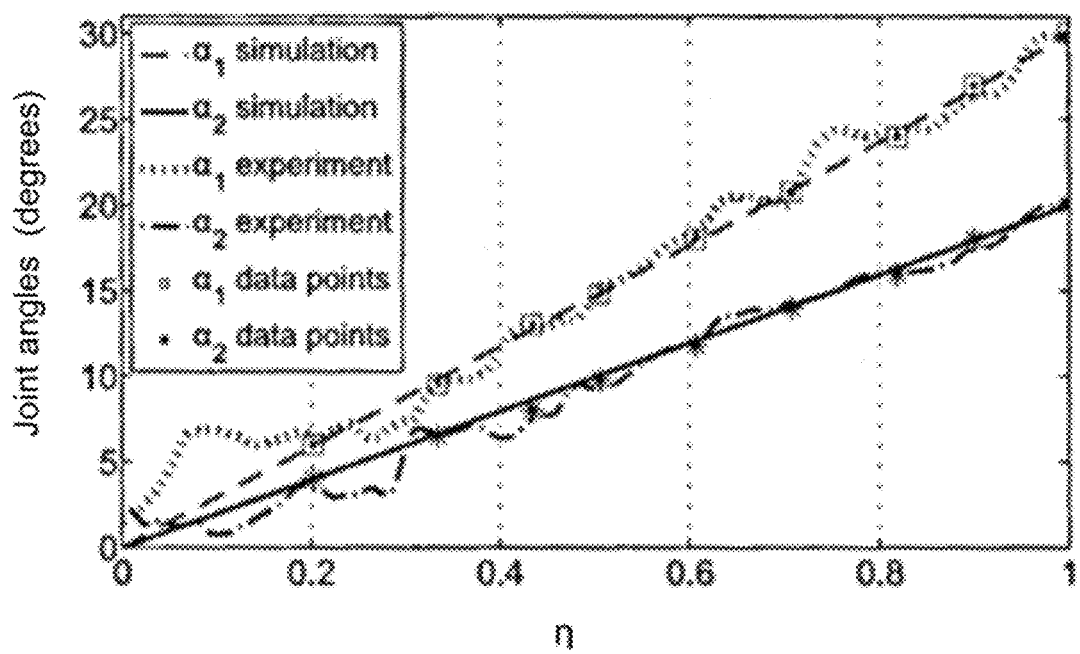

FIG. 52 depicts the change of join angle with $\eta$.

Figure 53:
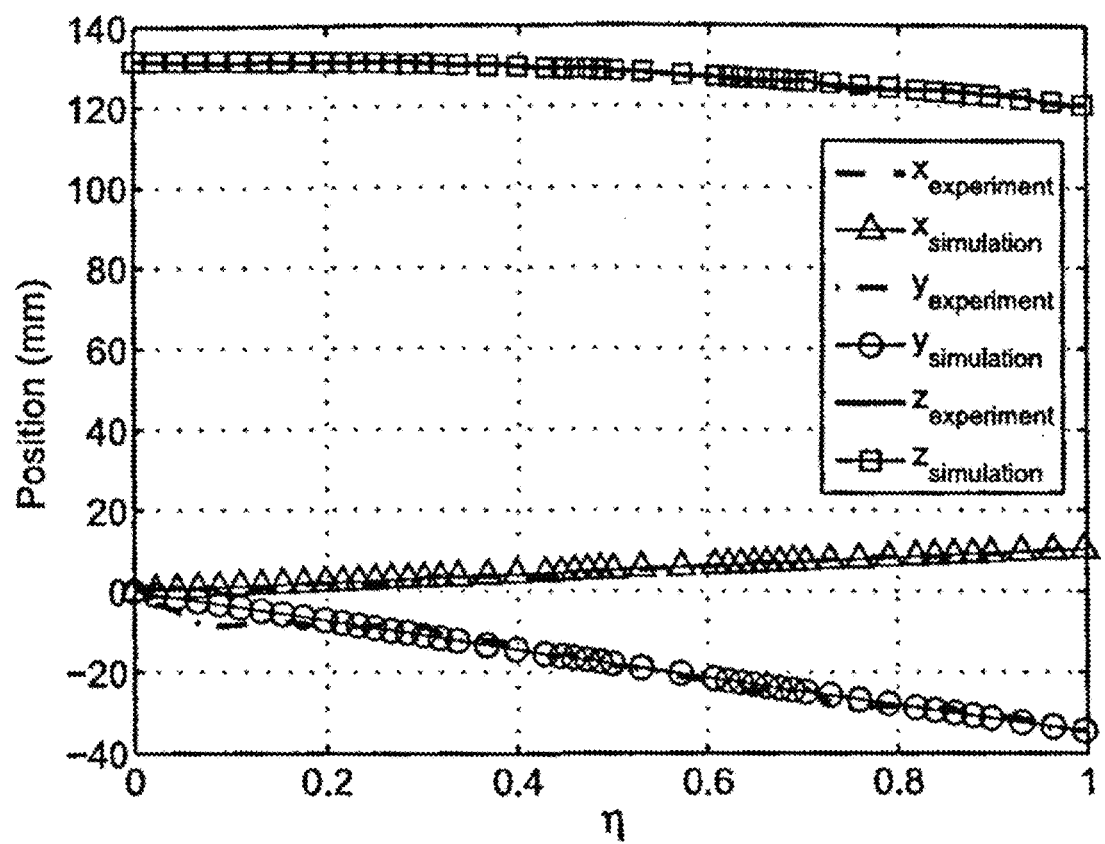

FIG. 53 depicts the change of 3D position with $\eta$.

Figure 54:
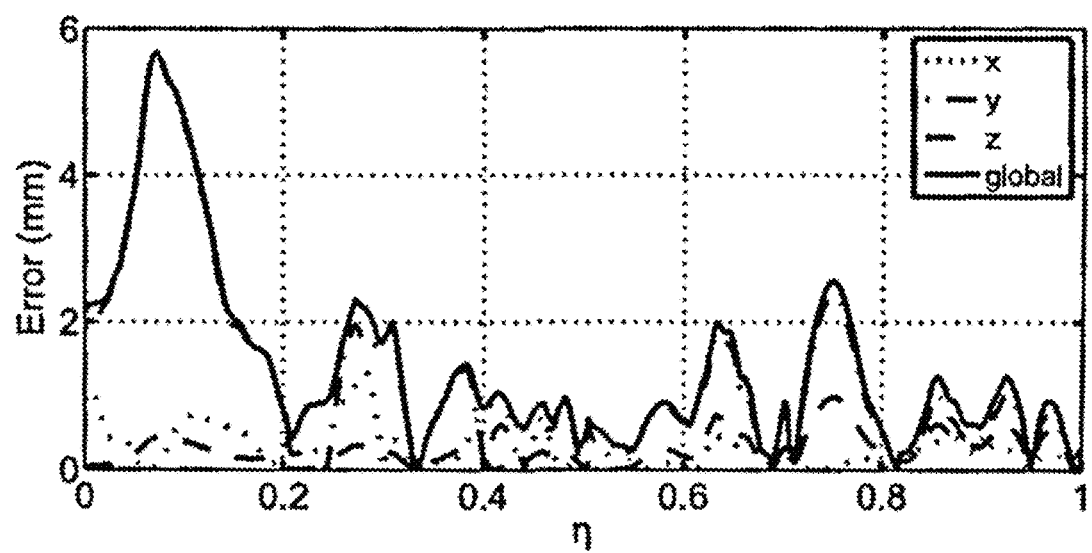

FIG. 54 depicts the position errors of the cannula tip along the trajectory defined by the parameter $\eta$.

Figure 55:
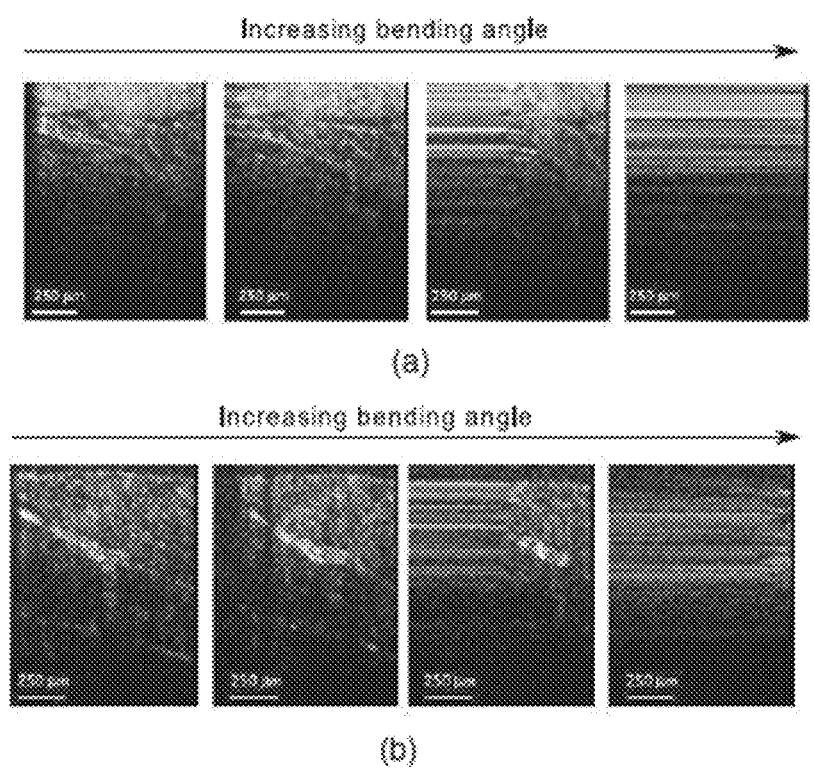

FIG. 55 depicts (a) microstructures of chicken breast, and (b) microstructures of porcine tissue.

Figure 56:
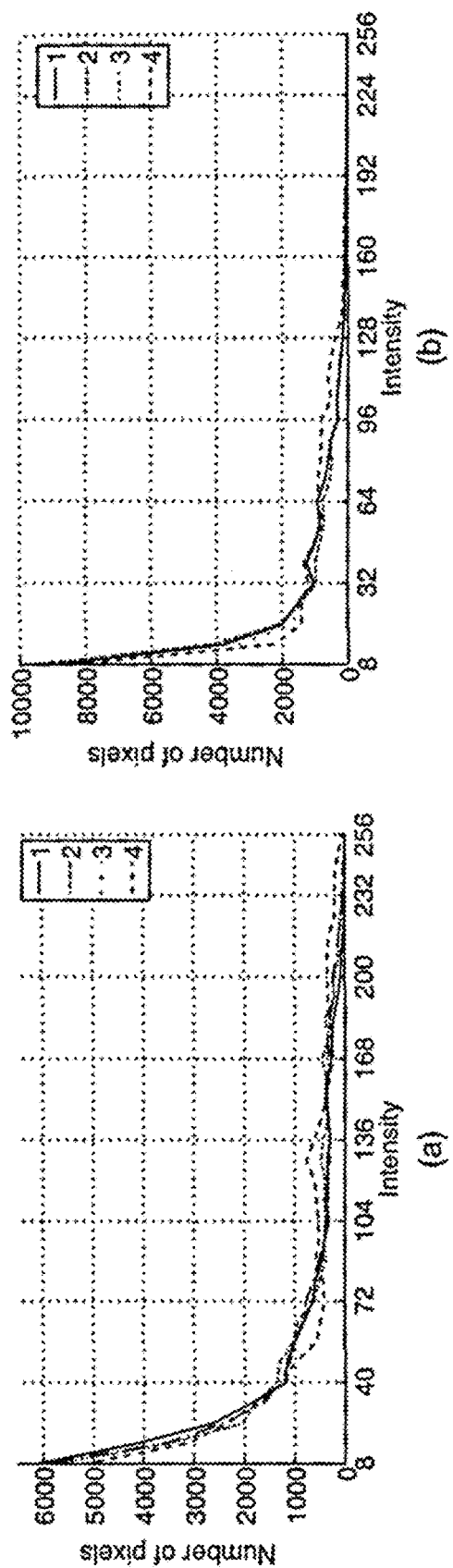

FIG. 56 depicts (a) histogram of chicken breast OCT images, and (b) histogram of porcine tissue OCT images.

Figure 57:
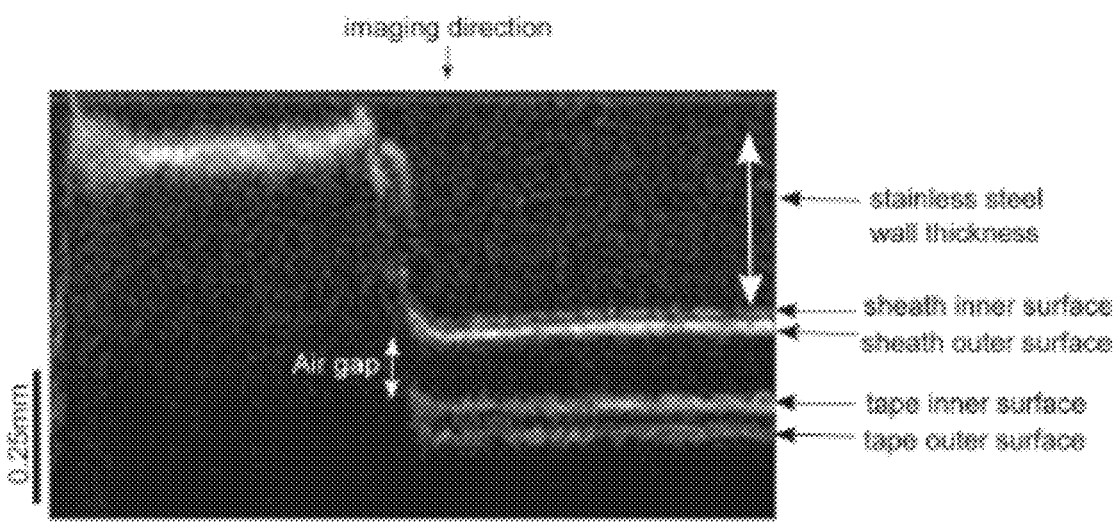

FIG. 57 depicts the inner wall of the cannula, sheath, and tape.

Figure 58:
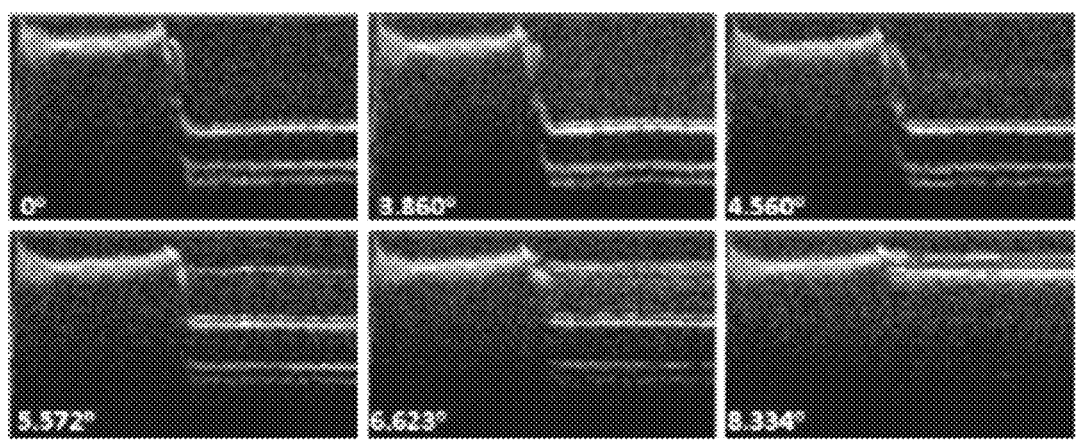

FIG. 58 depicts OCT images at various angles.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents.

It is understood that the disclosed devices, methods, and compositions are not limited to the particular methodology, protocols, and reagents described, as these may vary. It is also to be understood that the terminology used herein is for the purpose of describing particular aspects only and is not intended to limit the scope of the present invention which will be limited only by the appended claims.

As used throughout, the singular forms "a," "an" and "the" include plural referents unless the context clearly dictates otherwise. Thus, for example, reference to "a consumable rod" can include two or more such consumable rods unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, the term "probe" is understood to include needles, cannulas, and other instruments that are conventionally inserted and guided within the body of a subject during a percutaneous and/or intravascular therapeutic or diagnostic procedure. The cannulas disclosed and described in the examples section of this application are provided as representative, non-limiting examples of the probes disclosed herein.

As used herein, the term "high-power-density actuator" generally refers to materials that have a compact size and shape but are capable of generating relatively large forces when actuated. Examples of high-power-density actuators include, for example and without limitation, shape memory alloys (SMAs), piezoelectric actuators, cable actuators, and electroactive polymers as are known in the art.

Disclosed herein, with reference to FIGS. 1-6, is a steerable probe 10. In exemplary aspects, the steerable probe 10 can be configured for use in a medical procedure. However, it is contemplated that the probe 10 can be used in any application where a selectively actuated steerable probe is needed. In exemplary aspects, it is contemplated that the steerable probe 10 can be used in a percutaneous and/or intravascular medical procedure, such as, for example and without limitation, prostate biopsy, breast biopsy, radiofrequency ablation (RFA), prostate brachytherapy, liver tumor ablation, Natural Orifice Translumenal Endoscopic Surgery (NOTES), and the like. In one aspect, the probe 10 can have a central axis 12, a first end 14, and an opposed second end 16. In this aspect, it is contemplated that the probe 10 can have a length 11 corresponding to the distance between the first end 14 and the second end 16.

In another aspect, and with reference to FIGS. 1-5, the probe 10 can comprise a plurality of spaced segments 20. In this aspect, each segment 20 of the plurality of spaced segments can have a wall 22 with an inner surface 24 and an outer surface 26. The inner surface 24 of each segment 20 can define a respective central bore 25 that surrounds the central axis 12 of the probe 10. It is contemplated that the central bores 25 of the plurality of spaced segments 20 can cooperate to define an inner channel 18 of the probe 10. In exemplary aspects, the inner channel 18 of the probe 10 can be configured to receive at least one of a diagnostic tool and a therapeutic tool such as, for example and without limitation, an ultrasound probe, an optical coherence tomography (OCT) imaging probe, an RFA probe, and the like.

In a further aspect, the probe 10 can comprise at least one joint assembly 40. In this aspect, each joint assembly 40 of the at least one joint assembly 40 can comprise at least one high-power-density actuator 42. In an additional aspect, each actuator 42 of the at least one actuator can be secured to adjacent segments 20 of the plurality of spaced segments such that each segment of the plurality of spaced segments is operatively coupled to an adjacent segment of the plurality of spaced segments. In a further aspect, each actuator 42 of the at least one actuator can comprise a bending element 44.

In this aspect, it is contemplated that the bending element 44 of the actuator 42 can optionally be positioned between straight portions 48 of the actuator that are secured to the adjacent segments 20. It is further contemplated that the bending element 44 of each actuator 42 can be positioned in between the adjacent segments 20 of the plurality of spaced segments, thereby defining a respective joint 41 of the probe 10.

In exemplary aspects, each high-power-density actuator 42 can be a shape-memory alloy (SMA) actuator, such as, for example and without limitation, an SMA wire. In these aspects, it is contemplated that the bending element 44 of each actuator 42 can comprise a bending portion of the actuator. It is further contemplated that the bending portion of the actuator 42 can be integrally formed with the straight portions 48 of the actuator, as depicted in FIGS. 1-6. As is known in the art, SMA materials exhibit a shape memory effect, which refers to the ability to memorize their shape at a lower temperature and recover large deformation on thermal activation. The shape memory effect arises as a result of the reversible crystalline phase transformation that occurs between the low temperature martensite and high temperature austenite phases. This transformation can be caused by joule heating (resistive heating) or thermal heating. A NiTi-based SMA can exist in three different crystal structures or phases: martensite, austenite and stress-induced martensite. Although the austenite and martensite phases have the same chemical composition, the two phases have different crystallographic structures. Martensite phase has low yield strength and material can be deformed into other shapes by applying relatively small force whereas austenite, the high-temperature phase, is relatively hard and its Youngs Modulus is almost twice as high. If the material is at a low temperature, its phase is martensite and it is said to be 'twinned' with each layer separated by a twinning boundary. Applying external stress to the martensite results in stress-induced martensite which is also called 'detwinned' martensite. The alloy initially behaves elastically during deformation up to several percent. Further stressing can cause unrecoverable strain and results in plastic deformation or fracture of the material. Full shape recovery can be achieved by heating above its transition temperature where the alloy takes its original austenitic phase.

It is contemplated that the each actuator 42 of each joint assembly 40 can be configured for selective actuation. In response to actuation, the bending element 44 of each actuator 42 can be configured for movement about and between a straight position and a curved position.

In exemplary aspects when the actuator comprises straight portions 48, the straight portions of each actuator 42 can be optionally configured to remain in a straight configuration upon actuation; that is, even though the straight portions 48 can be actuated and can undergo a phase transformation, they can be configured to remain in a straight configuration. It is contemplated that these configurations can reduce the mechanical stress on the actuator 42. Alternatively, when crimping rings are used to secure the straight portions 48 of the actuators to the segments 20 as more fully described herein, it is contemplated that, even when the straight portions of the actuator are configured for bending movement in response to actuation, the crimping rings can hold the straight portions of the actuator against the segments such that the straight portions of the actuator remain in a straight configuration and only undergo a phase transformation. It is further contemplated that the movement of the bending elements 44 of the actuators 42 in response to actuation can adjust the shape of the probe 10 at each joint 41 along the length 11 of the probe.

It is contemplated that each actuator 42 of the probe 10 can have any diameter suitable for a particular application. Optionally, in exemplary aspects, each actuator 42 of the probe 10 can have a diameter ranging from about 0.40 mm to about 0.60 mm. In other exemplary aspects, each actuator 42 of the probe 10 can optionally have a diameter ranging from about 0.45 mm to about 0.55 mm. However, it is contemplated that the actuators 42 of the probe 10 can have smaller or larger diameters in appropriate circumstances. In exemplary aspects, when the actuators 42 comprise a SMA material, it is contemplated that each actuator of the probe 10 can comprise any conventional SMA material, including, for example and without limitation, drawn Nitinol, Flexinol® (Dynalloy Inc.), and the like.

Figure 3:
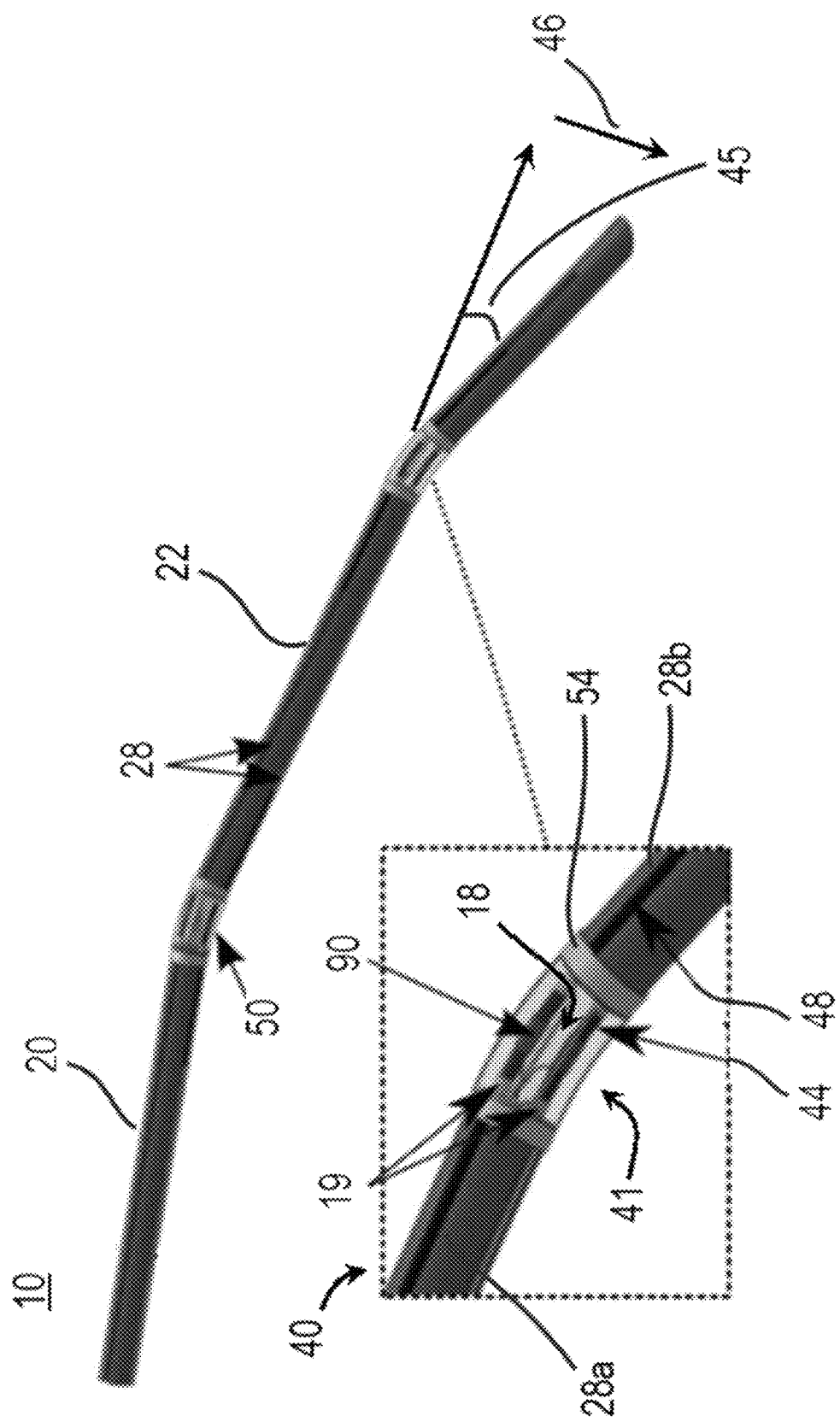
FIG. 3 depicts a schematic view of an exemplary probe as disclosed herein, including a close-up partially transparent view of a joint assembly.

During operation of exemplary probes having actuators 42 with straight portions 48, it is contemplated that, when each bending element 44 is in the straight position, the straight portions 48 of each actuator 42 can be substantially aligned with their corresponding bending element 44 (such as, for example, a bending portion integral to the straight portions of the actuator), and the entire probe 10 can be substantially straight. It is contemplated that the sheaths (discussed below) and the actuators 42 can be rigid enough to avoid bending during insertion of the probe 10 into soft tissue. As shown in FIG. 3, upon actuation of each actuator 42, it is contemplated that the bending element 44 of each actuator can be configured for movement in a bending direction 46. It is further contemplated that, as the bending element 44 is bent toward the curved position, the bending element can define a bending angle 45, corresponding to the displaced position of the central axis 12 of the segment of the probe 10 displaced by movement of the bending element, as measured relative to a line corresponding to the original position of the central axis 12 of the probe when the bending element 44 was in the straight position. It is still further contemplated that the curved position of each bending element 44 can correspond to the location of the bending element when the maximum bending angle 45 is achieved.

As one will appreciate, in order to ensure actuation of the actuator 42, the opposed straight portions 48 of the actuator cannot be connected to the same metallic component. When the segments 20 comprise a metallic material, it is contemplated that only one actuator 42 can be used at each joint 41 of the probe. In order to prevent short-circuiting, it is contemplated that a clearance between adjacent segments 20 of the probe 10 can be provided. It is further contemplated that metallic segments 20 can be coated with a non-conductive paint to prevent short-circuiting and actuation of other actuators 42 at the same joint. Alternatively, the segments can comprise plastic, which prevents short-circuiting and actuation of other actuators 42 at the same joint. It is further contemplated that the use of non-metallic segments can advantageously minimize heat conduction between the actuators.

In exemplary aspects, it is contemplated that the bending element 44 of each actuator 42 can be annealed in an arc shape that can be used for actuation along the length 11 of the probe 10. In these aspects, it is contemplated that the bending element 44 can generate a specifically controlled bending action which can enable a physician to locally control the bending angle at discrete locations along the length 11 of the probe 10. The maximum radius of curvature of the bending elements 44 can be controlled prior to annealing, and the curvature (and, thus, the bending angle) can be locally and continuously controlled during actuation.

It is contemplated that this design of the bending elements can provide a small radius of curvature while also permitting the making of trajectory corrections by controlling the bending angle. It is further contemplated that the use of pairs of antagonistic actuators 42 can permit bending in two or more directions orthogonal to the plane of the actuators when the bending elements 44 are positioned in the straight position. It is further contemplated that the straight portions 48 of each actuator 42 can be annealed in a substantially straight orientation.

In exemplary aspects, the at least one actuator 42 of each joint assembly 40 can comprise a plurality of actuators, wherein the bending element 44 of each actuator of the plurality of actuators is configured for bending in a respective bending direction 46. In these aspects, it is contemplated that the bending direction of the bending element 44 of a first actuator of the plurality of actuators can be different from the bending direction of the bending element of at least one other actuator of the plurality of actuators.

In a further aspect, each joint assembly 40 of the at least one joint assembly can comprise a joint sheath 50. In this aspect, the sheath 50 of each joint assembly 40 can be configured to receive electrical cabling and diagnostic and/or therapeutic tools as described further herein. It is contemplated that the sheath 50 of each joint assembly 40 can be secured to and positioned between consecutive segments 20 of the plurality of spaced segments. In exemplary aspects, each sheath 50 of each joint assembly 40 can comprise a flexible, non-conductive material.

In another aspect, it is contemplated that the probe 10 can comprise an outer sheath 60. In exemplary aspects, it is contemplated that the outer sheath 60 can extend along substantially the entire length 11 of the probe 10. In these aspects, it is contemplated that the outer sheath 60 can comprise a flexible, non-conductive material.

It is contemplated that the inner channel 18 of the probe 10 can have any inner diameter suitable for a particular application. It is further contemplated that the probe 10 can have any outer diameter suitable for a particular application. However, in exemplary aspects, it is contemplated that the inner diameter of the inner channel 18 of the probe 10 (and of each segment 20 of the plurality of spaced segments) can optionally range from about 1.0 mm to about 2.0 mm. In other exemplary aspects, it is contemplated that the inner diameter of the inner channel 18 of the probe 10 (and of each segment 20 of the plurality of spaced segments) can optionally range from about 1.2 mm to about 1.7 mm. In additional exemplary aspects, it is contemplated that each segment 20 of the plurality of spaced segments can optionally have an outer diameter ranging from about 1.0 mm to about 2.0 mm. In further exemplary aspects, it is contemplated that each segment 20 of the plurality of spaced segments can optionally have an outer diameter ranging from about 1.4 mm to about 1.8 mm.

In exemplary aspects, the plurality of spaced segments 20 can comprise a first end segment 20a defining the first end 14 of the probe 10 and a second end segment 20b defining the second end 16 of the probe. In these aspects, it is contemplated that the first end 14 of the probe 10 can define at least one opening 15 configured to receive electrical connections 19 (e.g., cables, wiring, fiber optics, and the like) and at least one of a diagnostic tool and a therapeutic tool, such as those described above. It is further contemplated that the second end 16 of the probe 10 can define an opening 17 in communication with the inner channel 18. In exemplary aspects, it is contemplated that the opening 17 of the second end 16 of the probe 10 can serve as an imaging window during a medical procedure. Optionally, it is contemplated that a side imaging window can be defined in a side wall of the probe 10 at a selected position along the length 11 of the probe. Optionally, the second end 16 of the probe 10 can be beveled (See FIGS. 1 and 2).

In other exemplary aspects, the wall 22 of each segment 20 of the plurality of spaced segments can define at least one slot 28 that is opposed from a corresponding slot defined by an adjacent segment such that at least one pair of opposed slots is positioned at each joint assembly 40. In these aspects, each pair of opposed slots 28a, 28b can be configured to receive corresponding straight portions 48 of a respective actuator 42 of the joint assembly 40. Optionally, the straight portions 48 of the actuator 42 can be secured within the slots 28 using an adhesive, such as, for example and without limitation, an epoxy.

In one exemplary aspect, the at least one actuator 42 of each joint assembly 40 can comprise two actuators 42. In this aspect, the at least one pair of opposed slots 28 at each joint assembly 40 can comprise two pairs of opposed slots. It is contemplated that the two actuators 42 at each joint assembly 40 can comprise two antagonistic actuators.

In another exemplary aspect, the at least one actuator 42 of each joint assembly 40 can comprise four actuators 42. In this aspect, the at least one pair of opposed slots 28 at each joint assembly 40 can comprise four pairs of opposed slots. It is contemplated that the four actuators 42 at each joint assembly 40 can comprise two pairs of antagonistic actuators.

Optionally, in another aspect, each joint assembly 40 of the at least one joint assembly can comprise a pair of spaced rings 54 respectively secured to adjacent segments 20 of the plurality of segments on opposing sides of the corresponding joint 41 of the probe 10. In this aspect, the at least one actuator 42 of the joint assembly 40 can be positioned between the adjacent segments 20 and the pair of rings 54 such that each actuator 42 is secured to both of the adjacent segments. In exemplary aspects, the pair of spaced rings 54 can comprise stainless steel. In other exemplary aspects, the pair of spaced rings 54 can comprise a non-metallic material.

In other exemplary aspects, when the adjacent segments 20 comprise a metallic material and more than one actuator 42 is positioned at each joint 41 of the probe 10, it is contemplated that a first non-conductive material (e.g., a non-conductive sheath) can be placed over the segments. In these aspects, it is contemplated that the actuators 42 can be in contact with an outer surface of the first non-conductive material, and a second non-conductive material (e.g., a second non-conductive sheath) can be placed over the first non-conductive material and the actuators 42. The pair of spaced rings 54 can then be placed over the second non-conductive material to crimp the actuators into place. The outer sheath 60 can then be positioned over the rings 54. It is contemplated that the above-described configuration can effectively isolate the actuators 42 from the metallic materials of the segments 20 and rings 54. If the spaced rings 54 comprise a non-metallic material, then it is contemplated that the second non-conductive material is optional.

FIG. 3A shows a perspective view of the joint assembly 40 and the segments 20a and 20b extending at the sides thereof, as well as the cross-sections of the segments 20a and 20b taken along lines A-A and B-B of FIG. 3A. The segment 20a is configured with the slot 28a, while the opposite segment 20b is configured with the slot 28b extending therealong. Additional slots 28c, 28e, and 28g are formed in the segment 20a, and slots 28d, 28h, and 28f are formed in the segment 20b for receiving and securing therein corresponding SMA actuator members, and particularly, the straight ending portions thereof.

In one embodiment, the joint assembly 40 includes actuator members 44 and 44*a*, which constitute a pair of antagonistic SMA actuator members. In this embodiment, the slots 28*a*-28*b* serve for receiving the ending portions 48 of the actuator member 44, while the slots 28*c*-28*d* serve for receiving the ending portions 48*a* of the actuator member 44*a*, which is antagonistic to the actuator member 44. Alternatively, in another embodiment, when the joint assembly includes two pairs of the antagonistic SMA actuator members 44-44*a*, and 44*b*-44*c*, the slots 28*e*-28*h* receive the ending portions 48*b* of the actuator member 44*b*, while the slots 28*f*-28*g* receive the ending portions 48*c* of the SMA actuator member 44*c* which is antagonistic to the SMA actuator member 44*b*.

In operation, one or more actuated members may be actuated, as needed to attain a multi-dimensional steering of the probe. Each actuator member may be controlled independently, with a selective actuation applied to one (or more) of the SMA actuator members. For example, the actuator member 44 may be actuated when bending in one direction is needed, and a selective antagonistic actuation may be applied to another actuator member (for example, the actuator member 44*a* antagonistic to the actuator member 44) when bending in the opposite direction is needed for steering the probe as required by a medical procedure. Alternatively, or in addition thereto, actuator members placed in orthogonally disposed slots may be actuated (fix example, the actuator members 44-44*b*, or 44-44*c*, or 44*b*-44*a*, or 44*c*-44*a*), so that an arbitrary motion in a 3 dimensional space may be attained.

It is contemplated that the actuators 42 can be crimped at their tips using the rings 54. It is further contemplated that the electrical connections 19 can comprise enamel-coated wires that are wrapped around the tips of the actuators 42. In exemplary aspects, after assembly of a probe 10 comprising spaced rings 54 at each joint assembly 40 and an outer sheath 60 as disclosed herein, it is contemplated that the outer diameter of the probe can range from about 2.5 mm to about 3.5 mm and, in exemplary aspects, be about 3.0 mm, while the inner diameter of the probe is defined by the inner diameter of the segments 20. However, it is contemplated that the probe can have any outer diameter suitable for a particular application, such as a medical procedure.

Optionally, in a further aspect, the probe 10 can further comprise a plurality of imaging markers 70 secured to the probe. In this aspect, it is contemplated that the imaging markers 70 can be used to control the shape and position of the probe with image feedback, as further described herein. In an exemplary aspect, a pair of spaced imaging markers 70 can be secured to an area corresponding to each respective segment 20 of the probe 10. It is contemplated that any known imaging marker can be used. In operation, it is contemplated that the imaging markers 70 can be monitored using a camera.

In exemplary aspects, the image feedback can primarily be provided by clinical imaging modalities such as, for example and without limitation, Magnetic Resonance Imaging (MRI), Computed Tomography (CT), Ultrasound (US), Fluoroscopy, and the like. When clinical imaging modalities are used, it is contemplated that image processing techniques can be employed to extract the probe position from the medical images.

Optionally, in still another aspect, an imaging device 80 can be provided for use with the probe 10. In exemplary aspects, it is contemplated that at least a portion of the imaging device 80 be positioned within the inner channel 18 of the probe 10. In this aspect, it is contemplated that the imaging device 80, such as a camera or optical coherence tomography (OCT) probe, can have a lens 82 operatively positioned in communication with an imaging window of the probe 10 as further described herein. In exemplary aspects, the lens 82 can be positioned in communication with the opening 17 of the second end 16 of the probe 10 and/or with an opening in a sidewall of the probe.

Optionally, in yet another aspect, the probe 10 can further comprise at least one temperature sensor 90. In this aspect, it is contemplated that each temperature sensor 90 of the at least one temperature sensor can be operatively coupled to an actuator 42. It is further contemplated that each temperature sensor 90 can be configured to provide a signal indicative of the temperature of a respective actuator 42. In exemplary aspects, the temperature sensors 90 can be resistance temperature detectors (RTDs) as are known in the art. Alternatively, in other exemplary aspects, the temperature sensors 90 can be thermocouples as are known in the art.

In an additional aspect, the probe 10 can further comprise means for measuring the resistance of the at least one actuator 42. In this aspect, it is contemplated that the means for measuring the resistance of the at least one actuator can be incorporated into the electrical connections and circuitry within the probe system 100 disclosed herein.

In various aspects, and with reference to FIGS. 6A and 6B, the probe 10 can be provided as part of a probe system 100. In these aspects, the probe system 100 can further comprise means for selectively effecting movement of the bending element 44 of each actuator 42 of each joint assembly 40 of the probe 10 about and between the straight position and the curved position.

Optionally, in one aspect, the means for selectively effecting movement of the bending element 44 can comprise a circuit controller 110 as is known in the art. In this aspect, the controller 110 can be positioned in operative communication with each actuator 42 of the probe 10. It is contemplated that the controller 110 can be configured to selectively deliver a control input to at least the bending element 44 of each actuator 42. It is contemplated that, in exemplary aspects, the controller 110 can be positioned in electrical communication with each actuator 42, and the controller can be configured to selectively deliver current to at least the bending element 44 of each actuator. However, it is contemplated that any known communication means and control inputs can be used. In exemplary aspects, the circuit controller 110 can be in operative communication with a conventional computer having a processor, with the processor of the computer being programmed with instructions that are configured to effect one or more of the actions and/or steps disclosed herein. It is contemplated that the circuit controller 110 can be positioned in electrical communication with the bending elements 44 of the probe 10 via electrical connections 19, as shown in FIG. 4. In exemplary aspects, the electrical connections 19 are positioned within the inner channel 18 of the probe 10. However, it is contemplated that the electrical connections 19 can be positioned externally to the inner channel 18 of the probe.

It is contemplated that the bending elements 44 of the probe can be configured to undergo large deformations (recovering their curved positions) upon thermal activation. It is further contemplated that the recovery strain of each actuator 42 can be related to its temperature. Thus, it is contemplated that selective control of the temperature of the actuator 42 can be used to control the position of the probe 10. It is further contemplated that the temperature of the actuator 42 can be selectively controlled by selective heating of the bending elements 44 at each joint 41 of the probe 10. In exemplary aspects, the controller 110 can comprise a pulse-width-modulated-based (PWM-based) controller that is configured to selectively deliver current to all actuators 42 of the probe at discrete times. It is contemplated that the PWM-based controller 110 can be configured to deliver current to each actuator 42 independent of the other actuators. It is further contemplated that the PWM-based controller 110 can deliver current to the actuators 42 through use of a switching circuit as is known in the art.

In exemplary aspects, and with reference to FIG. 6A, when each joint assembly 40 of the probe 10 comprises at least one temperature sensor 90 and/or resistance sensor as disclosed herein, it is contemplated that each temperature sensor and/or resistance sensor can be in electrical communication with the controller 110 and operatively coupled to an actuator 42. In these aspects, each temperature sensor 90 of the at least one temperature sensor can be configured to produce an output signal indicative of the temperature of a corresponding actuator 42, and each temperature sensor can be further configured to transmit its output signal to the controller 110. Based upon the measured temperature of each respective actuator 42, the controller can be configured to selectively adjust, stop, and/or deliver the control input to the actuator.

Similarly, the controller 110 can be configured to receive an input indicative of the resistance of each respective actuator 42. Based upon the measured resistance of each respective actuator 42, the controller can be configured to selectively adjust, stop, and/or deliver the control input to the actuator.

In other exemplary aspects, and with reference to FIG. 6B, the probe system 100 can further comprise an imaging means 120, such as a conventional imaging modality system as is known in the art. In these aspects, it is contemplated that the imaging means 120 can be configured to produce at least one image depicting the location of the probe 10.

In one aspect, it is contemplated that when each segment 20 of the plurality of spaced segments comprises at least two markers 70 as disclosed herein, the markers can be configured for detection using a camera. It is further contemplated that the imaging means 120 can be positioned in operative communication with the controller 110. In operation, the controller 110 can be configured to selectively deliver current to the actuators 42 of the probe 10 in response to the detection of the at least two markers 70 on each straight segment by the camera 120.

In additional exemplary aspects, the imaging means 120 can comprise a clinical imaging modality system, such as, for example and without limitation, a Magnetic Resonance Imaging (MRI) machine, a Computed Tomography (CT) machine, an Ultrasound (US) machine, and a Fluoroscopy machine. In these aspects, it is contemplated that the imaging means 120 can be used to produce images of a selected area, such as, for example, the region of a subject where the probe is positioned. It is further contemplated that conventional image processing techniques can be used to extract the position of the probe from the medical images. For example, in various optional aspects, the imaging means can be in operative communication with a processor that is configured to receive the at least one image. In these aspects, it is contemplated that the processor can be configured to determine the location of the probe 10 (including the bending angle 45 of each bending element 44) based upon the at least one image. It is further contemplated that the processor can be configured to apply one or more known image processing algorithms and/or methods to determine the location (including the bending angle 45 of each bending element 44) of the probe 10.

In still other exemplary aspects, it is contemplated that the temperature-feedback and position-based, image-guided feedback systems can be combined into a dual-feedback system that makes use of both image guidance and temperature monitoring to determine appropriate actuation of each respective actuator 42. In these aspects, it is contemplated that the bending angle (strain) can be measured by the imaging means 120, and the temperature can be measured by the temperature sensor 90 as described further herein. It is further contemplated that when image feedback from the imaging means 120 is not optimal, the physician or other user of the probe system 100 can rely on the temperature feedback. Similarly, when the temperature feedback is not optimal, it is contemplated that the physician or other user of the probe system 100 can rely on the image (position) feedback. Thus, although there is redundant information between the temperature guided and image-guided feedback mechanisms, it is contemplated that such a dual-feedback system can provide for improved tracking and control of the motion of the probe while also improving the safety and reliability of a particular procedure. When the strain and the temperature of the actuator 42 are known, it is contemplated that the external stress acting on the actuator can be found using a constitutive model of the actuator material, as further described herein. In exemplary aspects, the dual-feedback system disclosed herein can be used with a PWM-based controller.

When an imaging means 120 is used to provide feedback on the position of the probe 10 as disclosed herein, it is contemplated that the materials of the probe must necessarily be compatible with the particular imaging means employed. Thus, for example, when the imaging means comprises an MRI machine, it is contemplated that the probe 10 can comprise non-magnetic materials.

EXAMPLES

The following examples are put forth so as to provide those of ordinary skill in the art with a complete disclosure and description of how the probes, probe systems, and methods claimed herein are used and evaluated and are intended to be purely exemplary of the invention and are not intended to limit the scope of what the inventors regard as their invention. However, those of skill in the art should, in light of the present disclosure, appreciate that many changes can be made in the specific aspects which are disclosed and still obtain a like or similar result without departing from the spirit and scope of the invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric pressure.

Although described below with reference to specific exemplary probes, it is contemplated that the methods of monitoring and controlling the positioning and orientation of the SMA wires disclosed in the following examples can be applied to monitor and control the position and orientation of the actuators of any probe as described herein. Additionally, it is contemplated that any of the SMA material processing methods disclosed in the following examples can be employed to prepare SMA actuators suitable for use with the probes disclosed herein.

Example A

Motion Planning for the Discretely Actuated Steerable Cannula

Motion planning for a cannula (probe) as disclosed herein in a 2D imaging plane was considered by Ayvali and Desai (E. Ayvali, and J. P. Desai, "Motion planning for the discretely actuated steerable cannula", In *IEEE International Conference on Biomedical Robotics and Biomechatronics (BIOROB* 2012), pp. 50-55, June 24-27, Roma, Italy, 2012). For the task of reaching a desired position in a 2D plane without any restriction on the tip orientation, a cannula with more than one joint becomes redundant. In general, redundant mechanisms can have infinite number of configurations to achieve a desired workspace specification. The redundant DOF can be utilized to optimize secondary performance criteria without affecting the primary task. The configuration control approach by Seraji and Colbaugh (R. Colbaugh, H. Seraji, and K. L. Glass, "Obstacle avoidance for redundant robots using configuration control", *Journal of Robotic Systems*, 6(6):721-744, 1989) is an efficient method for redundant robots to achieve the main task of desired end-effector motion while satisfying additional tasks. The proposed controller can achieve task space tracking while utilizing the redundancy to impose kinematic and dynamic constraints to avoid joint limits, singularity and obstacles while maintaining posture control. Using the configuration control approach, the extra degrees-of-freedom of the cannula can be exploited to achieve additional tasks. The redundancy of the cannula can be utilized to avoid obstacles and find trajectories without exceeding the maximum achievable curvature of the SMA wire. Hence, the variables affecting the joint limit of the SMA actuators were explored and incorporated into the configuration control approach to plan trajectories for the cannula.

Materials and Methods

A. Discretely Actuated Steerable Cannula

The cannula can be composed of straight segments and can have a 1.651 mm inner and a 3.175 min outer diameter. The SMA wires can be annealed in an arc shape and by controlling the temperature of the SMA wires, the radius of curvature during phase transformation (hence the bending angle) can be controlled. The original arc shape can have a 1.37 cm radius of curvature and the maximum bending angle that can be achieved is 21 degrees. An exemplary 2-DOF prototype is shown in FIG. 4.

B. Configuration Control

A redundant manipulator has more DOF than the dimension of the workspace. In other words, the dimension of the joint space n is larger than the dimension of the workspace m. The cannula is assumed to be inserted from a single point with a fixed orientation and the final orientation of the tip is not important. Therefore, the discretely actuated steerable cannula has 3-DOF: 1-DOF at each joint and 1-DOF along the insertion direction. As a result, the cannula has an additional DOF in a 2D workspace.

For a n-DOF manipulator with r redundant DOF (r=n−m) the optimum joint rates, q, that penalize high joint rates and minimize the error for the main and additional tasks are given by Equation A1, as follows:

$$\dot{q} = (J_m^T W_m J_m + J_a^T W_a J_a + W_s)^{-1} (J_m^T W_m \dot{x} + J_a^T W_a \dot{z}) \quad (1)$$

where x is the main task of reaching the desired position and z is the additional task. $J_m$(m×n) and $J_a$(r×n) are the Jacobian matrix associated with the main task and the additional task, respectively. $W_m$(m×m), $W_s$(n×n), $W_a$(k×k) are positive definite diagonal weighting factors of the main task, singularity avoidance and the additional task. The additional task has no restriction on its dimension. If k>r the algorithm searches for the best solution that minimizes all the additional tasks depending on their weighting factors.

To find the required joint positions to complete the task, the joint rates are integrated. First, a path connecting the initial and the final positions can be assumed with a motion period T. The simplest assumption is a line segment divided into N intervals and a planned velocity given by Equation A2, as follows:

$$\dot{x}_k = \gamma \frac{x^d - x_k}{(N+1-k)\Delta t}, \Delta t = \frac{T}{N} \quad (2)$$

where $x^d$ is the desired position of the end effector and γ is the deceleration factor greater than 1. Then, q can be obtained by numerically integrating Eq. 1.

Motion Planning

Herein, a 2-DOF planar discretely actuated cannula was considered with 3.81 cm, 3.81 cm and 2.54 cm length sections from the base to the tip. A simplified model of the cannula was used as a serial manipulator in prismatic-revolute-revolute configuration. The joint variables, q, for the 3-DOF cannula are the insertion distance u and the bending angle for each joint, $\alpha_i$(i=1,2). $\alpha_i$ is defined to be positive in the counter clockwise direction.

A. Singularity Avoidance and Obstacle Avoidance

The anatomical structures that need to be avoided in motion planning can be in various shapes. As an initial approach, convex polygon obstacles were considered. It is assumed that the location of the obstacles are known and continuously updated. The additional task of obstacle avoidance is activated when the minimum distance between a link and the nearest obstacle, $d_i$, is smaller than a critical distance, $r_o$. As set forth in Equation A3, the additional task of obstacle avoidance is defined as:

$$z_i = r_o - d_i \quad (3)$$

And, as set forth in Equation A4, $d_i$ is defined as:

$$d_i = \hat{e}_i^T (x_{ci} - x_o) \quad (4)$$

where $x_o = [x_o^1, x_o^2]^T$ are the coordinates of the closest point on the obstacle to link i, $x_{ci} = [x_{ci}^1, x_{ci}^2]^T$ are the coordinates of the critical point on link i which has the closest distance to the obstacle and $\hat{e}_i$ represents the unit vector pointing from $x_o$ to $x_{ci}$ (see FIG. 7).

When ($d_i < r_o$) obstacle avoidance task becomes active. As set forth in Equation A5, the Jacobian for the additional task of obstacle avoidance is given as:

$$J_{a_i} = -\hat{e}_i^T \frac{\partial x_{ci}}{\partial q} \quad (5)$$

The configuration control is an optimization based approach and if there is a local minima, the motion planning algorithm may fail. Another consideration is the joint limit of the SMA actuator. Even though the obstacles and the target point are inside the workspace of the cannula, the joint limits required for obstacle avoidance may exceed the physical joint limit of the SMA actuator. If there is a local minima, intermediate points can be defined between the initial position and the target position to divide the motion planning problem into sub-problems. Voronoi diagram can be used to define these intermediate points between the initial and the final position. The algorithm was implemented in MATLAB and FIG. 8 shows an example where the joint limit is exceeded for the SMA actuation in simulation and hence is not physically realizable. In one example, the parameters can be set at $r_o=0.07$, $\gamma=4$ and the diagonal terms of the weighting factors were set to $W_{mii}=[3,3]$, $W_{sii}=[0.1,0.1,0.1]$, $W_{aii}=[0,25,25]$. The desired position can be set to [12.5000, −0.3600] and the final position achieved by the planner while avoiding obstacles can be [12.5000, −0.3590]. Use of a Voronoi diagram can prevent the planner from getting stuck at a local minima or hitting an obstacle if the target is right behind the obstacle. On the other hand, avoiding the joint limit is not trivial. The joint limit may not only limited by the physical limits of the actuator (radius of curvature), but there can be multiple factors affecting the maximum achievable bending angle.

B. Joint Limit Avoidance

The maximum bending angle of each joint can be limited by the minimum radius of curvature of the annealed SMA wire. It also depends on the initial strain of the SMA actuators and the stress acting on the SMA actuators (and hence the tissue stiffness). The antagonistic SMA actuators at each joint experience different strain levels during trajectory execution. The strain due to bending, $\epsilon_b$, can be calculated from the bending angle (arc angle) using the relationship set forth in Equation A6:

$$\varepsilon_b = \frac{\alpha d}{2\ell} \tag{6}$$

where l and d are the length and the diameter of the SMA actuator. Note that $\epsilon_b$, can take negative values and a negative value means the bending takes place in the opposite direction. The original shape of the SMA wires can be an arc with 1.37 cm radius of curvature and this configuration corresponds to zero strain. After the assembly of the cannula, both SMA wires are straight and the strain in both wires can be 0.0195 (1.95%). As set forth in Equation A7, the relationship between the strain of the SMA wire and the bending angle can be found as:

$$\epsilon_{ccw}=0.0195-\epsilon_b$$

$$\epsilon_{cw}=0.0195+\epsilon_b \tag{7}$$

where $\epsilon_{ccw}$ is the strain of SMA actuator that can bend in positive (counter-clockwise) direction and $\epsilon_{cw}$ is the strain of the SMA actuator can bend in negative (clockwise) direction. A planning problem is considered in FIG. 9. The desired position and the intermediate point can be [10.5000, 1.2000] and [8.6890, 2.1130], respectively. The final position achieved by the planner is [10.4910, 1.2000]. By examining the change in $\alpha_2$ for this trajectory, initially the SMA wire that can bend in positive direction is actuated. As it transforms into an arc shape, the bending angle of joint 2 increases up to 0.3352 radians (see FIG. 10). Hence, the actuated SMA wire recovers 0.0179 strain ($\epsilon_b=0.0179$, $\epsilon_{ccw}=0.0016$) until T=100 whereas the antagonistic SMA wire naturally deforms and its strain increases to 0.0374. After T=100, the bending direction is reversed. For the same bending angle, both SMA wires experience different strain values. Therefore, the strain in the actuated SMA wire can be considered while finding the joint limit.

To determine the effect of the tissue stiffness on the joint limit, the constitutive equation of the SMA wire can be examined. Stress, strain and temperature are the three variables that are used to describe the SMA behavior. Tanaka (K. Tanaka, "A thermomechanical sketch of shape memory effect: One-dimensional tensile behavior", *Res. Mechanica*, 18:251-263, 1986) modeled the strain, $\epsilon$, temperature, T, and martensite volume fraction, $\xi$, as the only state variables. The constitutive equation (Equation A8) is given as:

$$\sigma-\sigma_o=E(\xi)(\epsilon-\epsilon_o)+\Omega(\xi)(\xi-\xi_o)+\Theta(\xi)(T-T_o) \tag{8}$$

where $E(\epsilon, \xi, T)$ represents the elastic modulus, $\Omega(\epsilon, \xi, T)$ is the phase transformation coefficient and $\Theta(\epsilon, \xi, T)$ is thermal coefficient of expansion for the SMA material. The strain can be neglected due to the thermal coefficient of expansion since it is much lower than the strain due to the phase transformation. The terms associated with subscript 'o' refer to the initial state of the material. As set forth in Equation A9, the elastic modulus is defined as:

$$E(\xi)=E_A+\xi(E_M-E_A) \tag{9}$$

As set forth in Equation A10, the phase transformation constant, $\Omega$, can be expressed as:

$$\Omega(\xi)=-\epsilon_L E(\xi) \tag{10}$$

where $\epsilon_L$ is the maximum recoverable strain. A cosine function is used for the martensite volume fraction developed by Liang and Rogers (C. Liang, C. and C. A. Rogers, "One-dimensional thermomechanical constitutive relations for shape memory material", *Journal of Intelligent Materials and Structures*, 1(2):207-234, 1990) as a function of stress and temperature. As set forth in Equation A11, during the martensite to austenite (M→A) phase transformation, $\xi$, is given by:

$$\xi = \frac{\xi_o}{2}\{\cos[a_A(T-A_s)+b_A\sigma]+1\} \tag{11}$$

where $a_A$, $b_A$ are constants defined in Equation A12 as:

$$a_A = \frac{\pi}{A_f - A_s}, b_A = -\frac{a_A}{C_a} \tag{12}$$

and $C_a$ is called the stress influence coefficient. Due to the two antagonistic wires at each joint, the non-heated SMA wire can be naturally deformed by the heated wire. If the bending direction needs to be reversed, the controller can switch to the antagonistic SMA wire once the actuated SMA wire is cooled to the martensite phase. Hence, only the heating phase is considered and the hysteresis behavior of the SMA wire can be neglected. Exemplary material properties and the physical properties of the SMA actuator are given below in Table A.I. $A_s$ and $A_f$ values capture the overall effect of the antagonistic SMA wire and the sheath on the joints.

TABLE I

MATERIAL AND PHYSICAL PROPERTIES OF THE SMA ACTUATOR

| | | | |
|---|---|---|---|
| $E_A$ | 104.31 GPa | $E_M$ | 48.69 GPa |
| $C_u$ | 30 MPa/° C. | $A_s$ | 31.5° C. |

TABLE I-continued

MATERIAL AND PHYSICAL PROPERTIES OF THE SMA ACTUATOR

| $A_f$ | 64.5° C. | d | 0.5334 mm |
|---|---|---|---|
| l | 5 mm | r | 1.37 cm |

If it is assumed that the soft-tissue is linear elastic and model it as a torsional spring with stiffness K attached at each joint, the external stress acting at each joint during bending can be expressed in Equation A13 as:

$$\sigma = \frac{M(d/2)}{I} = \frac{K(\Delta\alpha)(d/2)}{I} = \frac{K(\varepsilon_0 - \varepsilon)\ell}{I} \quad (13)$$

where M is the bending moment, I is the area moment of inertia and $\varepsilon_o > \varepsilon$ since the strain is recovered during actuation. As set forth in Equation A14, substituting Eq. A13 into Eq. A8 results in a nonlinear equation which can be expressed in terms of the stress as:

$$E(\xi)\left(\frac{\sigma I}{K\ell}\right) + \varepsilon_L E(\xi)(\xi - \xi_o) + (\sigma - \sigma_o) = 0 \quad (14)$$

From Eq. A14, the change in external stress, σ, can be found as a function of temperature T, and these values can be used to find the corresponding strain in the SMA wire using Equation A15:

$$\varepsilon = \frac{\sigma - \sigma_o}{E(\xi)} + \varepsilon_o + \varepsilon_L(\xi - \xi_o) \quad (15)$$

The maximum temperature of the SMA wire that can be used in motion planning to $A_f$ can be limited. FIG. 11 shows the change in strain with temperature up to $A_f$ for different K values and for different initial strain values. By inspecting FIG. 11 it can be seen that the maximum recoverable strain (and hence the maximum joint angle) depends on the stiffness K and the initial strain in the SMA wire before actuation. For example if K=4 N mm/rad, $\varepsilon_0$=0.039 and the parameters in Table I, at T=$A_f$ the strain of the SMA wire is $\varepsilon$=0.0042. This value corresponds to a maximum bending angle α=0.2868 rad (16.43 degrees). A conservative selection of the joint limit can be made since the maximum joint angle that will be required is not known a priori and that the maximum bending angle will be required when a joint starts to bend in one direction can be assumed. When there is a change in the bending direction, Eq.A14 and Eq.A15 are solved to find the new joint limit using the values for the initial strain of the SMA wire that is being actuated and the stiffness K. This joint limit can be taken into account and define the additional task of joint limit avoidance. Additional task for joint limit can be defined as a one-to-one function of the joint variables (z=q) and the corresponding Jacobian is given as $J_j = I_{3\times3}$. Upon reaching the joint limits, the joint rates must disappear. Therefore, the desired joint rates are selected to be zero ($z^d$=0) when the additional task is active. As set forth in Equation A16, the diagonal entities of weight matrix for the additional task of joint limit are defined as:

$$W_{jii} = \begin{cases} W_o & q_i < q_i^{min} \\ \frac{W_o}{2}\left[1 + \cos\left(\pi\left(\frac{q_i - q_i^{min}}{\tau_i}\right)\right)\right] & q_i^{min} \leq q_i \leq q_i^{min} + \tau_i \\ 0 & q_i^{min} + \tau_i < q_i < q_i^{max} - \tau_i \\ \frac{W_o}{2}\left[1 + \cos\left(\pi\left(\frac{q_i^{max} - q_i}{\tau_i}\right)\right)\right] & q_i^{max} - \tau_i \leq q_i \leq q_i^{max} \\ W_o & q_i > q_i^{max} \end{cases} \quad (16)$$

τ defines the buffer region where the weight of the joint limit increases from zero to a maximum value, $W_o$. The parameters can be set at τ=0.0698 (4 degrees) and the diagonal entities of the weight factor for the additional task of joint limit avoidance as $W_{j\ ii}$=[0, 10, 6]. Again the trajectory planning problem in FIG. 9 was considered and assume a stiffness value K=10 N mm/rad. FIG. 12 shows the change in joint variables and the minimum and maximum joint angles for each joint. If the change in joint limits of $\alpha_2$ with time is examined, initially the joint can be straight and the absolute value of the minimum and maximum joint angles can be the same since the bending direction is not known. After T=100 s the joint angle starts to decrease and the bending direction is reversed. Here, the joint limit for the SMA wire that can bend in the negative direction can be considered. The joint limit for the positive bending direction remains unchanged until the joint starts to bend in the positive direction again. For an indication of the stress levels involved for K=10 N mm/rad, the interval when the bending angle $\alpha_2$ starts to decrease can be considered. The initial joint angle can be 0.2551 radians and the maximum joint angle that can be achieved at $A_f$ is −0.1818 radians. If the tissue relaxation is ignored, initially the stress acting on the actuated SMA wire is zero. The stress acting on the SMA wire increases from 0 to 293.1 MPa while it recovers the strain from $\alpha_2$=0.2551 radians to $\alpha_2$=−0.1818. FIG. 13 shows the change in joint variables with time for the cases with and without the additional task of joint limit avoidance. The final position achieved by the planner can be [10.4990, 1.2920] compared to the desired position of [10.5000, 1.2000].

C. Moving Obstacles

When the cannula moves inside the soft-tissue, the anatomical structures rarely remain stationary. Presence of other surgical tools that manipulate the tissue can also cause changes in the positions of anatomical structures. Therefore, the performance of the planner in the presence of moving obstacles was tested. FIG. 14(a) and FIG. 15(a) show two motion planning problems with moving obstacles. As set forth in Equation A17, the velocity for the $i^{th}$ obstacle is:

$$v_i = k_i(e^{-t/50}) \times 10^{-2}(m/s) \quad (17)$$

The coefficients $k_i$ and the desired position for each problem (Trajectory A and Trajectory B) are given in Table II. With the addition of obstacle avoidance and joint limit avoidance tasks, the final positions achieved by the planner are given in Table A.II. The change in joint variables with time for the trajectories is given in FIG. 14(b) and FIG. 15(b). The algorithm can successfully find a trajectory in the presence of moving obstacles while avoiding obstacles and remaining within joint limits.

TABLE II

PARAMETERS USED FOR MOTION PLANNING WITH MOVING OBSTACLES

|  | Trajectory A | Trajectory B |
| --- | --- | --- |
| Desired Position | [10.5000, 1.2000] | [13.0000, 0.5000] |
| Final Position | [10.4970, 1.2100] | [13.0000, 0.5000] |
| $k_1$ | [0.02, −0.02] | [0.01, 0.01] |
| $k_2$ | [−0.02, 0.02] | [0.01, −0.02] |
| $k_3$ | [−0.02, 0.00] | [0.01, −0.02] |
| $k_4$ | [−0.02, −0.02] | [0.01, 0.01] |
| $k_5$ | [−0.02, 0.00] | [0.00, −0.01] |

Example B

A Discretely Actuated Steerable Cannula

SMA actuators as disclosed herein were characterized to use the temperature feedback approach to control the bending angle at each joint of a probe (cannula). Characterization and modeling of straight-annealed SMA wires and springs that are thermally actuated to cause linear motion have been extensively investigated. The uniaxial testing devices and experimental setup used in characterizing straight-annealed SMA wires are not applicable when the SMA wire is annealed in an arbitrary shape. For example, measuring the elastic modulus in the austenite phase is not possible using the conventional tensile testing machine since the SMA wire does not move along a line as it bends above the transformation temperature. Hence, an experimental setup and a procedure for characterizing an SMA actuator, which is annealed in an arc shape to generate bending forces is presented in Ayvali and Desai (E. Ayvali, and J. P. Desai, "Towards a discretely actuated steerable cannula", In *IEEE International Conference on Robotics and Automation (ICRA* 2012), pp. 1614-1619, Saint Paul, Minn., May 14-18, 2012).

Materials and Methods

A. Discretely Actuated Steerable Cannula

The SMA was annealed to achieve a desired joint angle at a particular location along the cannula length upon thermal actuation. The SMA actuator was a 0.53 mm diameter drawn nitinol (manufactured by Memry, Inc.) wire. The SMA wire was first deformed into an arc shape and clamped down to a ceramic fixture to keep it fixed during annealing. Heat treatment of the SMA takes about 40 minutes followed by quenching the SMA in an ice-water mixture. After the annealing process is completed, the SMA actuator has one-way shape memory effect and upon heating the SMA actuator above its transition temperature, the SMA actuator can transform into the desired arc shape. The original arc shape has 1.37 cm radius of curvature and straight configuration corresponds to a 0.0195 (1.95%) strain.

The probe was composed of three straight segments made of copper with an inner diameter of 1.651 mm and outer diameter of 3.175 mm. The length of each section from the base to the tip is 3.81 cm, 3.81 cm and 2.54 cm, respectively. There are four slots along the length of each straight segment and up to four SMA wires can be placed at each joint. In an exemplary embodiment, there can be two antagonistic SMA wires at each joint. Since the SMA can be used primarily for actuation, SMA wires are electrically insulated. Therefore, the copper segments are painted with high temperature enamel coating (Rust-Oleum, 260° C.) for electrical insulation. There is 5 mm clearance between two consecutive links to prevent overconstraining the SMA actuators. Initially, both SMA wires were deformed into straight wires for the assembly of the cannula. SMA wires are embedded inside the slots on the outer surface of the links and can be secured inside the slots via use of an epoxy (Loctite 1324007 Epoxy). The joints were also covered with non-conductive rubber sheath for heat isolation. For electrical connection, enamel coated wires were used and attached on the SMA wire using silver filled conductive epoxy. Mini resistance temperature detector (RTD) sensors from Alpha Technics, Inc. were used as temperature sensors. The schematic and the actual prototype of the cannula are shown in FIG. 3 and FIG. 4, respectively. The hollow inner core design of the cannula can enable the introduction of both diagnostic and therapeutic tools. The cannula was not optimized for a specific application. However, the dimensions of the cannula are scalable and can be adjusted depending on the medical application.

B. SMA Position Control

To control the bending angle of the SMA actuator two different PWM-based control strategies were used, namely vision-based feedback and temperature feedback controller. Developing a temperature feedback based controller will be useful in case of poor image quality from the imaging modality. The vision-based feedback controller treats the SMA as a black box since the bending angle is directly measured. The temperature controller is used to control the bending angle indirectly using a constitutive model of the SMA actuator. The strain in the SMA wire is related to its temperature and the external stress acting on the SMA wire. The SMA position controllers were mainly used for SMA characterization. The PWM controller was implemented for multiple joint motion. The heating time of each SMA wire, $t_i$, is computed using a PI controller given by Eq. 1 where $T^i_{set}$ and $T^i_{current}$ are the desired and the current temperature of the $i^{th}$ SMA wire, respectively. The gains, $K_p$ and $K_i$, can be adjusted according to system performance requirement. Thus, $t_i$ is given by:

$$t_i = K_p(T^i_{set} - T^i_{current}) + K_i \int (T^i_{set} - T^i_{current}) dt \quad (1)$$

By switching the current between SMA wires, multiple SMA wires can be actuated simultaneously using the same power supply.

For the vision-based feedback controller, a Micron Tracker (Claron Technologies Inc.) camera system was used. There were two markers on each straight segment. The tracking algorithm was implemented using Pyramidal Lucas-Kanade optical flow algorithm and OpenCV libraries. The works with sub-pixel accuracy and uses sum of squared intensity differences as measurement to minimize the errors for each tracking. A vector is drawn using the 3D location of two markers on each segment and the bending angle at each joint can be calculated by finding the angle between the vectors drawn on the connected segments. The heating time for the vision-based feedback controller is determined by replacing T with $\alpha$ in Eq. 1.

SMA Actuator Characterization

The SMA behavior can primarily be a function of stress, strain and temperature. Most of the constitutive models have been developed for quasistatic loading and at every instant the material is assumed to be in thermodynamic equilibrium. Stress is a function of temperature T, martensite volume fraction $\xi$, and strain $\epsilon$, the material constitutive equation (Equation B2) in the general form is given by Tanaka (K. Tanaka, "A thermomechanical sketch of shape memory effect: One-dimensional tensile behavior", *Res. Mechanica*, 18:251-263, 1986):

$$\sigma - \sigma_o = E(\xi)(\epsilon - \epsilon_o) + \Omega(\xi)(\xi - \xi_o) + \Theta(\xi)(T - T_o) \quad (2)$$

where $E(\epsilon, \xi, T)$ represents the modulus of material, $\Omega(\epsilon, \xi, T)$ is the transformation constant and $\Theta(\epsilon, \xi, T)$ is the thermal coefficient of expansion for the SMA material. The terms associated with subscript 'o' refer to the initial state of the material. The strain due to the thermal coefficient of expansion can be much lower than the strain due to the phase transformation and this coefficient is normally neglected.

As set forth in Equation B3, the elastic modulus is defined as:

$$E(\xi) = E_A + \xi(E_M - E_A) \quad (3)$$

As set forth in Equation B4, the phase transformation constant, $\Omega$, can be expressed as:

$$\Omega(\xi) = -\epsilon_L E(\xi) \quad (4)$$

where $\epsilon_L$ is the maximum recoverable strain. Liang-Rogers utilized the same constitutive relation and assumed a cosine function for the martensite volume fraction. In Liang-Rogers model (C. Liang, C. and C. A. Rogers, "One-dimensional thermo mechanical constitutive relations for shape memory material", *Journal of Intelligent Materials and Structures*, 1(2):207-234, 1990) during the martensite to austenite (M→A) transformation, $\xi$ is given by Equation B5:

$$\xi = \frac{\xi_o}{2}\{\cos[a_A(T - A_s) + b_A\sigma] + 1\} \quad (5)$$

where $a_A$, $b_A$ are constants defined in Equation B6 as:

$$a_A = \frac{\pi}{A_f - A_s}, \quad b_A = -\frac{a_A}{C_a} \quad (6)$$

and $C_a$ is called the stress influence coefficient. The stress influence coefficient quantifies the increase in transformation temperatures with applied stress.

Due to the two-antagonistic wire setup for each joint, the non-heated SMA wire will be naturally deformed by the heated wire. Therefore, the hysteresis of SMA behavior can be ignored and only the heating cycle needs to be characterized. To fully characterize the SMA wire, the transformation temperatures, the stress influence coefficient and the elastic modulus of each phase can be determined. These constants depend on the particular SMA wire used in the experiments and the annealing parameters (annealing time and annealing temperature). Hence, they can be determined experimentally.

To characterize the SMA wire, the experimental setup shown in FIG. 59 was used. The apparatus consists of a rotary encoder and a pin attached at a fixed distance, L, away from the center of the encoder. From the apparatus geometry, the relationship between encoder reading, $\theta$, and the radius of curvature, r, can be found using Eq. B7, where the origin, $k_1$, is defined as the location of the SMA fixer and $k_2(x,y)$ is the location of the encoder axis. There can be a cable connected to the SMA wire at point $k_5$ and it can be connected to the extension spring. Variable external loading can be applied on the SMA wire using the extension spring that is connected to the force sensor. The geometry of the setup is given in FIG. 16(*a*). During the experiments, a transparent box was also placed on top of the system to eliminate the effect of air flow in the room.

$$(L\cos\theta + x)^2 + (L\sin\theta + y - r)^2 = r^2 \quad (7)$$

A. Transformation Temperatures

To find the transformation temperatures of the heating cycle, $A_s$ and $A_f$, and determine the relationship between the strain (thus the bending angle) and temperature, the third variable, stress, should be kept constant. Initially, the SMA wire is at room temperature in the straight configuration. As the temperature of the wire is increased beyond $A_s$, the wire starts to transform to austenite phase and recovers its unstrained shape (arc) in the martensite phase. If an initially straight wire bent into the circular arc shape, as shown in FIG. 16(*b*), is considered, the relationship between strain and the arc radius can be derived as Equation B8:

$$\varphi\left(r + \frac{d}{2}\right) = l + \epsilon l \text{ and } \varphi = \frac{l}{r} \Longrightarrow r = \frac{d}{2\epsilon} \quad (8)$$

where, d, is the diameter of the SMA wire and l, is the length of the section of radius, r, and arc angle, $\phi$. When the SMA wire is straight, the radius of curvature is infinite. Since the strain is computed using the radius of curvature of the SMA wire, we start the analysis from $\theta=0$ degree.

Four experiments were carried out to find the strain-temperature relation of the SMA wire. A RTD sensor was attached at the center of a 2.1 cm SMA wire where the maximum deformation takes place. The RTD sensor was attached with a thermally conductive paste (OMEGATHERM® 201) to ensure good thermal contact between the sensor and the SMA wire. The temperature of the SMA wire was increased in steps and maintained at each temperature to ensure quasistatic deformation. FIG. 17 shows the corresponding strain-temperature relation obtained using Eqs. B7 and B8. The transformation temperatures $A_s$ and $A_f$ were determined to be 29.5° C. and 58.5° C., respectively.

B. SMA Parameters to Control the Strain in the SMA Wire

To investigate the behavior of the SMA wire under variable loading and find the stress related coefficients, the extension spring attached to the force sensor was used. As the SMA actuator transforms into its original shape, it pulls the cable connected to the extension spring and the force exerted by the spring can be recorded using the force sensor. During phase transformation, the location of the point $k_5$, where the cable is attached to the SMA, also changes. Let s be the distance between the origin (SMA fixer) and point $k_5$. Since for pure bending, the length of the wire remains unchanged; the location of point $k_5$ can be determined using Equation B9:

$$k_5 = (r\sin\beta, r(1-\cos\beta)) \quad (9)$$

where $\beta = s/r$. The direction of the force can be calculated by drawing a line between the point $k_5$ and $k_6$. The angle between the force vector and the x-axis ranges between 83.11-87.66 degrees. Since $\sin(83.11°) = 0.9928 \approx 1$, we can assume that the force acting on point $k_5$ is perpendicular to the motion of the SMA wire and we can hence characterize the SMA actuator using the maximum stress at point $k_5$ corresponding to the layer under tension. FIG. 18 shows that the external stress can be modeled as a straight line for this setup.

The unknown parameters $E_A$, $E_M$ and $C_a$ can be found by applying nonlinear regression analysis using the experimental data for temperature, strain and stress. It is important to note that the slope of the strain-temperature curve is mainly determined by $E_A$ and $C_a$ and different combinations of these parameters can fit the strain-temperature data. For example, if $C_a$ is small, high $E_A$ values are required to fit the experimental data. Therefore, a blocked force test was performed to find the upper bound on the elastic modulus in the austenite phase, $E_A$. To estimate $E_A$ an experimental setup described below was used to perform a blocked force test. In the blocked force test, strain in the wire is kept constant ($\epsilon-\epsilon_o=0$) and initially the SMA wire is in a stress free state ($\sigma_o=0$) at room temperature ($\xi_o=1$). Using these conditions and neglecting the thermoelastic stress contribution, the constitutive equation (Eq. B2) simplifies to Equation B10:

$$\sigma = -\epsilon_L E(\xi)(\xi-1) \quad (10)$$

where $\epsilon_L$ is the maximum recoverable strain $\epsilon_L = \epsilon_o$). At temperatures above $A_f$ the SMA wire is in the austenite phase ($\xi=0$) and the constitutive equation further simplifies to Equation B11:

$$\sigma = \epsilon_o E_A \quad (11)$$

FIG. 19 shows the change in the force generated by the SMA wire as temperature of the wire increases.

If only pure bending is assumed and the effect of shear stresses in the SMA wire is neglected, the stress in the SMA wire can be modeled using beam theory. For an SMA wire of length l and area moment of inertia I, the maximum stress can be related to the force, F, generated by SMA wire as Equation B12:

$$\sigma_{max} = \frac{Fl(d/2)}{I} \quad (12)$$

Using Eqs. B11 and B12, the maximum value that $E_A$ can take was determined to be 132.34 GPa. It is difficult to know where exactly the SMA wire contacts the pin that is attached to the force sensor. It was assumed that the force measured by the force sensor is concentrated at the tip of the SMA wire and hence it overestimates $\sigma_{max}$ (and hence the maximum value $E_A$ can take). This experiment shows that $E_A$ cannot be more than 132.34 GPa. To find the unknown parameters $E_A$, $E_M$ and $C_a$, a nonlinear curve-fitting approach using the least-squares method (lsqcurvefit function in MATLAB) was used. As set forth in Equation B13, the lower-bound and upper-bound for the coefficients were defined as:

$$[4,20000,60000] < [C_a, E_M, E_A] < [50,70000,132340] \quad (13)$$

The units for the parameters, $E_A$, $E_M$ and $C_a$, were defined as MPa, MPa and MPa/° C., respectively. The algorithm converged to parameter values [30,49960, 104720]. FIG. 20 shows the strain in the SMA wire and the strain calculated with the parameters that were found using lsqcurvefit.

If external stress is zero or known, the strain will only be a function of temperature. The temperature of the wire (and hence the strain) can be controlled using the PWM-based temperature controller. The constitutive model allows for the ability to find the corresponding strain at a particular temperature.

C. Geometric Relations

The bending (joint) angle was defined as the angle between consecutive links and the relationship between the bending angle and the arc angle, $\phi$, was examined since the arc angle is related to the strain. To find this relation, two small links were attached at the tips of the SMA wire and markers were placed on the links and the tracking algorithm was used to find the bending angle between the links (FIG. 21). FIG. 22 shows the relationship between the arc angle and bending angle. Corresponding data points for arc angle were calculated by evaluating the Liang-Rogers model using the temperature data points of the experiment. The polynomial curve fit ($R^2=0.99$) is given by Equation B14:

$$\alpha = 0.0001372\phi^3 - 0.01077\phi^2 + 0.976\phi + 0.7839 \quad (14)$$

where $\phi$ is related to strain by Equation B15:

$$\varphi = \frac{2\varepsilon l}{d} \quad (15)$$

For bending angles smaller than 20 degrees, the arc angle can be assumed to be equal to the bending angle as is approximately seen in FIG. 22.

D. Characterizing the Discretely Actuated Steerable Cannula

To prevent stress on the SMA wire in the machined slot, an SMA shape as shown in FIG. 23 was used. The effective part of the SMA wire which contributes to bending is the arc and the parts shown with dashed lines are straight and do not bend upon thermal actuation. This shape allowed for securing the SMA wire using the straight annealed part and prevented undesirable stress inside the slots, which can degrade the performance at each joint. The effective bending portion of the wire has the same radius of curvature (1.37 cm) as the SMA wire characterized herein and its length is determined by the distance between the two consecutive links. In one exemplary aspect, the bending angle ranges between +21°.

To find the strain vs. temperature relationship after the cannula was assembled, the temperature feedback controller was used to control the temperature of the SMA wire and recorded the resulting bending angles using the tracking algorithm discussed herein. The joint angle was started from −21° and at this position the heated SMA wire has maximum strain. Upon actuation it recovers the strain and reaches maximum joint limit in the positive direction. The bending angle is then converted to the strain in the SMA wire using the geometric relations described herein. The wire starts to bend at a higher temperature compared to the bare SMA wire because of the joint constraint and the soft sheath enveloping the joint. The overall effect of the antagonistic SMA wire and the sheath can be captured by selecting the transition temperatures $A_S$ and $A_f$ to be 31.5° C. and 64.5° C., respectively (FIG. 24). Any external stress can be substituted in Eq. B2 to find the change in strain (and thus the bending angle) with temperature.

Example C

A Discretely Actuated Steerable Probe for Percutaneous Procedures

An exemplary PWM-based controller was used to heat up SMA wires to a desired temperature. Another experiment was carried out inside gelatin to mimic the motion of the probe inside soft tissue. PWM control was successfully implemented, and local actuation of the steerable probe was demonstrated.

Technical Approach

A. SMA Annealing and Shape-Setting

Shape-setting of SMA is a thermally-induced process which can occur inside a furnace or via resistive heating with high current. SMA wires can be trained to form an arc shape upon thermal actuation. SMA can be shape-setted inside a small furnace to make sure temperature distribution is uniform along the length of the wire. 0.508 mm diameter SMA wires from Dynalloy, Inc. were used as SMA actuators. The composition of an exemplary SMA wire is 50% Ni-50% Ti and its transition temperature is 70° C. Upon heating above 70° C. the SMA wire returns to its original straight configuration. To train the SMA wire, it was first deformed into an arc shape and clamped down to keep it fixed. The temperature of the furnace was set to 52° C. and the fixture was placed inside the furnace when the temperature inside the furnace reached 52° C. Heat treatment can take roughly 15-20 minutes followed by forced convective cooling with a fan for 10-15 minutes until the ceramic fixture cools down to room temperature.

B. Steerable Probe

Figure 2:
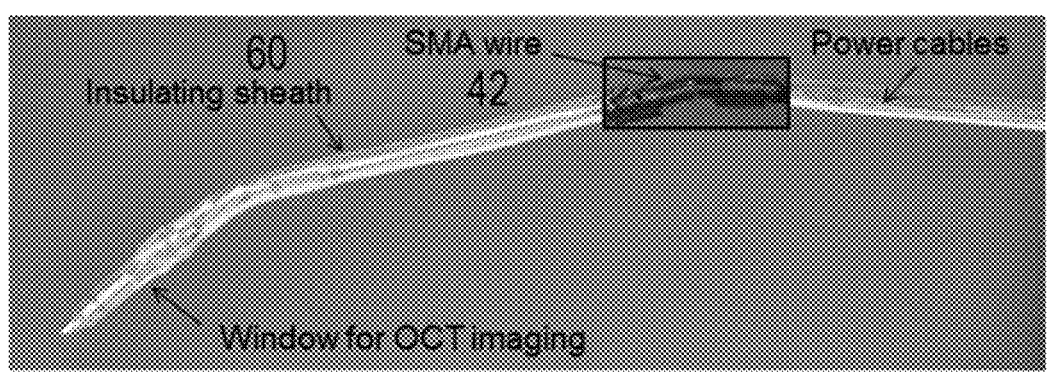
FIG. 2 is an image of an exemplary probe as disclosed herein.

SMA wires were mounted on the probe, which could be a needle or a hollow flexible steerable probe that can be guided to the target location by discrete actuation along the length of the probe to enable bending in the required directions. FIG. 2 shows the components of the design.

The probe can be composed of several discrete segments made of stainless steel connected by a short (and flexible) electrically non-conducting annulus. The connecting annulus is flexible but sufficiently rigid (hence semi-flexible) to transmit axial forces along the length and prevent bending due to insertion into soft-tissue. SMA actuator can be attached on the outer surface of the two parts and forms a connection between the two separate pieces of the probe connected by a electrically non-conductive material. Thus, the SMA actuators on the outer surface of the probe enable bending of the probe when the SMA is actuated. Since SMA is used primarily for actuation, the two ends of the SMA wire are not connected to the same metallic component otherwise no actuation will result. Hence the purpose of the intermediate material (semi-flexible annulus structure shown in FIG. 2) can be to ensure that the SMA actuation will take place and correspondingly result in the bending of the probe locally, which will allow the user to steer the probe to the appropriate target location. Since the straight segments were made of metallic components, only two joints could be actuated simultaneously as the consecutive joints needed to share one common electrical connection.

The components on the actual 2-DOF discretely actuated steerable probe can be controlled via temperature feedback from the thermocouples on the outer surface of the probe along with the SMA actuators. In this design, the outer diameter of the probe was 2.8 mm. In another aspect, the probe can involve a larger diameter to incorporate various elements on the interior surface of the probe to aid in imaging and control.

C. PWM Control

Recovery strain of SMA can be related to its temperature. Temperature can be used as a feedback signal to control the motion of the individual joints. To control the temperatures of SMA wires, PWM is used to supply current to heat up SMA wires. PWM control has proven to be an effective method for SMA actuation. PWM reduces energy consumption and it is robust to external disturbances. Besides these advantages, PWM is used to prevent overheat of SMA wires. Discrete on/off control signal is used to convert continuously supplied current into an equivalent PWM output command, which heats up the SMA wire to the desired temperature. For PWM control, Sensoray 626 DAQ card was used to generate digital on/off signal directly. By switching the current between SMA wires, both SMA wires can be actuated using the same power supply. Heating time of the SMA wires (t) is computed using a proportional controller given by Eq. C1.

The proportional gain (k) can be adjusted to change system performance. Temperature ($T_{current}$) of each SMA wire can be measured by thermocouples.

$$t = k(T_{set} - T_{current}) \tag{1}$$

An upperbound can also be set on the heating interval of SMA wires. When corresponding SMA wire is heated to desired temperature ($T_{set}$) or heating interval exceeds this upperbound, the control system switches to monitor the other SMA wire to prevent temperature drop. The controller stops sending control signal when the error is less than 0.5° C.

Experiments and Results

To verify the position control algorithm, two experiments were carried out. In the first experiment, both SMA wires were heated up to 50° C. using the PWM controller. A 2 Amps power supply was used to generate the PWM signal. The experiment was stopped after temperature of both joints reached steady state. Both wires reached steady state at 50° C. Both joints were actuated using PWM.

Another experiment was also carried out inside gelatin to mimic motion in tissue. Three packs of Knox Gelatine (Kraft Foods Inc.) were dissolved in cold water inside a 200 mL cup. Two cups of boiling water were added to the mixture and kept inside the refrigerator until it is fully hardened. Probe was inserted into the gelatin by hand and both SMA wires were simultaneously actuated and PWM control technique was used to obtain bending along the probe. This experiment shows that SMA wires can generate considerable amount of force to steer inside gelatin. During the experiments it has been noticed that the insulating sheath constrains the SMA during actuation and therefore limits the maximum achievable bending angle.

Example D

PWM-Based Temperature Tracking for Feedback Control of a SMA Actuator

In Ayvali and Desai (E. Ayvali and J. P. Desai, "PWM-Based Temperature Tracking For Feedback Control Of A SMA Actuator", *Journal of Intelligent Materials Systems and Structures* (in review)) pulse width modulation (PWM) was used as an effective method for SMA actuation, and it was shown to capable for use along with a compensator to control the temperature of the SMA. Using the constitutive model of the SMA, the desired temperature profile can be obtained for a given strain trajectory. A PWM-based nonlinear PID controller with a feed-forward heat transfer model was evaluated for use in a temperature-feedback system for tracking a desired temperature trajectory. The PWM-based controller was used during the heating phase of the SMA actuator and was effective in tracking step-wise and continuous trajectories.

The behavior and the properties of SMA depend on the temperature and the stress acting on it. Phase transformation, heat transfer and changes in stress and temperature of the SMA material are highly nonlinear. These nonlinear characteristics present difficulties in designing control systems to control the SMA actuators. Most of the work on SMA modeling and control has concentrated on straight annealed SMA wires and springs whereby the phase transformation results in linear motion. The general approach to controlling the SMA is to directly measure the position of the SMA actuator and use a bias spring or a linear actuator to apply forces on the SMA actuator during cooling to compensate for the hysteresis. Then, the strain and the force measurements are fed back to the control loop to generate control inputs using the proposed controllers. Tracking a desired trajectory is more difficult than controlling the position of the SMA actuator due to the nonlinear nature of the SMA.

When SMA is used as an actuator in a compact device, actuating the SMA actuator(s) becomes a further challenge. Direct measurement of strain and controlling the forces acting on the SMA become impractical. Electrical resistance of the SMA wire changes during phase transformation and Ikuta et al [K. Ikuta, M. Tsukamoto, and S. Hirose, "Shape memory alloy servo actuator system with electric resistance feedback and application for active endoscope", In 1988 *IEEE International Conference on Robotics and Automation*, volume 1, pages 427-43, April 1988) used resistance feedback to control the position of the SMA actuator. This is an attractive approach since the electrical resistance is an internal parameter and its measurement does not require an additional sensor. However, SMA has a low resistance and most of the work that implement resistance feedback use 22-100 cm length SMA wires or multiple SMA wires that are connected in series to increase resistance of the SMA wire. The resistance change of a 2 cm SMA wire that is annealed in the disclosed example is less than 0.1Ω. Therefore, using a resistance feedback approach can have poor resolution for the chosen length of SMA wire in this application. Temperature-feedback presents a powerful approach to control the strain in the SMA wire using the constitutive model of the SMA. The constitutive model describes the relationship between the stress, strain and the temperature of the SMA actuator. Temperature-feedback can be used with a PWM controller for SMA actuation. PWM was proposed for SMA actuation by Ma and Song (N. MA and G. Song, "Control of shape memory alloy actuator using pulse width modulation", *Smart Materials and Structures*, 12: 712-719, 2003) and it is an efficient way to actuate the SMA and can be used to control the temperature of the SMA wire along with a linear compensator such as PI, PD, or PID. SMA is a natural low pass filter and is not disturbed by the switching of the input power. PWM can be easily implemented using hardware or software and it is robust to external disturbances. PWM also enables multiple SMA actuations simultaneously using a single power supply. The relationship between the temperature of the SMA wire, strain and the external stress was modeled using the constitutive model of the SMA and it was demonstrated that the strain of the SMA wire can be indirectly measured using the constitutive model. This enables the use of temperature-feedback to control the strain in the SMA actuator. The constitutive model relates the desired strain trajectory to a desired temperature trajectory.

Disclosed herein is an example of controlling the strain of the SMA actuator with temperature-feedback to control the tip motion of the discretely actuated steerable cannula shown in FIG. 5. The cannula is composed of straight segments connected by SMA actuators that generate local bending at discrete locations along its length. To control the position of the cannula, a combined image guided control and a model based temperature-feedback control is described. A PWM-based vision feedback controller was developed as the cannula can be steered with image guidance in a MRI, CT, or ultrasound imaging environment. This work focuses primarily on the temperature-feedback aspect of the combined controller. When the image feedback from the imaging modality is not optimal, the controller can switch to the temperature-feedback controller. In this combined approach, the bending angle (strain) is measured by the imaging modality and the temperature is measured using the temperature sensor. When the strain and the temperature of the SMA actuator are known, the external stress acting on the SMA can be found using the constitutive model of the SMA. Therefore, temperature-feedback can also be used to sense the external forces acting on the cannula as the cannula is steered inside the soft tissue.

In trajectory planning, repeated switching between antagonistic actuators increases the temperature of the two SMA actuators which in return increases the elastic modulus. The elastic modulus of the high temperature austenite phase is 1.5-2 times higher than that in the martensite. Therefore, the actuated SMA wire also can overcome the high mechanical resistance of the unactuated SMA wire. When one of the actuators is actuated the other one is naturally deformed. If the bending direction needs to be reversed, the controller switches to the antagonistic SMA actuator once the actuated SMA wire is cooled to the martensite phase. This approach increases the execution time of a joint trajectory. However, there is no need to model the hysteresis loop in this approach and this simplifies the control problem. Minimum number of switching between the actuators can be given as a constraint in trajectory planning and hence switching between the actuators can be minimized.

Herein, a PWM-based nonlinear PID controller with a feed-forward heat transfer model is described to utilize temperature-feedback for tracking a desired temperature trajectory. Constant gain controllers can result in high errors as the temperature of the SMA wire increases. It can be important to investigate the heat loss and the relation between the supplied power to the SMA wire and the corresponding maximum temperature that can be reached. The relation between the duty cycle of the PWM controller and the corresponding maximum temperature that can be achieved needs to be modeled to implement a feed-forward term that compensates for the heat loss.

Materials and Methods

A. Arc-Shaped SMA

The SMA actuator was a 0.5334 mm diameter drawn nitinol (manufactured by Memry, Inc.) wire and has 2.1 cm length. The SMA wire was deformed into an arc shape and clamped down to a ceramic fixture during annealing. Heat treatment takes 40 minutes followed by quenching the SMA in a ice-water mixture. After the annealing process is completed, the SMA has one-way shape memory and upon heating the SMA above its transition temperature, the SMA can transform into the desired arc shape. If an initially straight wire bent into the circular arc shape is considered, the relationship between strain and the arc radius can be derived as Equation D1:

$$\varphi\left(r + \frac{d}{2}\right) = l + \varepsilon l, \varphi = \frac{l}{r} \Longrightarrow r = \frac{d}{2\varepsilon} \quad (1)$$

where, d, is the diameter of the SMA wire and l, is the length of the section of radius, r, and arc angle, φp. The original arc shape has 1.37 cm radius of curvature and straight configuration corresponds to 0.0195 (1.95%) strain.

Most of the research in SMA characterization and modeling are done on straight annealed SMA wires and springs. There is not much work done in modeling and control of SMA actuators that are annealed in an arbitrary shape. When a commercially available straight annealed SMA wire is used, its mechanical, electrical and thermal properties are available from the manufacturer. The drawn nitinol does not exhibit shape memory effect prior to the annealing. The mechanical, electrical and thermal properties of the SMA wire need to be determined after annealing. The uniaxial testing devices and experimental setup used in characterizing straight annealed SMA wires are not applicable when the SMA wire is annealed in an arbitrary shape. For example, measuring the elastic modulus in the austenite phase is not possible using the conventional tensile testing machine since the SMA wire does not move along a line and it moves in a plane as the temperature of the SMA increases. A characterization procedure has been presented to find the parameters of the SMA. Such an arc shape SMA can then be used in a robotic device to generate joint torques. The arc-shaped design expands the application areas for the SMA.

B. Experimental Setup

To measure the strain in the SMA, an experimental setup using the apparatus described below was used. The apparatus consists of a rotary encoder and a pin attached at a fixed distance, L, away from the center of the encoder. Initially, the SMA wire was at room temperature in the straight configuration. As the SMA wire transforms from the straight configuration to an arc shape, it pushes the pin. The rotation of the pin is recorded using the encoder. From the apparatus geometry, the relation between encoder reading and the radius of curvature can be found using Equation D2 (below). The geometry of the setup is shown in FIG. 25. The location of the encoder pin is shown as (x,y). When the SMA wire is straight, the radius of curvature is infinite. Since the strain is computed using the radius of curvature of the SMA wire, the analysis starts from θ=0° (see FIG. 26). There is a cable connected to the SMA wire and it is routed around a screw. The cable can be connected to a mass via the pulley to apply constant loading or it can be connected to the extension spring to apply variable loading.

$$(L \cos \theta + x)^2 + (L \sin \theta + y - r)^2 = r^2 \quad (2)$$

C. Constitutive Model

Stress, strain and temperature are the three variables that are used to describe the SMA behavior. Constitutive models are commonly developed for quasistatic loading assuming that the material is in thermodynamic equilibrium. Tanaka (K. Tanaka, "A thermomechanical sketch of shape memory effect: One-dimensional tensile behavior", *Res. Mechanica*, 18:251-263, 1986) modeled the strain, c, temperature, T, and martensite volume fraction, ξ, as the only state variables. The constitutive equation (Equation D3) is given as:

$$\sigma - \sigma_o = E(\xi)(\epsilon - \epsilon_o) + \Omega(\xi)(\xi - \xi_o) + \theta(\xi)(T - T_o) \quad (3)$$

where $E(\epsilon, \xi, T)$ represents the elastic modulus, $\Omega(\epsilon, \xi, T)$ is the phase transformation tensor and $\theta(\epsilon, \xi, T)$ is thermal coefficient of expansion for the SMA material. The strain due to the thermal coefficient of expansion is neglected since it is much lower than the strain due to the phase transformation. The terms associated with subscript 'o' refer to the initial state of the material. As set forth in Equation D4, the elastic modulus is defined as:

$$E(\xi) = E_A + \xi(E_M - E_A) \quad (4)$$

The phase transformation constant, Ω, can be expressed as Equation D5:

$$\Omega(\xi) = -\epsilon_L E(\xi) \quad (5)$$

where $\epsilon_L$ is the maximum recoverable strain. A cosine function was used for the martensite volume fraction. During the martensite to austenite (M→A) phase transformation, ξ, is given by Liang and Rogers (C. Liang, C. and C. A. Rogers, "One-dimensional thermomechanical constitutive relations for shape memory material", *Journal of Intelligent Materials and Structures*, 1(2):207-234, 1990), as set forth in Equation D6:

$$\xi = \frac{\xi_o}{2} \{\cos[a_A(T - A_s) + b_A \sigma] + 1\} \quad (6)$$

where $a_A$, $b_A$ are constants defined by transformation temperatures and the stress influence coefficient. The experimental setup described above was used to characterize the SMA wire.

Martensite volume fraction determines the shape of the temperature-strain curve. The shape of the curve that describes the change in martensite volume fraction with temperature is independent of the SMA phase transformation phenomena and its dependence on stress. Depending on the SMA material used, this curve can be represented with a cosine expression or an exponential expression. Tanaka used an exponential function for the martensite volume fraction, ξ. During the phase transformation from the martensite phase to the austenite phase (M→A), ξ is given by Equation D7:

$$\xi = e^{a_A(A_s - T) + b_A \sigma} \quad (7)$$

FIG. 27 shows that an exponential expression provides a better fit than the cosine expression for the martensite volume fraction as the wire is heated. Hence, the exponential expression for the martensite volume fraction can be used. The properties of the SMA actuator are given in Table D.1.

TABLE 1

Material and physical properties of the SMA

| Parameter | Value |
| --- | --- |
| $E_A$ | 104.31 GPa |
| $E_M$ | 48.69 GPa |
| $C_a$ | 30 MPa/° C. |
| $A_s$ | 39.5° C. |
| $A_f$ | 64.5° C. |
| d | 0.5334 mm |
| r | 1.37 cm |

D. Thermal Modeling

The heat transfer properties of the SMA can be determined to find the relation between the current supplied to the SMA and the temperature of the SMA. Heat transfer equation of SMA is commonly defined in terms of input power to the SMA and it depends on the specific heat and the convection coefficient of the SMA. Digital signal calorimetry (DSC) measurement is required to find the specific heat of the SMA. The convection heat transfer coefficient is commonly calculated using the empirical relationship for heat transfer over a horizontal or vertical cylinder based on the configuration of the SMA wire. The shape of the SMA actuator changes during phase transformation and a fixed cylindrical geometry assumption cannot be used as in straight SMA wires. It has been shown that temperature-current relation of SMA can be represented with an empirical relation of Equation D8, as follows:

$$T(t) = T_\infty + \frac{a_1}{a_2} IR(1 - e^{-a_2 t}) \quad (8)$$

where I is the current supplied to the SMA, R is the electrical resistance of the SMA, $a_1$ and $a_2$ are the parameters to be determined through experiments. The resistance change of the SMA actuator during phase transformation is less than 0.1Ω and it is assumed to be constant. The term $$\frac{1}{a_2}$$

is the time constant and $$\frac{a_1}{a_2}$$

IR represents the steady-state value. The temperature-current relationship depends on the SMA material used and the dimensions of the SMA actuator. Therefore, the constants $\alpha_1$ and $\alpha_2$ are also material dependent.

E. PWM-Based Nonlinear PID Controller

PWM is implemented with a switching circuit. Sensoray 626 DAQ card generates a digital on/off signals to control the solid state relays (SSRs). The maximum turn-on time of the SSR is 50 µs and the maximum turn-off time is 300 µs. The discrete on/off control signal converts the continuous current into an equivalent PWM output signal. The heating time of the SMA wire, Δt, in a heating period, P, is computed using the desired control law. Duty cycle is defined as Δt/P. During the interval Δt, the switch for the selected SMA wire is closed and current is supplied for Δt milliseconds. Once the interval is over, the switch is opened until the end of the period, P. The controller can switch to other SMA wires once the heating time of the actuated SMA wire is completed. Therefore, multiple SMA wires can be actuated in the same period.

A cubic term can be added to PID and using a PID-P³ controller to reduce the settling time and overshoot of the SMA. For a small error, the cubic term vanishes and the controller works as a regular PID controller. A nonlinear PID (NPID) controller that has a quadratic and a cubic term can also be introduced. When the error is small, the cubic term tends to vanish but the quadratic term still produces a nonlinear control effort. As the temperature of the SMA wire increases, the steady-state error increases due to increased heat loss and nonlinear dynamics of the SMA actuator. A NPID controller with a feed-forward term given by Equation D9 can be used to calculate the heating time of the SMA actuator. $\Delta t_h$ is the feed-forward term and it represents the minimum heating time that is required to reach a desired temperature. The feed-forward term compensates for the heat loss. The integrator is adaptive and depends on the desired temperature of the SMA wire, $T^d$, to improve the steady-state response.

$$\Delta t = K_P e + K_D \dot{e} + K_I (T^d) \int e + K_T (e^2 + e^3) + \Delta t_h \quad (9)$$

In Equation D9, $K_P$, $K_D$, $K_I$ and $K_T$ are the coefficients of the PID controller and e is defined as the difference between the desired and the current temperature of the SMA wire. FIG. 28 shows the block diagram of the controller. The blocks that are inside the dashed line are implemented in software. The PWM signal is implemented in the software. The algorithm runs on WINDOWS® XP at 500 Hz to obtain high resolution PWM signal.

Experiments and Results

A. Thermal Modeling

To model the relationship between the temperature and the current supplied to the SMA actuator, different current inputs are applied to the SMA wire. To ensure good thermal contact between the RTD sensor and the SMA wire, a thermally conductive paste (OMEGATHERM® 201) was used. FIG. 29 shows the temperature profiles obtained from the experiments. The parameter $\alpha_2$ in Equation D8 was set to 0.047 and the steady-state temperature values obtained from the experiments were compared to the steady-state term in Equation D8. The parameter $\alpha_1$ can be determined by a linear relation in I as Equation D10:

$$\alpha_1 = 49.1 I + 18.6 \quad (10)$$

PWM has a high energy density. PWM results in a faster response and a higher steady-state temperature compared to continuously supplying the average current value. For instance, a 2A PWM signal with 50% duty cycle results in a faster response and a higher steady-state temperature compared to continuously supplying 1A. FIG. 30 shows the temperature profiles for different period and heating time values for 2A current. Period values between 50 ms-500 ms were tested. A smaller period value may lead to system instability and a high value may result in temperature drop when the current is off. The effect of period P can be neglected in this range and only the duty cycle $$\frac{\Delta t}{P}$$

is important. This shows that if more than one SMA wire needs to be actuated, a longer period can be selected to monitor all the wires in the same period. As set forth in Equation D11, a relation similar to Equation D8 can be defined to obtain the temperature profile using PWM:

$$T(t) = T_\infty + \frac{a_1}{a_2} IR\left(\frac{\Delta t}{P} I\right)(1 - e^{-a_2 t}) \quad (11)$$

The difference between Equations D8 and D11 is the addition of the $$\left(\frac{\Delta t}{P} I\right)$$

term. FIG. 31 shows the temperature profiles for different current inputs and heating times for P=200 ms. Using R=0.35Ω and setting $\alpha_2$=0.047 results in Equation D12:

$$a_1 = 7.99 e^{-5.417 \frac{\Delta t}{P} I^2} + 3.413 e^{0.112 \frac{\Delta t}{P} I^2} \quad (12)$$

A linear relationship can be obtained for $a_1$ as in Equation D10 if a constant current is used. FIG. 32 shows the relation between the desired increase in temperature, ΔT, and the PWM input parameter $$\left(\frac{\Delta t}{P} I^2\right).$$

The temperature change is used instead of the final steady-state temperature since the ambient temperature, $T_\infty$, might be different for each experiment. The linear fit given by Equation D13 was obtained from FIG. 32 and it is used to determine the minimum heating time, $\Delta t_h$, that is required to reach the desired temperature.

$$\left(\frac{\Delta t_h}{P}I^2\right) = 0.05515\Delta T - 0.16978 \tag{13}$$

B. PWM-Based NPID Controller

The parameters of the controller were set to $K_p$=55, $K_D$=45000, $K_I$=0.0001$T^d$, $K_T$=700. The following conditions were implemented in the algorithm:

Until the temperature of the SMA actuator is within 1° C. of the initial value of the temperature profile, the integral term ($K_I(T^d)\int e$) is not used.

The minimum pulse width is limited by the heat transfer model: $\Delta t_{min}=\Delta t_h$ The maximum pulse width is limited to $\Delta_{max}=\Delta t_{min}+20$ Initially, the pulse width calculated using the heat transfer model is used to heat up the actuator until the temperature is within 2° C. of the desired temperature: $\Delta t=\Delta t_h$ if e>2° C.

The pulse width is set to 0.2 times the minimum pulse width if there is an overshoot (rather than turning the current off): $\Delta t=0.2\Delta t_h$ if e<0° C.

Initially heating the SMA wire with a duty cycle calculated using Equation (13) prevents overheating. It also limits the strain rate. A high strain rate causes internal heating and increases the temperature of the SMA wire reducing the reliability of the constitutive model. The quasistatic loading rate can be assumed to be 0.0005 s$^{-1}$. To satisfy quasistatic loading 0.0195 strain (straight configuration to maximum curvature) can be recovered in more than 39 seconds. This corresponds to approximately 1.6° Cs$^{-1}$. Note that the response time of the SMA actuator can be substantially increased. Fast response is not a crucial requirement for a surgical procedure and high strain rates corresponds to a quick deformation and tearing of the tissue. If a faster response is required, the effect of strain rate on the temperature needs to be taken into account in the constitutive model. The feed-forward term determines the minimum and the maximum heating times for a desired temperature. This is similar to variable structure control. The desired temperature controls the sliding surface and the boundary layer can be determined by $\Delta t_h$. When the initial value for the desired temperature profile is much higher than the temperature of the SMA wire, the integral term accumulates until the temperature of the wire reaches the desired value. This initial heating period results in overshoot due to large values in the integral term. Therefore, the integral term is not used until the temperature of the SMA actuator reaches the initial value of the temperature profile. The feed-forward term can be used to guarantee that the temperature of the SMA actuator reaches within a close range of the desired temperature. When the desired temperature is updated, initially the error is large. Setting a limit to the maximum pulse width limits the initial rate of temperature increase. When the temperature of the SMA actuator exceeds the desired temperature, the current is not shut-off completely. Stopping the current flow resulted in sudden temperature drop and caused chattering in the control signal. The minimum current supplied to the SMA actuator can be low enough to let the SMA wire cool down but high enough to compensate for the heat loss and prevent sudden temperature drop. The limits for the minimum and maximum pulse width are defined as a function of $\Delta t_h$ since heat loss increases with increasing temperature. The gains of the NPID controller are selected by trial and error.

To evaluate the performance of the controller a step-wise input was given as a reference. FIG. 33 showed the performance of the controller in tracking the reference. The RMS steady-state error was 0.0551° C. The errors were calculated in the intervals between the time at which SMA actuator reached the desired temperature and the time a new command was sent. Tracking a continuous trajectory increases the complexity of the system, since the desired path is continuously changing. Tracking of continuous temperature profiles can be achieved by sampling the desired temperature trajectories. FIG. 34 shows a 6th and a 7th order polynomial reference. The desired temperature is sampled at 2 second intervals. Phase transformation of SMA is a heat driven process and the response of the SMA actuator is slow. For 1° C. increase, the response time of the SMA actuator is approximately 2 seconds. Using a higher sampling rate for the reference signal may be preferable, but it is not required. The RMS errors for the 6th and 7th order polynomial trajectories are 0.1472° C. and 0.1262° C., respectively. The controller shows great performance and it can not only track step inputs but also continuous trajectories.

Two different experiments were carried out to evaluate the strain using the constitutive model. The experimental setup described in this example was used and strain was calculated from the encoder readings. FIG. 35 shows a step-wise reference temperature command and the temperature of the SMA actuator. FIG. 36 shows the change in strain of the SMA actuator and the strain predicted by the constitutive model. A 7th order polynomial temperature reference was also applied and FIG. 37 shows the change of temperature. The change in strain of the SMA actuator is given in FIG. 38. The RMS errors for the strain trajectories in FIG. 36 and FIG. 38 were 3.4479×10$^{-4}$ and 2.3455×10$^{-4}$, respectively. A continuous temperature profile results in a smooth change in strain.

Example E

Towards a Discretely Actuated Steerable Cannula for Diagnostic and Therapeutic Procedures A multi-degree-of-freedom discretely actuated steerable cannula with shape memory alloy (SMA) actuators was evaluated. A pulse width modulation (PWM)-based control scheme was implemented to control all SMA actuators simultaneously to enable multiple joint motion using a single power supply. The exemplary controller was validated through an experiment inside gelatin to mimic the motion of the cannula inside a medium which requires a significant amount of force to move the joints of the cannula. Trajectory planning using a suitable metric and trajectory execution were implemented. To demonstrate the delivery of a diagnostic tool through the cannula, an optical coherence tomography (OCT) probe was passed through the cannula and performed in situ micro-scale imaging.

Described herein is a discretely actuated steerable cannula that could be used in percutaneous and intravascular procedures where diagnostic and therapeutic capabilities may be required. SMA actuators can be used for actuation along the length of the probe (the probe can be a needle or a cannula) to generate appropriate controlled motion at each joint along the steerable cannula. The ability to control the bending angle locally enables a small radius of curvature in trajectory planning. The SMA wires can be annealed through a customized annealing process to generate bending forces.

Materials and Methods

The design and evaluation of the discretely actuated steerable cannula has multiple steps. First, the SMA annealing process and the cannula design are described. Then, the two control strategies adopted for the position control of the SMA actuators, namely PWM-based temperature feedback and PWM-based vision feedback control, are described. An optical flow algorithm was used for the implementation of the vision-based feedback controller and hence the algorithm was introduced prior to the description of the vision-based feedback controller.

A. Annealing of Shaped-Memory Alloys

The SMA actuator used for annealing is a 0.508 mm diameter Flexinol® (Dynalloy, Inc.). One consideration before annealing is to select the desired radius of curvature of the SMA wire. If an initially straight wire bent into a circular arc shape was considered, the relation between strain and the arc radius can be written as Equation E1:

$$r = \frac{d}{2\epsilon} \qquad (1)$$

where $\epsilon$ is the strain in the wire, d is the diameter of the SMA wire and r is the arc radius. Nitinol can recover strains of up to 8% for low-cycle use or up to about 2.5% strain for high-cycle use. If these values are used as a guideline for a 0.508 mm diameter SMA wire, 2.5% strain corresponds to a 10.16 mm radius of curvature. A radius of curvature above 10.16 mm has a strain smaller than 2.5%, thus satisfying this requirement. For a given length of the SMA wire, a smaller arc radius corresponds to a larger bending angle. Another consideration is the transformation temperature range (the difference between the temperature at which the SMA starts to deform and the temperature at which the transformation is complete). A wider transformation range increases the resolution of the bending angle. The smaller the transformation range, the higher the resolution that is required for the temperature controller, since a small temperature fluctuation can result in a large change in the bending angle. Achieving the desired transformation temperature is not trivial. The transformation temperatures of the annealed SMA wire depend on various factors such as the percentage of Nickel and Titanium, the level of cold work, the annealing time and annealing temperature. Among these factors, the annealing time and annealing temperature can be varied by trial and error to achieve the desired transformation temperatures. The proper selection of a sheath that covers the SMA actuators for heat insulation would relax the requirement on the maximum allowable transformation temperature for a medical procedure. Due to the characteristics of the SMA actuator, it has a one-way shape-memory effect after the annealing process is completed. Upon heating the SMA above its phase-transition temperature (martensite to austenite phase), the SMA transfers to the desired arc shape. Cooling down the SMA wire causes a transformation from austenite to twinned martensite without any shape change. Therefore for each joint, antagonistic SMA wires can be used for bending in either direction.

A small furnace was used to anneal the SMA wire. The SMA wire is first deformed into an arc shape and clamped down to ceramic to keep it fixed. In the ceramic fixture, bolts were used to secure the SMA wire and positioned such that the radius of curvature is near 15 mm. A 15.64 mm radius of curvature was obtained, and that corresponds to 0.01624% strain. Heat treatment of the SMA takes about 40 min followed by forced convective cooling with a fan for 10-15 min until the ceramic fixture cools down to room temperature.

B. Cannula

Figure 1A:
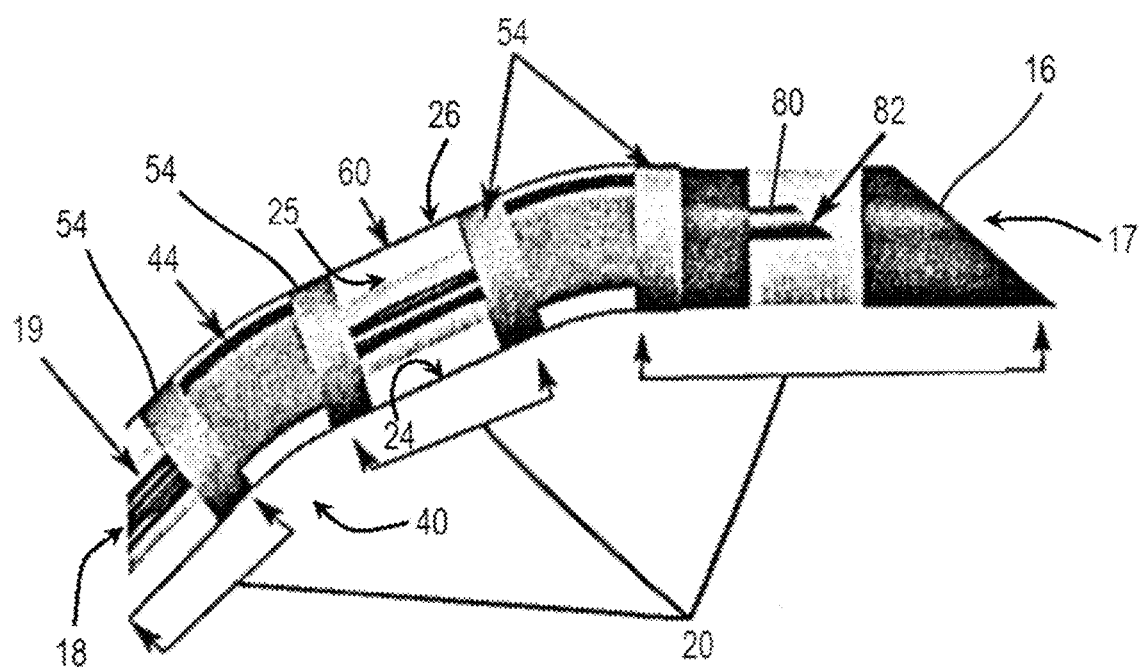
FIGS. 1A and 1B depict schematic, partially transparent views of exemplary probes as disclosed herein.
Figure 1B:
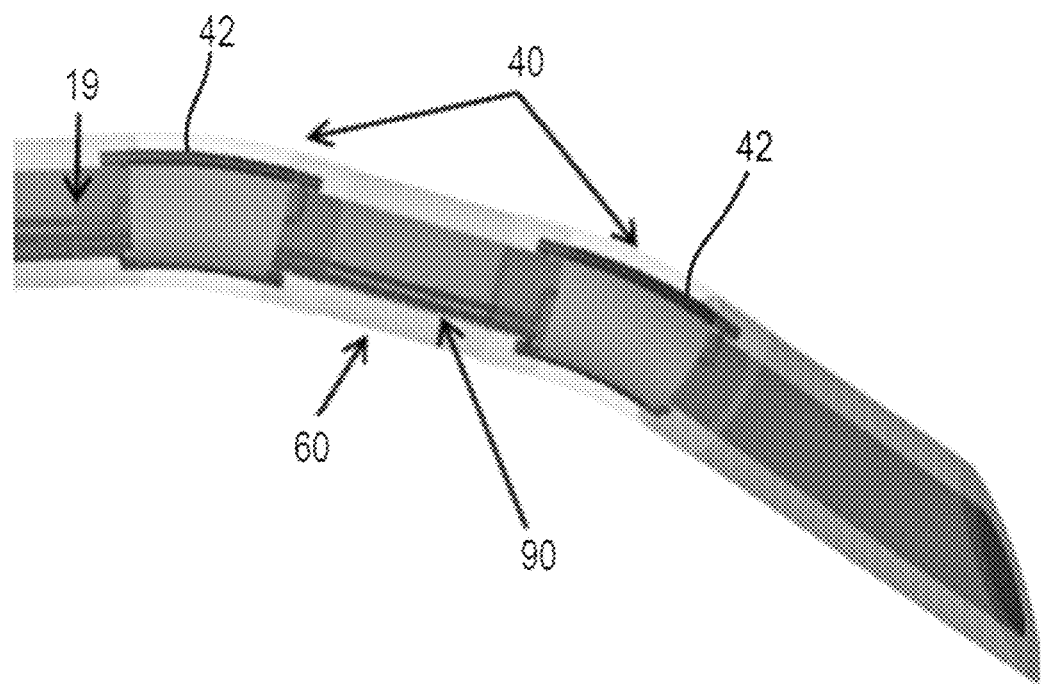

The discretely actuated steerable cannula was made of three straight segments that are connected by SMA actuators. The straight segments had a 1.4 mm inner diameter (ID) and a 1.65 mm outer diameter (OD). The two ends of the SMA wires were connected on the outer surface of the straight segments to enable bending of the probe when the SMA is actuated. There was 1 mm clearance between the adjacent links to prevent short-circuit and the sheath annulus structure and the SMA actuators that join the straight segments were rigid enough to prevent bending during insertion into the soft tissue. The SMA wires were attached mechanically by crimping the wire at the tips via use of stainless steel rings and enamel-coated wires were wrapped around the tip of the SMA wires for electrical connection. FIG. 1 shows the components of the cannula. After the assembly, the cannula had 1.4 mm ID and 3 mm overall OD. The lengths of each segment from the base to the tip are 6.05 cm, 4.05 cm and 3.05 cm, respectively. The length of each segment was defined as the length of the individual segment plus half of the clearance between the segments (0.5 mm).

An exemplary discretely actuated steerable cannula is described herein. SMA actuators can be placed such that bending in different directions can be achieved. The hollow inner core of the cannula enables the delivery of both diagnostic and therapeutic tools to the appropriate location. An imaging window was also employed in the exemplary design to demonstrate the probe's use as a diagnostic tool for OCT imaging. It is important to note that, upon thermal actuation, bending occurs locally at the SMA location (the connection between two consecutive links) which can be advantageous for local steering, thereby enabling a small radius of curvature.

C. Pose Tracking Using Optical Flow

A Micron Tracker (Claron Technologies Inc.) camera system was used for stereo imaging. To find the pose of the cannula, six markers were placed on the two-degree-of-freedom (2-DOF) prototype. There were two markers on each segment. The tracking algorithm was implemented using a pyramidal Lucas-Kanade optical flow algorithm and OpenCV libraries. The algorithm uses sum-of-squared intensity differences as measurements to minimize the errors for each tracking and works with sub-pixel accuracy.

To register the initial configuration, six markers were clicked on the screen via a mouse on the images acquired from the left and right cameras at 15 fps. The 3D locations of the markers was calculated by triangulating the 2D location of the markers on left and right images. The pixel coordinates are then transformed into camera coordinates. A vector was drawn using the location of two markers in each segment and the bending angle at each joint is calculated by finding the angle, $\alpha_i$ (i=1, 2), between the vectors drawn on the connected segments.

D1. Shape-Memory Alloy Position Control

There have been various approaches for controlling SMA actuators. There are primarily three feedback options for closed-loop control of SMA actuators: position, temperature and electrical resistance. Among these, direct measurement of strain can be challenging and impractical for compact designs where limited space is available. Using electrical resistance of the SMA is attractive for feedback control since it is an internal parameter and does not require an additional sensor. Recovery strain of SMA can be related to temperature, and the temperature of the SMA can also be used as a feedback signal to control the strain generated during phase transformation. Sensorless control of the SMA that does not rely on feedback, but instead depends on mathematical models to estimate the SMA strain has also been used for controlling SMA. Curve-fitting models treat the SMA as a black box and depend on the particular SMA actuator or setup used in developing the models. If the SMA actuator has to work in an environment different from the setup that was used to characterize it, the model may no longer be valid. Among these approaches, using a constitutive model based on temperature feedback can be advantageous since only offline parameters need to be changed and these parameters can be obtained in advance through experiments. If the annealing parameters or the radius of curvature of the SMA actuator need to be changed, the model can still be used by modifying the offline parameters.

PWM has proven to be an effective method for SMA actuation. A PWM-based controller can enable multiple joint motion simultaneously using a single power supply. PWM was implemented via use of a switching circuit. Two solid-state relays (SSRs) were used as switches and a Sensoray 626 DAQ card generates digital on/off signals to control the switches. The discrete on/off control signal was used to convert continuously supplied current into an equivalent PWM output command to heat up the SMA wires.

Two PWM-based controllers were developed. One of the controllers was a PWM-based vision feedback controller and the other was a temperature-based feedback controller. The vision-based controller was developed as it can enable image-guided control of the cannula in MRI, CT, or ultrasound imaging environments. In one exemplary aspect, stereo vision can be used as the main feedback for position control of the cannula. Image-guided control can be combined with a temperature feedback controller so that the controller can switch to the temperature feedback controller when the image feedback from the imaging modality is not optimal.

D2. Vision-Based Feedback

Using the Micron Tracker camera system and the tracking algorithm, the difference between the desired angle and the current angle can be updated at each frame. The heating time of each SMA wire, t, is computed using a proportional controller given by Equation E2 (below) where $\alpha^i_{set}$ is the desired bending angle for joint i, and $\alpha^i_{current}$ is the current joint angle of joint i. A control command, $t_i$, represents the interval in which the switch for the selected SMA wire is closed and current is supplied to the corresponding SMA wire for $t_i$ seconds. The heating times are updated at each frame and the proportional gain, k, can be adjusted based on the task requirement.

$$t_i = k(\alpha_{set}^i - \alpha_{current}^i) \quad (2)$$

The control scheme can be described as follows: at each frame, the position error for the first and second joint are calculated using the stereo image couples and the corresponding $t_1$, and $t_2$ values are updated. The first joint is then actuated for $t_1$ seconds and after this interval is over the corresponding switch of the first joint is opened and the switch for the second joint is closed to actuate the second joint for $t_2$ seconds. By switching the current between SMA wires, both SMA wires can be simultaneously actuated with the same power supply. The heating interval, t, is limited to an upper value $t_{max}$, to ensure that both SMA wires are monitored in each heating cycle, T.

D3. Temperature Feedback

To control the temperatures of SMA wires, the same approach can be applied and PWM can be used to supply current to heat the SMA wires. A mini resistance temperature detector (RTD) sensor (Alpha Technics) can be used to measure the temperature of the SMA wire. The heating time is given by Equation D3, where $T^i_{set}$ is the desired temperature for SMA actuator i, and $T^i_{current}$ is the current temperature of the SMA actuator at joint i.

$$t_i = k(T_{set}^i - T_{current}^i) \quad (3)$$

The SMA transformation is a heat-driven process and therefore its response time is limited. By increasing the current input to the SMA actuators, the response time can be improved. PWM is mainly used to drive the SMA actuators and the heating interval of each actuator is determined by the vision-based feedback and the temperature feedback controllers. In the vision-based feedback controller, the bending angle can be directly measured and that can be used to generate the appropriate control signal to actuate a particular SMA, while in the temperature-based feedback controller, the strain in the SMA wire can be correlated with the temperature as well as the external stress acting on the SMA through the constitutive model of the SMA. The constitutive model of the SMA eventually provides the correlation between the temperature of the SMA wire and the bending angle. The controllers described in this section were used to characterize the SMA actuator.

Experiments and Results

The performance of the PWM-based controllers that were used for characterizing the SMA actuators was evaluated. The constitutive model used for modeling the phase transformation of the SMA material is introduced next along with the details of the SMA characterization procedure. A blocked force test was used to find the maximum force that can be generated by the SMA actuator. A test inside the gelatin demonstrates that the cannula can move inside a medium which requires substantial force to move the joints of the cannula.

A. Testing of PWM Control

A1. Vision-Based Control

To verify the position-control algorithm, both links were actuated up to 11°. The period, T, was chosen as 500 ms and the controller stopped sending control signal when the error was less than 0.5°. The change of bending angle and the corresponding PWM command signal are shown in FIG. 39.

A2. Temperature Control

To verify the temperature control algorithm, the first link was heated to 44° C. The period, T, was chosen to be 1000 ms. The change of temperature and the corresponding PWM command signal is shown in FIG. 40.

B. Shape-Memory Alloy Actuator Characterization

SMA characteristics can be primarily dependent on the external stress, strain and temperature and their associated time derivatives. These variables are interdependent and the SMA behavior is a nonlinear function of these variables. Most of the constitutive models have been developed for quasistatic loading, and as such, it is assumed that the material at each instant is in thermodynamic equilibrium. Since stress is a function of temperature T, the martensite volume fraction $\lambda$, and strain $\epsilon$, the material constitutive relation in the differential form is given by Equation E4:

$$d\sigma = \frac{\partial \sigma}{\partial \epsilon}\epsilon + \frac{\partial \sigma}{\partial \lambda}\lambda + \frac{\partial \sigma}{\partial T}T \quad (4)$$

This leads to a general expression of Equation E5:

$$d\sigma = E(\epsilon,\lambda,T) + \Omega(\epsilon,\lambda,T) + \Theta(\epsilon,\lambda,T) \quad (5)$$

where $E(\epsilon,\lambda,T)$ represents the modulus of the material, $\Omega(\epsilon,\lambda,T)$ is transformation tensor and $\Theta(\epsilon,\lambda,T)$ is thermal coefficient of expansion for the SMA material. Since the strain in the SMA due to thermal expansion can be significantly lower than the strain due to phase transformation, this coefficient is normally neglected. The model developed by Tanaka (K. Tanaka, "A thermomechanical sketch of shape memory effect: One-dimensional tensile behavior", *Res. Mechanica,* 18:251-263, 1986) was used to characterize the SMA actuator. In Tanaka's model, the strain, $\epsilon$, temperature, T, and martensite volume fraction, $\lambda$, are assumed to be the only state variables. The stress, $\sigma$, in the material is calculated from these quantities. From Equation E5, the constitutive equation is derived as shown in Equation E6:

$$\sigma - \sigma_0 = E(\lambda)(\epsilon - \epsilon_0) + \Omega(\lambda)(\lambda - \lambda_0) + \Theta(\lambda)(T - T_0) \tag{6}$$

where E is the elastic modulus, $\Theta$ is a thermal coefficient of expansion, and $\Omega$ is the phase-transformation constant. The terms associated with subscript '0' refer to the initial state of the material. As set forth in Equation E7, The elastic modulus is defined as:

$$E(\lambda) = E_A + \lambda(E_M - E_A) \tag{7}$$

If we consider a material at a temperature below the martensite finish (T<$M_f$) and the zero stress/strain condition ($\epsilon_0 = 0$, $\sigma_0 = 0$), the material will be completely in the martensite phase. From Equation E6, the transformation constant, $\Omega$, can be determined as Equation E8:

$$\Omega(\lambda) = -\epsilon_L E(\lambda) \tag{8}$$

where $\epsilon_L$ is the maximum recoverable strain. Tanaka's model assumes an exponential function for the martensite volume fraction. During the martensite to austenite (M→A) transformation, $\lambda$ is given by Equation E9:

$$\lambda = e^{a_A(A_\lambda - T) + b_A \sigma} \tag{9}$$

where $a_A$, $b_A$ are constants defined as set forth in Equation E10:

$$a_A = \frac{\ln(0.01)}{A_s - A_f}, \quad b_A = \frac{a_A}{C_a} \tag{10}$$

and $C_a$ is called the stress influence coefficient. To fully characterize the SMA wire the transformation temperatures and the stress influence coefficient was determined.

An experimental setup utilizing the apparatus described below was used to characterize the SMA wire. The apparatus consists of a rotary encoder and a pin attached a fixed distance, L, from the center of the encoder. Based on the geometry of the experimental apparatus, the relationship between the encoder reading, $\theta$, and the radius of curvature, r, can be found using Equation D11 (shown below), where origin, $p_1$ is defined as the location of the SMA fixer and $p_2(x,y)$ is the location of the encoder axis (see FIG. 41). There is also a pulley mounted on the main frame and different external loadings can be applied on the SMA wire by hanging a weight. Variable external loading can be applied on the SMA wire using the extension spring that is connected directly to the force sensor (see FIG. 41). There is a cable connected to the SMA wire at point $p_5$, and it can be routed around the screw and connected to a mass via a pulley or it can be connected to the extension spring depending on what type of external loading we want to apply. To minimize the effect of air flow on the SMA characterization procedure, a transparent box was placed on the experimental apparatus during the experiments.

$$(11) \quad (L \cos \theta + x)^2 + (r - L \sin \theta - y)^2 = r^2$$

B1. Step 1: Finding the Transformation Temperatures

To find the transformation temperatures during the heating of SMA wire, $A_s$ and $A_f$, and to measure the relationship between the strain in the SMA wire and its temperature, the external stress on the SMA wire was kept constant. As the strain in the SMA wire is computed from the radius of curvature, the motion from $\theta = 0°$ was analyzed ($\epsilon^I$ as shown in FIG. 42). Initially, the SMA wire was at room temperature in the straight configuration and as the wire was heated beyond $A_s$, the wire starts to transform from the martensite phase to the austenite phase. The encoder starts recording when the SMA wire contacts the pin. Above $A_f$, the SMA wire recovers its unstrained arc shape.

Four experiments were carried out to find the strain-temperature relation of the SMA wire. To ensure good thermal contact between the RTD sensor and the SMA wire, a thermally conductive paste (OMEGATHERM® 201) was used. To ensure quasistatic deformation, the temperature of the SMA wire was increased incrementally in steps and it was maintained at each intermediate temperature. FIG. 43(*a*) shows the plot of encoder angle vs. temperature and FIG. 43(*b*) shows the plot of strain vs. temperature along with the relationship from the model using Equation D1. The transformation temperatures $A_s$ and $A_f$ were determined to be 31.5° C. and 54° C., respectively. In the model, maximum strain $\epsilon_L$ is modeled to be the strain when the SMA wire is deformed into a straight wire and bending angle, $\alpha$, is 0°. The maximum strain is 0.01624% and that corresponds to a 1.564 cm radius of curvature.

B2. Step 2: Finding the Stress Influence Coefficient

Once the transformation temperatures were found, the stress influence coefficient was determined. The stress influence coefficient quantifies the effect of stress on the phase-transformation temperatures. Different external loadings can be applied to the SMA actuator by hanging a mass via a pulley. As the temperature of the SMA wire increases, the location of the point $p_5$, where the cable is connected to the SMA actuator, changes. Let s be the distance between the origin (SMA fixer) and point $p_5$. For pure bending, the length of the wire remains unchanged and thus the location of point $p_5$ can be found using Equation E12:

$$p_5 = (r \sin \beta, r(1 - \cos \beta)) \tag{12}$$

where $\beta = s/r$. The force direction can be computed by drawing a line between points $p_5$ and $p_6$. The angle between the force vector and the x axis ranges between 84.74 and 90°. Since $\sin(84.64°) = 0.9958 \approx 1$, it can be assumed that the force acting on point $p_5$ is constant and hence characterize the SMA using the maximum stress at point $p_5$. FIG. 44 shows the strain-temperature relation of the SMA actuator under two different loadings. The $A_s$ values for 30.91 MPa and 40.85 MPa are 35° C. and 36° C., respectively. The corresponding stress influence coefficient, $C_a$, can be calculated as 8.8 MPa/° C. and 9 MPa/° C. and the average value of $C_a = 8.9$ MPa/° C. was used.

B3. Step 3: Testing Under Variable Loading

In order to investigate the behavior of the SMA wire and evaluate the model under variable loading, we have used the extension spring attached to the force sensor. As the SMA actuator transforms into its original shape from its pre-strained straight condition, it pulls the cable connected to the extension spring and the force exerted by the spring can be recorded using the force sensor. FIG. 45(*a*) shows that the external stress can be modeled as a straight line for this experimental setup. FIG. 45(*b*) shows the strain in the SMA wire and the strain calculated using Tanaka's model with material constants $C_a$=8.9 MPa/° C., $E_M$=28 GPa and $E_A$=78 GPa.

B4. Step 4: Finding the Relationship Between the Bending Angle and the Strain

The bending (joint) angle was defined as the angle between consecutive links, and the geometric relation between the strain in the SMA wire and the corresponding bending angle was to be determined. To find this relation, two small links were attached at the tips of the SMA wire and markers were placed on the links and the tracking algorithm was used to find the bending angle between the links (FIG. 46). FIG. 47(a) shows the change in bending angle with the strain calculated using Tanaka's model at that temperature and the exponential ($R^2$=0.9819) curve fit is given by Equation E13:

$$\alpha = 49.77 e^{-779.1\epsilon} + 17.82 e^{-142.8\epsilon} \qquad (13)$$

B5. Step 5: Characterizing the Discretely Actuated Steerable Cannula

The experiment was repeated to find the strain-temperature relation under no stress after the cannula is assembled, and the results showed that the transformation temperatures of the SMA actuator increases (FIG. 47(b)) due to the induced stress by the sheath and the crimps on the SMA wire. The model developed for the SMA actuator can be extended and capture the overall effect of the sheath and the crimps by selecting $A_s$ and $A_f$ in the model as 37° C. and 68° C., respectively. Any external stress can be substituted into Equation E6 to find the change in strain (and thus the bending angle) with temperature.

If the external stress is known, the strain in SMA is only a function of its temperature. Tanaka's model enables the determination of the change in strain with temperature by solving the nonlinear equation given in Equation E6. The desired temperature of the wire (and hence the strain) can then be controlled using the PWM-based temperature controller. To determine the external stress acting on the SMA actuators, there are two possible options that were considered. First, incorporating a force sensor in the cannula design can enable the measurement of the external stress. The other option is to incorporate tissue models into the Tanaka's model so that the external stress term can be related to the desired deformation that the cannula will cause in the soft tissue.

C. Testing of the Maximum Force

To quantify the maximum force that can be generated by the SMA wires, the experimental setup described below was used. A MBD-2.5 force sensor (Transducer Techniques Inc.) was used to measure the maximum force generated at the joints. The cannula and the force sensor were fixed during the measurements. Thus, the SMA wire was kept at zero strain which enabled the measurement of the maximum force exerted, $F_{block}$, at the joint. A continuous 1.9 A current was supplied to the SMA wire. All the examples developed generated a maximum force of between 2.3-2.7 N at each joint.

D. Testing Inside Gelatin

To mimic motion in tissue, the cannula motion was evaluated in a phantom of Knox Gelatine (Kraft Foods Inc.). Three packets of gelatin were dissolved in cold water inside a 200 mL cup. Two cups of boiling water were added to the mixture, which was kept inside a refrigerator until it was fully hardened. During the experiments, the gelatin was maintained at 15° C. A small hole was drilled on the side of the container and the cannula was clamped between two steel blocks to keep it fixed during the experiment. The period, T, was chosen to be 1000 ms and the controller stopped sending control signals when the error was less than 1°.

Initially, the first joint was actuated to 15° and then the desired angle was incremented by 1° up to 20°. The change in bending angle with time is shown in FIG. 48(a). The initial actuation took relatively longer compared to actuation in air (FIG. 39(a)) due to heat loss from the SMA wires to gelatin, as the transition temperature of the final SMA wire was substantially higher than the temperature of the gelatin (15° C.). The snapshots from the experiment are shown in FIG. 48(b). It is clear from this experiment that the SMA actuator at the joint can exert substantial force to bend inside a medium where a significant force is required to move the medium around.

Trajectory Planning and Execution of the Cannula

There have been various approaches to the trajectory planning of flexible needles and cannulas in the past decade. Motion-planning techniques requiring the minimization of a suitable cost function have been widely used. Additional constraints may be imposed on trajectory planning such as obstacle avoidance and minimum path. The control space of the flexible needles has been discretized and the optimization problem has been formulated using a cost function that minimizes the control effort and path length. Others applied a numeric diffusion-based method for trajectory planning of flexible needles in an obstacle-free 3D environment. Still others used fluoroscopic images of the tissue before needle insertion to find the location of the obstacle, needle tip, and the target, and through these three points they passed a spline trajectory to find the insertion trajectory. Others used rapidly exploring random trees to find the feasible paths in a configuration space. For flexible needles, finite-element modeling has also been used for planning paths around obstacles in deformable tissue. Planned trajectories for the active cannula for lung biopsy procedures by using a cost function that depends on the tubular environment geometry have been examined. These methods cannot be directly applied to the discretely actuated steerable cannula since these devices are structurally different. For the discretely actuated steerable cannula, it is also difficult to control the strain rate (and hence the joint velocity) of the SMA actuator using the PWM-based controllers since the bending angle is all that can be controlled and maintained. Thus, a kinematic approach was followed for trajectory planning and execution of the cannula trajectory. This approach was used to generate a minimum path between the desired and final configurations in an obstacle-free environment. As set forth in Equation E14, the twist coordinate, $\xi$, for a revolute joint is defined as:

$$\xi = \begin{bmatrix} -w_i \times q_i \\ w_i \end{bmatrix} \qquad (14)$$

where $w_i \in R^3$ is a unit vector in the direction of the twist axis and $q_i \in R^3$ is any point on the axis. For a prismatic joint, the twist coordinate is given by Equation E15:

$$\xi = \begin{bmatrix} v_i \\ 0 \end{bmatrix} \qquad (15)$$

where $v_i \in R^3$ is a unit vector pointing in the direction of translation. For the cannula in FIG. 49, Equation E16 (below) applies:

$$q_1 = [0,0,0], q_2 = [0,0,l_1], q_3 = [0,l_1,l_1+l_2]$$

$$v_1 = [0,0,1], \omega_2 = [1,0,0], \omega_3 = [\cos(\beta), \sin(\beta), 0] \quad (16)$$

The forward kinematics map can be written as set forth in Equations E17 and E18:

$$g_{st} = e^{\hat{\xi}_1 u} e^{\hat{\xi}_2 \alpha_1} e^{\hat{\xi}_3 \alpha_2} g_{st}(0) \quad (17)$$

where $$g_{st}(0) = \begin{bmatrix} I & \begin{matrix} 0 \\ 0 \\ l_1+l_2+l_3 \end{matrix} \\ 0 & 1 \end{bmatrix} \quad (18)$$

The equations were derived for the general case where the SMA at the second joint can be placed at an arbitrary angle $\beta$ with respect to the first joint. In one exemplary prototype, $\beta$ is 90°; $l_1$, $l_2$, and $l_3$ are 60.5, 40.5 and 30.5 mm respectively. $g_{st}$ can be represented as Equation E19:

$$g_{st} = \begin{bmatrix} R & p \\ 0 & 1 \end{bmatrix} \quad (19)$$

where $R \in SO(3)$ is the orientation of frame T, relative to frame S and $p \in R^3$ is the position vector of the origin of frame T from the origin of frame S. The 3D position of the tip, p(q), is given by Equation E20:

$$p(q) = \begin{bmatrix} l_2 s_\beta s_{\alpha_2} \\ -l_2 s_{\alpha_1} - l_3(s_{\alpha_1} c_{\alpha_2} + c_\beta s_{\alpha_2} c_{\alpha_1}) \\ l_1 + u + l_2 c_{\alpha_1} + l_3(c_{\alpha_1} c_{\alpha_2} - c_\beta s_{\alpha_1} s_{\alpha_2}) \end{bmatrix} \quad (20)$$

The infinitesimal arc length, $d\gamma$, can be written as Equation E21:

$$d\gamma^2 = \Sigma g_{ij} dq^i dq^j \quad (21)$$

where $g_{ij}$ are the terms of the metric tensor, G (G is symmetric). The individual terms of the metric tensor, G, are given by Equation E22:

$$g_{11} = (l_2 s_{\alpha_1} + l_3(s_{\alpha_1} c_{\alpha_2} + c_\beta s_{\alpha_2} c_{\alpha_1}))^2 + \quad (22)$$
$$(l_2 c_{\alpha_1} + l_3(c_{\alpha_1} c_{\alpha_2} - c_\beta s_{\alpha_1} s_{\alpha_2}))^2$$
$$g_{12} = l_3((s_{\alpha_2} c_{\alpha_1} + c_\beta s_{\alpha_1} c_{\alpha_2})(l_2 s_{\alpha_1} + l_3(s_{\alpha_1} c_{\alpha_2} + c_\beta s_{\alpha_2} c_{\alpha_1})) -$$
$$(s_{\alpha_1} c_{\alpha_2} - c_\beta s_{\alpha_1} c_{\alpha_2})(l_2 c_{\alpha_1} + l_3(s_{\alpha_1} c_{\alpha_2} - c_\beta s_{\alpha_1} c_{\alpha_2})))$$
$$g_{13} = -l_2 s_{\alpha_1} - l_3(s_{\alpha_1} c_{\alpha_2} + c_\beta s_{\alpha_2} c_{\alpha_1})$$
$$g_{22} = l_3^2(s_\beta^2 c_{\alpha_2}^2 + (s_{\alpha_2} c_{\alpha_1} + c_\beta s_{\alpha_1} c_{\alpha_2})^2 + (s_{\alpha_1} s_{\alpha_2} - c_\beta c_{\alpha_1} c_{\alpha_2})^2)$$
$$g_{23} = -l_3(s_{\alpha_2} c_{\alpha_1} + c_\beta s_{\alpha_1} c_{\alpha_2})$$
$$g_{33} = 1$$

In this case, finding curves of zero acceleration are of interest, namely geodesics on the manifold. The geodesic equation can be written as Equation E23:

$$\ddot{q}_k + \sum_{i,j} \Gamma_{ij}^k \dot{q}_i \dot{q}_j = 0 \quad (23)$$

where $\Gamma_{ij}^k$ is the Christoffel symbol defined in terms of the elements of the metric tensor as Equation E24:

$$\Gamma_{ij}^k = \frac{1}{2} \sum_l \left[ \frac{\partial g_{il}}{\partial q_j} - \frac{\partial g_{ij}}{\partial q_l} + \frac{\partial g_{ij}}{\partial q_i} \right] g^{lk} \quad (24)$$

where $g^{lk}$ are the entries of the inverse of G. Equation E23 produces three second-order differential equations which can be converted into six first-order differential equations. The trajectory for the minimum distance between the desired initial and final configurations can be computed numerically by solving a two-point boundary value problem. The trajectory is parameterized by $\eta$, where $\eta$ ranges between 0 (initial configuration) and 1 (final configuration).

The bvp4c function in MATLAB was used to solve the problem. If the boundary conditions are selected as set forth in Equation E25:

$$u_i = 0, \alpha_{1i} = 0°, \alpha_{2i} = 0°$$
$$u_f = 0, \alpha_{1f} = 30°, \alpha_{2f} = 20° \quad (25)$$

the resulting motion is shown in FIG. 50 where the joint angles $\alpha_1$ and $\alpha_2$ change linearly with respect to the parameter $\eta$ from 0-20° and 0-30°, respectively.

TABLE 1

Data points selected along the trajectory and corresponding desired bending angles.

| $\eta$ | $\alpha_1$ | $\alpha_2$ |
|---|---|---|
| 0.202 | 6° | 4° |
| 0.303 | 9.5° | 6.5° |
| 0.424 | 13° | 8° |
| 0.505 | 14.8° | 9.8° |
| 0.606 | 18° | 11.8° |
| 0.707 | 20.8° | 14° |
| 0.818 | 24° | 16° |
| 0.899 | 27° | 18° |
| 1 | 30° | 20° |

To execute the trajectory-planning scheme, the trajectory was dived into nine intervals by selecting nine data points along the trajectory. To control the position and achieve the desired bending angle at these nine locations along the trajectory was desired. Table E.1 (above) shows the data points and the desired bending angles. Initially, the angles corresponding to the first data point were entered as the desired bending angles. Once both of the joints reached the desired angles, the angles corresponding to the next data point were entered as the new desired angles. When the markers were along the line that corresponds to bending angles $\alpha_1=0$ and $\alpha_2=0$, it was observed that there are variations in the bending angle readings. This makes it difficult to control bending angles that are close to zero, angles less than two degrees in particular. Therefore, a longer interval was selected for the first interval. FIG. 51 shows the change of bending angle with time and $\alpha_{off}$ represents the interval when the new desired inputs were entered. The trajectory between each arc length interval is locally a geodesic. For each interval, the reparametrization between the parameter $\eta$ and time is given by Equation E26, where the subscripts i and f represent the starting point of the interval when the desired angles were entered and the final point when both links reached the desired angles of the interval, respectively. The data points showing the desired angles for the intervals and the results of the simulation and experiment are shown in FIG. 52. The 3D position of the tip of the cannula can be calculated from the forward kinematics map and is given in FIG. 53. The errors along the trajectory are given in FIG. 54 and the global error between the final configuration and the target location is 0.29 mm. The maximum error occurs in the first interval due to the fact that this interval is longer than the other intervals and therefore the resolution is smaller for this interval (see FIG. 54).

$$\eta = \frac{t - t_i}{t_f - t_i} \cdot (\eta_f - \eta_i) + \eta_i \qquad (26)$$

Optical Coherence Tomography Imaging Experiments

The feasibility of using the OCT-integrated cannula for tissue imaging was tested on two different biological samples. The aim of the experiments presented in this section is not to quantify the performance of the particular OCT probe, but to verify the imaging capability of the cannula during bending since using the cannula to enable in situ imaging at the target location would be useful. To test the imaging capabilities, an experimental setup was used, which consists of the biological sample, the PZT actuator, the OCT probe, the cannula, and a OCT reference arm.

First, the cannula and the OCT system were tested on chicken breast. The OCT probe was inserted into the cannula before insertion into soft tissue. A current of 1.4 A was supplied to the first joint. The same procedure was carried out inside porcine tissue as well. The images were recorded throughout the bending process and are shown in FIG. 55. The images are placed with increasing bending angle from left to right, the first one showing the initial OCT image. The images of connective tissues in porcine tissue and the muscle fibers in chicken breast can be clearly resolved by the imaging system before and during bending. As the bending angle increases, the scanning range of the OCT probe in the imaging window becomes smaller and smaller until it finally stops. FIG. 56 shows the histogram of the four images for the two tests. The images are numbered from 1 to 4 from left to right. The histogram of the images during bending indicates that the images have very similar contrast levels, except the image corresponding to the seized probe (last images). When the probe was stuck, the pixel values at different lateral positions were from the same A-scan and thus, the image appeared as multiple straight lines. These straight lines increase the histogram distribution on the high-intensity portion. These results show that the image quality is not affected by the bending of the cannula.

In initial experiments, the cannula was not visible inside the tissue, and no information about the angle at which the OCT probe contacts the inner wall was attained. In the second part of the experiments, the angle at which this contact takes place was quantified. The Micron Tracker camera was placed in front of the setup to track the bending angle during OCT imaging and was wrapped with a tape around the imaging window. This setup enabled measurement of the bending angle at which the scanning range of the OCT probe would start to decrease. Since tape was only wrapped around the imaging window, the markers were clearly detected and the pose-tracking algorithm was used to measure the bending angle. The inner wall of the cannula, sheath and tape can be clearly seen in the OCT image (see FIG. 57) and OCT images at various angles are shown in FIG. 58. As the bending angle increased, the OCT probe got closer to the inner wall and the decrease in distance between the OCT probe and imaging window at larger angles limits the field of view. The OCT probe contacted the inner wall at 8.334°. The PZT actuator also causes lateral vibration which becomes more apparent when looking at the cannula's inner wall in FIG. 57. Note that the bending angle of the OCT probe itself is only limited by the nitinol tubing that is used to protect the probe from the environment. The maximum bending angle that can be achieved with the OCT-integrated cannula, can be improved by incorporating a mechanism inside the cannula that would hold the OCT probe in place during bending to prevent it from contacting the inner wall.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A steerable probe having a central axis, a first end, and an opposed second end, the probe having a length corresponding to the distance between the first end and the second end, the probe comprising:
   a plurality of substantially straight segments disposed along the length of said probe in a spaced apart relationship each with respect to another, each substantially straight segment of the plurality thereof defining a respective central bore extending substantially through the entire length of said each substantially straight segment along the central axis of the probe, wherein said respective central bores of the plurality of substantially straight spaced apart segments cooperate each with another to define an inner channel extending substantially through the entire length of the probe, said plurality of substantially straight segments comprising a first end segment at the first end of said probe and a second end segment at the second end of said probe, at least one of said first and second ends of said probe defining at least one opening in communication with the inner channel to receive at least one of a therapeutic and diagnostic tools; and
   at least one joint assembly coupled between adjacent ones of said plurality of substantially straight segments, said at least one joint assembly comprising:
      at least one actuator member formed from a Shape Memory Alloy (SMA) pre-configured in a memory reference arcuated shape having a substantially single bent portion and a pair of substantially straight end portions, each one of said pair of end portions extending at a respective end of said substantially single bent portion in connection therewith and in an angled relationship one with respect to another, wherein said each substantially straight end portion of said at least one actuator member is secured to and extends along a length of a respective one of said adjacent substantially straight segments of said plurality thereof, wherein said adjacent segments of said plurality thereof are operatively coupled each to another via said at least one actuator member with said substantially single bent portion of said at least one actuator member positioned between said adjacent substantially straight segments, thereby defining a respective at least one joint of the probe, wherein said at least one actuator member is configured for selective actuation, and wherein, in response to said selective actuation applied to said at least one actuator member, said substantially single bent portion undergoes a bending transformation changing a curvature thereof, thus changing an angular relationship between said substantially straight ending portions of said at least one actuator member, thereby adjusting an angular relationship between said adjacent substantially straight segments, and thereby controlling a shape of the probe.

2. The steerable probe of claim 1, wherein the inner channel of the probe comprises a transparent imaging side window, said inner channel being configured to receive at least one of a diagnostic tool and a therapeutic tool.

3. The steerable probe of claim 1, wherein said at least one joint assembly comprises a sheath disposed in proximity to said adjacent substantially straight segments and configured to receive said substantially single bent portion of said at least one actuator member of said at least one joint assembly, wherein the sheath is secured to and positioned between said adjacent substantially straight segments of the plurality thereof.

4. The steerable probe of claim 3, wherein said sheath of said at least one joint assembly comprises a non-conductive material.

5. The steerable probe of claim 4, wherein the sheath is made of a material selected from a group comprising an enamel and heat shrink tubing.

6. The steerable probe of claim 3, wherein each of the plurality of spaced substantially straight segments has respective walls, wherein said each segment of the plurality thereof defines at least one crimp disposed oppposedly to a corresponding crimp defined by a segment adjacent to said each segment, wherein at least one pair of opposed crimps is positioned at said at least one joint assembly, and wherein each pair of opposed crimps is configured to receive corresponding end portions of said at least one actuator member of the at least one joint assembly.

7. The steerable probe of claim 1, further comprising an outer sheath extending along substantially the entire length of the probe.

8. The steerable probe of claim 1, wherein each of the plurality of spaced substantially straight segments has respective walls, wherein said each substantially straight segment defines at least one slot that is opposed to a corresponding slot defined at a substantially straight segment adjacent to said each substantially straight segment, wherein at least one pair of opposed slots is positioned at said at least one joint assembly, and wherein said at least one pair of opposed slots is configured to receive corresponding ending portions of said at least one actuator member of the at least one joint assembly.

9. The steerable probe of claim 8, wherein said at least one actuator member of said at least one joint assembly includes at least two said actuator members disposed in a predetermined relationship one with respect to another, wherein the at least one pair of opposed slots at said at least one joint assembly comprises at least two pairs of said opposed slots, each slot accommodating one of the end portions of a respective one of said at least two actuator members, and wherein said selective actuation is applied independently to a respective at least one of said at least two actuator members depending on a required direction of a relative displacement of said adjacent segments.

10. The steerable probe of claim 8, wherein the at least one actuator member of said at least one joint assembly comprises at least one pair of antagonistically disposed and actuated actuator members, and wherein the at least one pair of opposed slots at said at least one joint assembly comprises at least two pairs of opposed slots, each slot accommodating one of the end portions of said at least one pair of antagonistic actuator members.

11. The steerable probe of claim 8, wherein the at least one actuator member of said at least one joint assembly comprises a plurality of actuator members disposed in a predetermined relationship each with respect to another, and wherein the substantially single bent portion of each actuator member of said plurality thereof bends in a respective bending direction corresponding to said predetermined disposition of said each actuator member.

12. The steerable probe of claim 1, wherein said at least one joint assembly comprises a pair of spaced rings respectively secured to adjacent substantially straight segments of the plurality thereof at opposing sides of the respective at least one joint of the probe, wherein the at least one actuator member of the at least one joint assembly is positioned between the adjacent substantially straight segments and the pair of spaced rings, wherein each actuator member is secured to said adjacent substantially straight segments.

13. The steerable probe of claim 12, further comprising a non-conductive material layer positioned between the adjacent substantially straight segments and the at least one actuator member.

14. The steerable probe of claim 1, wherein each joint assembly comprises at least one temperature sensor, each temperature sensor being operatively coupled to a respective actuator member.

15. The steerable probe of claim 1, wherein said at least one actuator member pre-configured in said memory reference arcuated shape is deformed into a straight configuration in the absence of said selective actuation, and wherein, upon application of said selective actuation to said at least one actuator member, said substantially single bent portion undergoes a configuration transformation between said straight configuration and a curved configuration, thereby changing a relative disposition between said adjacent substantially straight segments secured to said end portions of said substantially single bent portion of said at least one actuator member.

16. The steerable probe of claim 15, wherein said segments and said end portions of said at least one actuator member remain substantially straight during said configuration transformation of said substantially single bent portion.

17. The steerable probe of claim 1, wherein each of the plurality of spaced substantially straight segments has respective walls, wherein said respective walls of said each segment of the plurality thereof is configured with at least one hole disposed oppposedly to a corresponding hole defined in said respective walls of a segment adjacent to said each segment, wherein at least one pair of opposed holes is positioned at each joint assembly, and wherein each pair of opposed holes is configured to receive corresponding end portions of said at least one actuator member of the at least one joint assembly.

18. A steerable probe having a central axis, a first end, and an opposed second end, the probe having a length corresponding to the distance between the first end and the second end, the probe comprising:

a plurality of substantially straight segments disposed along the length of said probe in a spaced apart relationship each with respect to another, each substantially straight segment of the plurality thereof defining a respective central bore extending along the central axis of the probe, wherein said respective central bores of the plurality of substantially straight spaced apart segments cooperate each with another to define an inner channel of the probe; and at least one joint assembly coupled between adjacent ones of said plurality of substantially straight segments, said at least one joint assembly comprising:

at least one actuator member formed from a Shape Memory Alloy (SMA) pre-configured in a memory reference arcuated shape having a substantially single bent portion and a pair of substantially straight end portions, each one of said pair of end portions extending at a respective end of said substantially single bent portion in connection therewith and in an angled relationship one with respect to another, wherein said each substantially straight end portion of said at least one actuator member is secured to and extends along a length of a respective one of said adjacent substantially straight segments of said plurality thereof, wherein said adjacent segments of said plurality thereof are operatively coupled each to another via said at least one actuator member with said substantially single bent portion of said at least one actuator member positioned between said adjacent substantially straight segments, thereby defining a respective at least one joint of the probe, wherein said at least one actuator member is configured for selective actuation, and wherein, in response to said selective actuation applied to said at least one actuator member, said substantially single bent portion undergoes a bending transformation changing a curvature thereof, thus changing an angular relationship between said substantially straight ending portions of said at least one actuator member, thereby adjusting an angular relationship between said adjacent substantially straight segments, and thereby controlling a shape of the probe, wherein the inner channel of the probe comprises a transparent imaging side window, said inner channel being configured to receive at least one of a diagnostic tool, and a therapeutic tool, and wherein the plurality of spaced segments comprise a first end segment defining the first end of the probe and a second end segment defining the second end of the probe, the first end of the probe defining at least one opening configured to receive electrical wiring and at least one of a diagnostic tool and a therapeutic tool.

19. The steerable probe of claim 18, wherein the second end of the probe defines an opening in communication with the inner channel.

20. The steerable probe of claim 18, wherein the second end of the probe is beveled.

21. A probe system comprising:

a steerable probe having a central axis, a first end, and an opposed second end, the probe having a length corresponding to the distance between the first end and the second end, the probe comprising:

a plurality of substantially straight spaced segments, each segment of the plurality thereof defining a respective central bore extending substantially through the entire length of said each segment along the central axis of the probe, wherein the central bores of the plurality of spaced segments cooperate to define an inner channel extending substantially through the entire length of the probe, said plurality of substantially straight segments comprising a first end segment at the first end of said probe and a second end segment at the second end of said probe, at least one of said first and second ends of said probe defining at least one opening in communication with the inner channel to receive at least one of a therapeutic and diagnostic tools;

at least one joint assembly including:

at least one actuator member formed from a shape memory alloy (SMA) and pre-configured in a memory reference arcuated shape having a substantially single bent portion and a pair of substantially straight end portions, each of said pair of end portions extending at a respective end of said substantially single bent portion in connection therewith in an angled relationship one to another, said at least one actuator member being secured to and between adjacent segments of the plurality thereof, with each segment of the plurality of spaced segments being operatively coupled to an adjacent segment of the plurality of spaced segments, wherein said substantially single bent portion of said at least one actuator member is positioned between the adjacent segments of the plurality thereof, thereby defining a respective at least one joint of the probe, wherein said at least one actuator member is configured for an independent selective actuation, wherein said at least one actuator member pre-configured into said memory reference arcuated shape is deformed into a straight initial configuration in the absence of a selective actuation, and wherein, in response to said independent selective actuation applied to said at least one actuator member, said substantially single bent of said at least one actuator member undergoes a bending transformation between said straight initial configuration and a curved configuration, thereby changing a relative angular disposition between said adjacent segments, thus changing the shape of said probe as required by a medical procedure.

22. The probe system of claim 21, further including means for selectively effecting the bending transformation of the substantially single bent portion of said at least one actuator member, said means comprising a controller positioned in operative communication with said at least one actuator member of the probe, wherein the controller is configured to selectively deliver a control input to said at least one actuator member of the probe.

23. The probe system of claim 22, wherein the controller is a pulse-width-modulated-based (PWM-based) controller.

24. The probe system of claim 23, wherein said at least one joint assembly of the probe comprises at least one temperature sensor disposed in electrical communication with the PWM-based controller and operatively coupled to the at least one actuator member, wherein said at least one temperature sensor is configured to produce an output signal indicative of the temperature of the at least one actuator member, and wherein said at least one temperature sensor is further configured to transmit an output signal generated thereat to the PWM-based controller, wherein the PWM-based controller is configured to selectively deliver the control input to each respective actuator member based upon the measured temperature and a constitutive model of said at least one SMA actuator member.

25. The probe system of claim 24, further comprising:
an imaging means, the imaging means being configured to produce at least one image depicting the location of the probe; and
a processor in communication with the imaging means and configured to receive the at least one image from the imaging means, the processor being configured to determine the location of the probe based upon the at least one image,
wherein the processor is in operative communication with the PWM-based controller.

26. The probe system of claim 25, wherein the PWM-based controller is configured to selectively deliver current to the at least one actuator member in response to the detection of a bending angle of the substantially single bent portion of said at least one actuator member by the processor.

27. The probe system of claim 23, further comprising means for measuring the resistance of said at least one actuator member of the probe, wherein the PWM-based controller is configured to selectively deliver the control input to said at least one actuator member based upon the measured resistance of the at least one actuator member.

28. The probe system of claim 21, wherein the probe system further comprises:
an imaging means, the imaging means being configured to produce at least one image depicting the location of the probe; and
a processor in communication with the imaging means and configured to receive the at least one image from the imaging means, the processor being configured to determine the location of the probe based upon the at least one image.

29. The probe system of claim 28, wherein the imaging means is selected from a group including a Computed Tomography (CT) machine, a Magnetic Resonance Imaging (MRI) machine, an Ultrasound machine, and a Fluoroscopy machine.

30. The probe system of claim 28, wherein the probe defines at least one imaging window in communication with the inner channel of the probe, and wherein the imaging means is positioned within the inner channel of the probe.

31. The probe system of claim 28, wherein said processor is further configured for a vision-based feedback control routine by computing an adjustment control signal responsive to said at least one image received from said imaging means, wherein said adjustment control signal reflects a deviation between a current position and a desired position of the probe, and wherein said adjustment control signal is supplied to said at least one actuator member for selective actuation of said at least one actuator member to adjust the shape of the probe, thereby guiding the probe to said desired position.

* * * * *